US011649451B2

(12) United States Patent
Liu et al.

(10) Patent No.: US 11,649,451 B2
(45) Date of Patent: May 16, 2023

(54) EVOLUTION OF BIOACTIVE SEQUENCE-DEFINED SYNTHETIC POLYMERS USING DNA-TEMPLATED POLYMERIZATION

(71) Applicant: President and Fellows of Harvard College, Cambridge, MA (US)

(72) Inventors: David R. Liu, Lexington, MA (US); Zhen Chen, Boston, MA (US); Phillip Andrew Lichtor, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 67 days.

(21) Appl. No.: 16/629,013

(22) PCT Filed: Jul. 6, 2018

(86) PCT No.: PCT/US2018/041127
§ 371 (c)(1),
(2) Date: Jan. 6, 2020

(87) PCT Pub. No.: WO2019/010441
PCT Pub. Date: Jan. 10, 2019

(65) Prior Publication Data
US 2020/0172896 A1 Jun. 4, 2020

Related U.S. Application Data

(60) Provisional application No. 62/638,901, filed on Mar. 5, 2018, provisional application No. 62/529,787, filed on Jul. 7, 2017.

(51) Int. Cl.
*C12N 15/10* (2006.01)
*A61K 31/7115* (2006.01)

(52) U.S. Cl.
CPC ...... *C12N 15/1068* (2013.01); *A61K 31/7115* (2013.01)

(58) Field of Classification Search
CPC .................. C12N 15/1068; A61K 31/7115
See application file for complete search history.

(56) References Cited

U.S. PATENT DOCUMENTS

2006/0160763 A1* 7/2006 Segev ............... C07H 19/20
544/243

OTHER PUBLICATIONS

Hollenstein, Generation of long, fully modified, and serum-resistant oligonucleotides by rolling circle amplification, Org. Biomol. Chem., 2015, 13: 9820-9824 (Year: 2015).*
Bashkin etal, Synthesis and Characterization of Oligonucleotide Peptides, 1990, J.Org.Chem., vol. 56, No. 9: 3168-3176 (Year: 1990).*
International Search Report and Written Opinion, dated Oct. 19, 2018, in connection with Application No. PCT/US2018/041127.
International Preliminary Report on Patentability, dated Jan. 16, 2020, in connection with Application No. PCT/US2018/041127.
Alam et al., FASTAptamer: A Bioinformatic Toolkit for High-throughput Sequence Analysis of Combinatorial Selections. Mol Ther Nucleic Acids. Mar. 2015; 4(3): e230. Published online Mar. 3, 2015. doi: 10.1038/mtna.2015.4. 10 pages.
Bock et al., Selection of single-stranded DNA molecules that bind and inhibit human thrombin. Nature. Feb. 6, 1992;355(6360):564-6. doi: 10.1038/355564a0.
Breaker et al., A Dna enzyme that cleaves RNA. Chem Biol. Dec. 1994;1(4):223-9. doi: 10.1016/1074-5521(94)90014-0.
Brudno et al., Recent Progress Toward the Templated Synthesis and Directed Evolution of Sequence-Defined Synthetic Polymers. Chem Biol. Mar. 27, 2009; 16(3): 265-276. doi: 10.1016/j.chembiol.2009.02.004.
Brudno et al., An In Vitro Translation, Selection, and Amplification System for Peptide Nucleic Acids. Nat Chem Biol. Feb. 2010; 6(2): 148-155. Published online Dec. 27, 2009. doi: 10.1038/nchembio.280.
Chan et al., Discovery of a Covalent Kinase Inhibitor from a DNA-Encoded Small-Molecule Library x Protein Library Selection. J Am Chem Soc. Aug. 2, 2017;139(30):10192-10195.
Chan et al., Discovery of a Covalent Kinase Inhibitor from a DNA-Encoded Small-Molecule Library x Protein Library Selection, Supporting Information. J Am Chem Soc. Aug. 2, 2017;139(30):36 pages.
Chaput et al., The emerging world of synthetic genetics. Chem Biol. Nov. 21, 2012;19(11):1360-71. doi: 10.1016/j.chembiol.2012.10.011.
Chen et al., Evolution of sequence-defined highly functionalized nucleic acid polymers. Nature Chemistry. Mar. 5, 2018; 10(4):420-7.
Chen et al., Evolution of sequence-defined highly functionalized nucleic acid polymers, Supplementary Information. Nature Chemistry. Mar. 5, 2018;10(4):37 pages.
Chen et al., Nucleic acid templates synthesis of sequence defined synthetic polymers. In Sequence Controlled Polymers, First Edition. Chapter 3. Dec. 4, 2017:49-90.
Cohen et al., Sequence variations in PCSK9, low LDL, and protection against coronary heart disease. N Engl J Med. Mar. 23, 2006;354(12):1264-72. doi: 10.1056/NEJMoa054013.
Crooks et al., WebLogo: a sequence logo generator. Genome Res. Jun. 2004;14(6):1188-90. doi: 10.1101/gr.849004.
Davies et al., Unique motifs and hydrophobic interactions shape the binding of modified DNA ligands to protein targets. Proc Natl Acad Sci U S A. Dec. 4, 2012;109(49):19971-6. doi: 10.1073/pnas.1213933109. Epub Nov. 8, 2012.

(Continued)

*Primary Examiner* — Ekaterina Poliakova-Georgantas
(74) *Attorney, Agent, or Firm* — Wolf, Greenfield & Sacks, P.C.

(57) ABSTRACT

The present invention provides methods and compositions for performing ordered multi-step syntheses involving modified nucleic acids by nucleic acid-mediated chemistry. This approach is useful for generating sequence-defined highly functionalized nucleic acid polymers. The invention also provides modified nucleic acid polymers that bind to proteins of interest (e.g., PCSK9 and IL-6), which are implicated in human disease.

17 Claims, 22 Drawing Sheets

Specification includes a Sequence Listing.

(56) References Cited

OTHER PUBLICATIONS

Dunn et al., Reverse Transcription of Threose Nucleic Acid by a Naturally Occurring DNA Polymerase. Chembiochem. Oct. 4, 2016;17(19):1804-1808. doi: 10.1002/cbic.201600338. Epub Aug. 4, 2016.
Ellington et al., In vitro selection of RNA molecules that bind specific ligands. Nature. Aug. 30, 1990;346(6287):818-22. doi: 10.1038/346818a0.
Ellington et al., Selection in vitro of single-stranded DNA molecules that fold into specific ligand-binding structures. Nature. Feb. 27, 1992;355(6363):850-2. doi: 10.1038/355850a0.
Gawande et al., Selection of DNA aptamers with two modified bases. Proc Natl Acad Sci U S A. Mar. 14, 2017;114(11):2898-2903. doi: 10.1073/pnas.1615475114. Epub Mar. 6, 2017.
Gelinas et al., Crystal Structure of Interleukin-6 in Complex with a Modified Nucleic Acid Ligand. J. Biol. Chem. 2014; 289:8720-8734.
Gibbs et al., Impact of Target-Mediated Elimination on the Dose and Regimen of Evolocumab, a Human Monoclonal Antibody Against Proprotein Convertase Subtilisin/Kexin Type 9 (PCSK9). J Clin Pharmacol. May 2017;57(5):616-626. doi: 10.1002/jcph.840. Epub Nov. 15, 2016.
Gold et al., Aptamer-based multiplexed proteomic technology for biomarker discovery. PLoS One. Dec. 7, 2010;5(12):e15004. doi: 10.1371/journal.pone.0015004. 17 pages.
Guo et al., Fidelity of the DNA Ligase-Catalyzed Scaffolding of Peptide Fragments on Nucleic Acid Polymers. Bioconjugate Chemistry. Dec. 19, 2016;28(2):314-8.
Guo et al., Fidelity of the DNA Ligase-Catalyzed Scaffolding of Peptide Fragments on Nucleic Acid Polymers, Supporting Information. Bioconjugate Chemistry. Dec. 19, 2016;28(2):19 pages.
GUO et al., Sequence-Defined Scaffolding of Peptides on Nucleic Acid Polymers. J Am Chem Soc. Sep. 2, 2015;137(34):11191-6. doi: 10.1021/jacs.5b07675. Epub Aug. 21, 2015.
Gupta et al., Chemically modified DNA aptamers bind interleukin-6 with high affinity and inhibit signaling by blocking its interaction with interleukin-6 receptor. J Biol Chem. Mar. 21, 2014;289(12):8706-19. doi: 10.1074/jbc.M113.532580. Epub Jan. 12, 2014.
Hili et al., DNA ligase-mediated translation of DNA into densely functionalized nucleic acid polymers. Journal of the American Chemical Society. Jan. 9, 2013;135(1):98-101.
Hili et al., DNA ligase-mediated translation of DNA into densely functionalized nucleic acid polymers, Supporting Information. Journal of the American Chemical Society. Jan. 9, 2013;135(1):20 pages.
Hollenstein, Nucleoside triphosphates—building blocks for the modification of nucleic acids. Molecules. Nov. 15, 2012;17(11):13569-91. doi: 10.3390/molecules171113569.
Hollenstein et al., A self-cleaving DNA enzyme modified with amines, guanidines and imidazoles operates independently of divalent metal cations (M2+). Nucleic Acids Res. Apr. 2009;37(5):1638-49. doi: 10.1093/nar/gkn1070. Epub Jan. 19, 2009.
Hunter et al., IL-6 as a keystone cytokine in health and disease. Nat Immunol. May 2015;16(5):448-57. doi: 10.1038/ni.3153.
Imaizumi et al., Efficacy of base-modification on target binding of small molecule DNA aptamers. J Am Chem Soc. Jun. 26, 2013;135(25):9412-9. doi: 10.1021/ja4012222. Epub Jun. 18, 2013.
Kuhnast et al., Alirocumab inhibits atherosclerosis, improves the plaque morphology, and enhances the effects of a statin. J Lipid Res. Oct. 2014;55(10):2103-12. doi: 10.1194/jlr.M051326. Epub Aug. 19, 2014.
Kimoto et al., Generation of high-affinity DNA aptamers using an expanded genetic alphabet. Nat Biotechnol. May 2013;31(5):453-7. doi: 10.1038/nbt.2556. Epub Apr. 7, 2013.
Kong et al., Enzymatic Synthesis of Sequence-Defined Synthetic Nucleic Acid Polymers with Diverse Functional Groups. Angewandte Chemie Int. Ed. Sep. 16, 2016;55(42):13164-8.
Kong et al., Enzymatic Synthesis of Sequence-Defined Synthetic Nucleic Acid Polymers with Diverse Functional Groups, Supporting Information. Angewandte Chemie Int. Ed. Sep. 16, 2016;55(42):38 pages.
Kong et al., Generation of Synthetic Copolymer Libraries by Combinatorial Assembly on Nucleic Acid Templates. ACS Combinatorial Science. Jun. 8, 2016;18(7):355-70.
Kong et al., In Vitro Selection of Diversely Functionalize Aptamers. Journal of the American Chemical Society. Oct. 11, 2017;139(40):13977-80.
Kong et al., In Vitro Selection of Diversely Functionalize Aptamers, Supporting Information. Journal of the American Chemical Society. Oct. 11, 2017;139(40):36 pages.
Lambert et al., Molecular basis of PCSK9 function. Atherosclerosis. Mar. 2009;203(1):1-7. doi: 10.1016/j.atherosclerosis.2008.06.010. Epub Jun. 20, 2008.
Lei et al., A High-Fidelity Codon Set for the T4 DNA Ligase-Catalyzed Polymerization of Modified Oligonucleotides. ACS Combinatorial Science. Dec. 14, 2015;17(12):716-21.
Lei et al., A High-Fidelity Codon Set for the T4 DNA Ligase-Catalyzed Polymerization of Modified Oligonucleotides, Supporting Information. ACS Combinatorial Science. Dec. 14, 2015;17(12):34 pages.
Lei et al., Structure-activity relationships of the ATP cofactor in ligase-catalyzed oligonucleotide polymerisations. Organic & Biomolecular Chemistry. Mar. 21, 2017;15(11):2349-52.
Lei et al., Structure-activity relationships of the ATP cofactor in ligase-catalyzed oligonucleotide polymerisations, Supporting Information. Organic & Biomolecular Chemistry. Mar. 21, 2017;15(11):66 pages.
Lermer et al., Toward an RNaseA Mimic: A DNAzyme with Imidazoles and Cationic Amines. J. Am. Chem. Soc. Aug. 2002;124:9960-9961.
Lichtor et al., Side-chain determinants of biopolymer function during selection and replication. Nat. Chem. Biol. Apr. 2019;15(4):419-26.
Lichtor et al., Side-chain determinants of biopolymer function during selection and replication, Supporting Information. Nat. Chem. Biol. Apr. 2019;15(4):33 pages.
Lo Surdo et al., Mechanistic implications for LDL receptor degradation from the PCSK9/LDLR structure at neutral pH. EMBO Rep. Dec. 2011;12:1300-1305.
Martin, Cutadapt removes adapter sequences from high-throughput sequencing reads. EMBnet.journal. May 2011;17(1):10-12.
Mattheakis et al., An in vitro polysome display system for identifying ligands from very large peptide libraries. Proc Natl Acad Sci U S A. Sep. 13, 1994;91(19):9022-6. doi: 10.1073/pnas.91.19.9022.
Nemoto et al., In vitro virus: bonding of mRNA bearing puromycin at the 3'-terminal end to the C-terminal end of its encoded protein on the ribosome in vitro. FEBS Lett. Sep. 8, 1997;414(2):405-8. doi: 10.1016/s0014-5793(97)01026-0.
Ortigao et al., Antisense effect of oligodeoxynucleotides with inverted terminal internucleotidic linkages: a minimal modification protecting against nucleolytic degradation. Antisense Res Dev. Summer 1992;2(2):129-46. doi: 10.1089/ard.1992.2.129.
Perrin et al., Bridging the gap between proteins and nucleic acids: a metal-independent RNAseA mimic with two protein-like functionalities. J Am Chem Soc. Feb. 28, 2001;123(8):1556-63. doi: 10.1021/ja003290s.
Perrin et al., Expanding the catalytic repertoire of nucleic acid catalysts: simultaneous incorporation of two modified deoxyribonucleoside triphosphates bearing ammonium and imidazolyl functionalities. Nucleosides Nucleotides. Mar. 1999; 18(3): 377-39.
Pinheiro et al., The XNA world: progress towards replication and evolution of synthetic genetic polymers. Curr Opin Chem Biol. Aug. 2012;16(3-4):245-52. doi: 10.1016/j.cbpa.2012.05.198. Epub Jun. 14, 2012.
Pinheiro et al., Towards XNA nanotechnology: new materials from synthetic genetic polymers. Trends Biotechnol. Jun. 2014;32(6):321-8. doi: 10.1016/j.tibtech.2014.03.010. Epub Apr. 15, 2014.
Pinheiro et al., Synthetic genetic polymers capable of heredity and evolution. Science. Apr. 20, 2012;336(6079):341-4. doi: 10.1126/science.1217622.

(56) References Cited

OTHER PUBLICATIONS

Roberts et al., RNA-peptide fusions for the in vitro selection of peptides and proteins. Proc Natl Acad Sci U S A. Nov. 11, 1997;94(23):12297-302. doi: 10.1073/pnas.94.23.12297.

Robertson et al., Selection in vitro of an RNA enzyme that specifically cleaves single-stranded DNA. Nature. Mar. 29, 1990;344(6265):467-8. doi: 10.1038/344467a0.

Rogers et al., Discovering functional, non-proteinogenic amino acid containing, peptides using genetic code reprogramming. Org Biomol Chem. Sep. 28, 2015;13(36):9353-63. doi: 10.1039/c5ob01336d. Epub Aug. 17, 2015.

Santoro et al., RNA cleavage by a DNA enzyme with extended chemical functionality. J. Am. Chem. Soc. 2000; 122:2433-2439. Epub Mar. 4, 2000.

Sefah et al., In vitro selection with artificial expanded genetic information systems. Proc Natl Acad Sci U S A. Jan. 28, 2014;111(4):1449-54. doi: 10.1073/pnas.1311778111. Epub Dec. 30, 2013.

Shi et al., Recent advances on the encoding and selection methods of DNA-encoded chemical library. Bioorganic & Medicinal Chemistry Letters. Dec. 9, 2017;27(3):361-9.

Shoji et al., Modified DNA aptamer that binds the (R)-isomer of a thalidomide derivative with high enantioselectivity. J Am Chem Soc. Feb. 7, 2007;129(5):1456-64. doi: 10.1021/ja067098n.

Sidorov et al., Sequence-specific cleavage of RNA in the absence of divalent metal ions by a DNAzyme incorporating imidazolyl and amino functionalities. Nucleic Acids Res. Mar. 5, 2004;32(4):1591-601. doi: 10.1093/nar/gkh326. Print 2004.

Stein et al., Effect of a Monoclonal Antibody to PCSK9 on LDL Cholesterol. N. Engl. J. Med. Mar. 2012;366:1108-1118.

Taylor et al., Catalysts from synthetic genetic polymers. Nature. Feb. 19, 2015;518(7539):427-30. doi: 10.1038/nature13982. Epub Dec. 1, 2014.

Tolle et al., A Versatile Approach Towards Nucleobase-Modifted Aptamers. Angew Chem Int Ed Engl. Sep. 7, 2015;54(37):10971-4. doi: 10.1002/anie.201503652. Epub Jul. 23, 2015.

Tuerk et al., Systematic evolution of ligands by exponential enrichment: RNA ligands to bacteriophage T4 DNA polymerase. Science. Aug. 3, 1990;249(4968):505-10. doi: 10.1126/science.2200121.

Vaught et al., Expanding the chemistry of DNA for in vitro selection. J Am Chem Soc. Mar. 31, 2010;132(12):4141-51. doi: 10.1021/ja908035g.

Yamaguchi et al., cDNA display: a novel screening method for functional disulfiderich peptides by solid-phase synthesis and stabilization of mRNA-protein fusions. Nucleic Acids Res. Sep. 2009;37(16):e108. doi: 10.1093/nar/gkp514. Epub Jun. 15, 2009. 13 pages.

Yu et al., Darwinian evolution of an alternative genetic system provides support for TNA as an RNA progenitor. Nat. Chem. Mar. 2012; 4:183-187.

Zhang et al., Evolution of functional six-nucleotide DNA. J Am Chem Soc. Jun. 3, 2015;137(21):6734-7. doi: 10.1021/jacs.5b02251. Epub May 20, 2015.

Zuker, Mfold web server for nucleic acid folding and hybridization prediction. Nucleic Acids Res. Jul. 2003;31:3406-3415.

PCT/US2018/041127, Oct. 19, 2018, International Search Report and Written Opinion.

PCT/US2018/041127, Jan. 16, 2020, International Preliminary Report on Patentability.

\* cited by examiner

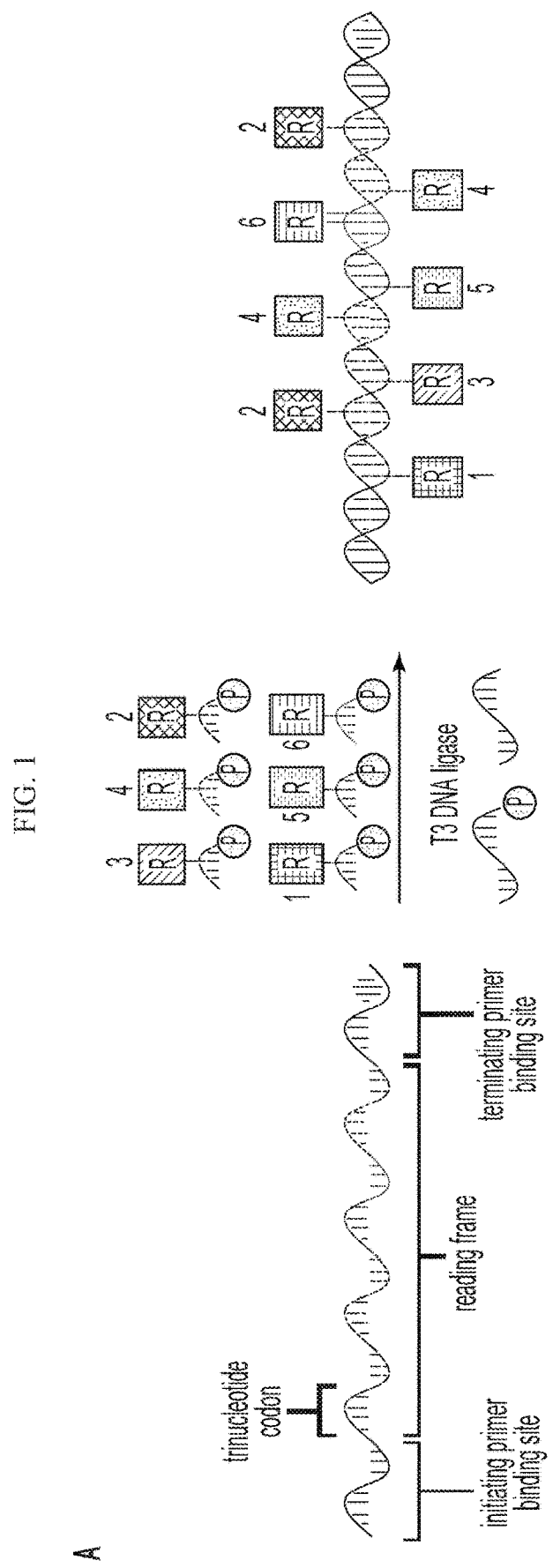

FIG. 2
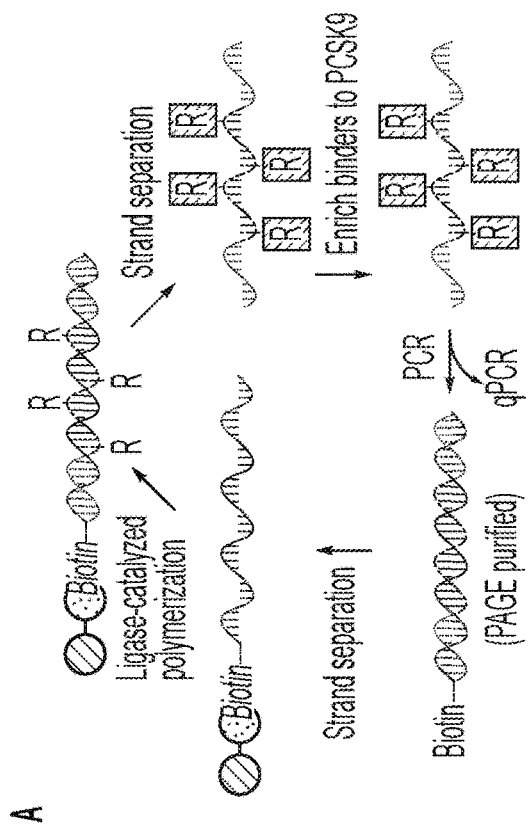
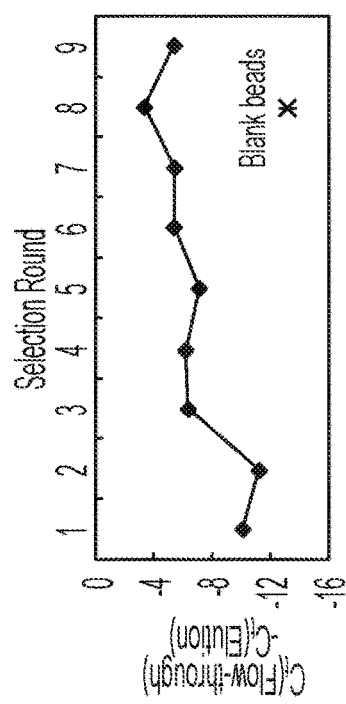

FIG. 3 continued
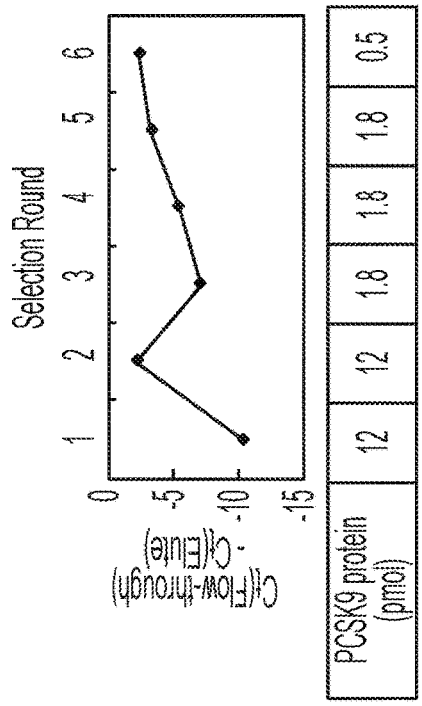
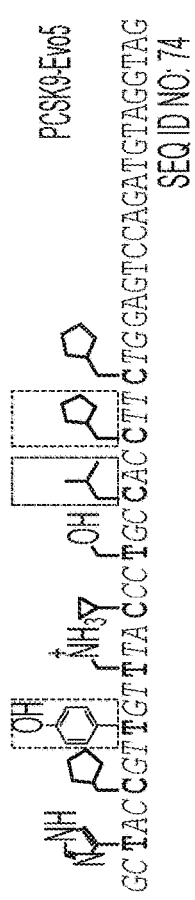

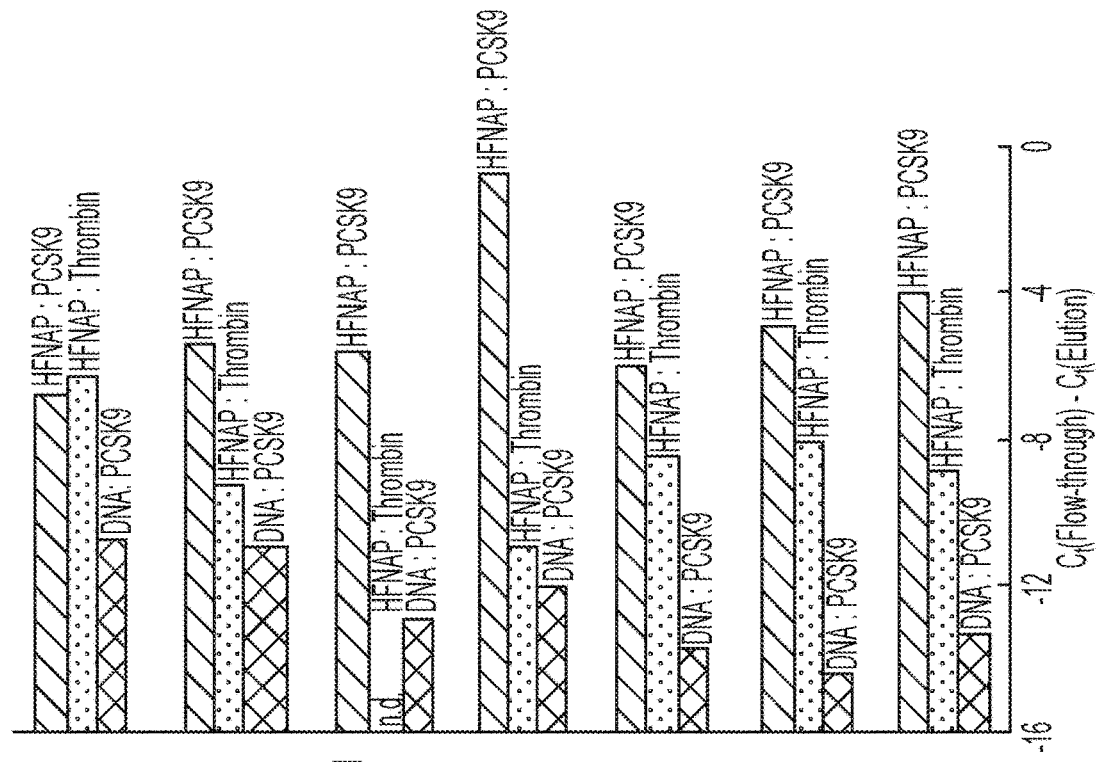
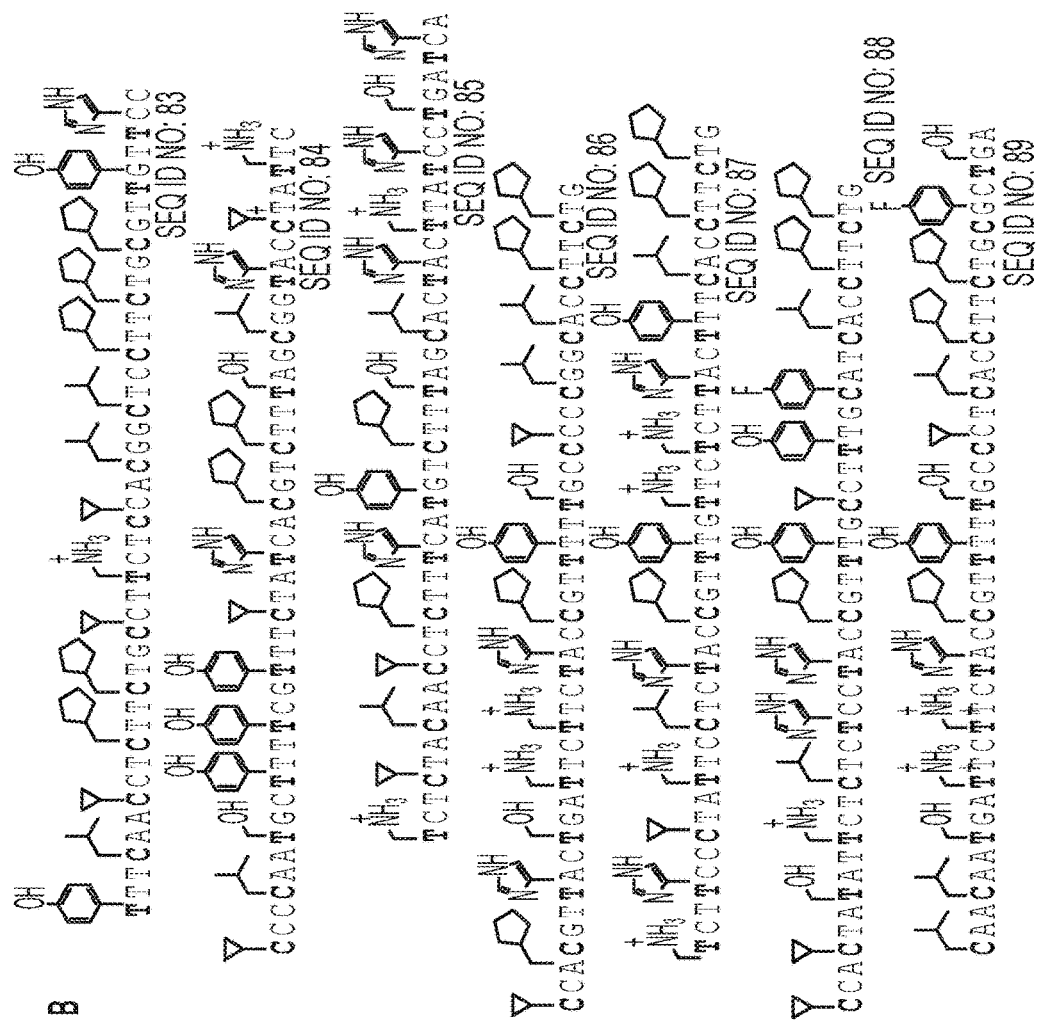
FIG. 5 continued

SEQUENCE LISTING

<160> NUMBER OF SEQ ID NOS: 97

<210> SEQ ID NO 1
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 1
cgtacggtcg acgctagcnn rnnrnnrnnr nnrnnrnnrn nrnnrnnrnn rcacgtggag      60
ctcggatcc                                                              69

<210> SEQ ID NO 2
<211> LENGTH: 75
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

```
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t

<400> SEQUENCE: 2
cgtacggtcg acgctagcnn rnnrnnrnnr nnrnnrnnrn nrnnrnnrnn rnnrnnrcac      60
gtggagctcg gatcc                                                      75

<210> SEQ ID NO 3
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
```

```
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 3
cgtacggtcg acgctagcnn rnnrnnrnnr nnrnnrnnrn nrnnrnnrnn rnnrnnrnnr    60
nnrcacgtgg agctcggatc c                                              81

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation

<400> SEQUENCE: 4
gctagcgtcg accgtacg                                                  18

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 5
ggatccgagc tccacgtg                                                  18

<210> SEQ ID NO 6
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (1)..(1)
<223> OTHER INFORMATION: Modified by 5' dual biotin and int spacer 18

<400> SEQUENCE: 6
cgtacggtcg acgctagctt gaaagtgcaa gagacaccgc gacacgtgga gctcggatcc    60

<210> SEQ ID NO 7
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 7
cgtacggtcg acgctagcat gttactggta tcgtgagcgg gacacgtgga gctcggatcc    60

<210> SEQ ID NO 8
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 8
cgtacggtcg acgctagcta gatatggcta gggtcaaggg cacacgtgga gctcggatcc    60

<210> SEQ ID NO 9
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 9
cgtacggtcg acgctagcaa gtaacaggaa acgagacggc cacacgtgga gctcggaucc    60

<210> SEQ ID NO 10
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation

<400> SEQUENCE: 10
gctagcgtcg accgtacgag cgtcgctacg cgtgac                              36

<210> SEQ ID NO 11
<211> LENGTH: 18
<212> TYPE: DNA
<213> ORGANISM: Artificial Sequence
<220> FEATURE:
<223> OTHER INFORMATION: Synthetic polynucleotide
```

<400> SEQUENCE: 11
ggatccgagc tccacgtg                                                  18

<210> SEQ ID NO 12
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 12
taatacgact cactataggg ctcgatttaa tttcgccgac gtgatgacat tccaggcagt     60
gtcacgcgta gcgacgct                                                  78

<210> SEQ ID NO 13
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t

<400> SEQUENCE: 13
cgaatcagat tggaccagyn nynnynnynn ynnynnynny nnynnynnyn nynnynnynn    60
ynngagtcca gatgtaggta g                                              81

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 14
ctacctacat ctggactc                                                  18

<210> SEQ ID NO 15
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 15
ctacctacat ctggactc                                                  18

<210> SEQ ID NO 16
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation

<400> SEQUENCE: 16
gagtccagat gtaggtag                                                  18

<210> SEQ ID NO 17
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 17
cgaatcagat tggaccag                                                  18

<210> SEQ ID NO 18
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(37)

<223> OTHER INFORMATION: n is a, c, g, or t

<400> SEQUENCE: 18
acactctttc cctacacgac gctcttccga tctnnnncta cctacatctg gactc         55

<210> SEQ ID NO 19
<211> LENGTH: 51
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(33)
<223> OTHER INFORMATION: n is a, c, g, or t

<400> SEQUENCE: 19
tggagttcag acgtgtgctc ttccgatctn nnncgaatca gattggacca g            51

<210> SEQ ID NO 20
<211> LENGTH: 49
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (29)..(30)
<223> OTHER INFORMATION: Modified by 8-base barcode

<400> SEQUENCE: 20
aatgatacgg cgaccaccga gatctacaca cactctttcc ctacacgac              49

<210> SEQ ID NO 21
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(25)
<223> OTHER INFORMATION: Modified by 8-base barcode

<400> SEQUENCE: 21
caagcagaag acggcatacg agatgtgact ggagttcaga cgtgtgct               48

<210> SEQ ID NO 22
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(19)
<223> OTHER INFORMATION: n is 79% dC and 21% T
<220> FEATURE:
<221> NAME/KEY: misc_feature
<222> LOCATION: (20)..(20)
<223> OTHER INFORMATION: n is 7% dA, 79% dC, 7% dG, and 7% T
<220> FEATURE:
<221> NAME/KEY: misc_feature
<222> LOCATION: (21)..(21)
<223> OTHER INFORMATION: n is 79% dA, 7% dC, 7% dG, and 7% T
<220> FEATURE:
<221> NAME/KEY: misc_feature
<222> LOCATION: (22)..(22)
<223> OTHER INFORMATION: n is 79% dC and 21% T
<220> FEATURE:
<221> NAME/KEY: misc_feature

```
<222> LOCATION: (23)..(23)
<223> OTHER INFORMATION: n is 7% dA, 7% dC, 79% dG, and 7% T
<220> FEATURE:
<221> NAME/KEY: misc_feature
<222> LOCATION: (24)..(24)
<223> OTHER INFORMATION: n is 7% dA, 7% dC, 7% dG, and 79% T
<220> FEATURE:
<221> NAME/KEY: misc_feature
<222> LOCATION: (25)..(25)
<223> OTHER INFORMATION: n is 21% dC and 79% T
<220> FEATURE:
<221> NAME/KEY: misc_feature
<222> LOCATION: (26)..(26)
<223> OTHER INFORMATION: n is 79% dA, 7% dC, 7% dG, and 7% T
<220> FEATURE:
<221> NAME/KEY: misc_feature
<222> LOCATION: (27)..(27)
<223> OTHER INFORMATION: n is 7% dA, 79% dC, 7% dG, and 7% T
<220> FEATURE:
<221> NAME/KEY: misc_feature
<222> LOCATION: (28)..(28)
<223> OTHER INFORMATION: n is 21% dC and 79% T
<220> FEATURE:
<221> NAME/KEY: misc_feature
<222> LOCATION: (29)..(29)
<223> OTHER INFORMATION: n is 7% dA, 7% dC, 79% dG, and 7% T
<220> FEATURE:
<221> NAME/KEY: misc_feature
<222> LOCATION: (30)..(30)
<223> OTHER INFORMATION: n is 79% dA, 7% dC, 7% dG, and 7% T
<220> FEATURE:
<221> NAME/KEY: misc_feature
<222> LOCATION: (31)..(31)
<223> OTHER INFORMATION: n is 21% dC and 79% T
<220> FEATURE:
<221> NAME/KEY: misc_feature
<222> LOCATION: (32)..(32)
<223> OTHER INFORMATION: n is 7% dA, 7% dC, 7% dG, and 79% T
<220> FEATURE:
<221> NAME/KEY: misc_feature
<222> LOCATION: (33)..(33)
<223> OTHER INFORMATION: n is 7% dA, 79% dC, 7% dG, and 7% T
<220> FEATURE:
<221> NAME/KEY: misc_feature
<222> LOCATION: (34)..(34)
<223> OTHER INFORMATION: n is 21% dC and 79% T
<220> FEATURE:
<221> NAME/KEY: misc_feature
<222> LOCATION: (35)..(35)
<223> OTHER INFORMATION: n is 7% dA, 7% dC, 7% dG, and 79% T
<220> FEATURE:
<221> NAME/KEY: misc_feature
<222> LOCATION: (36)..(36)
<223> OTHER INFORMATION: n is 7% dA, 79% dC, 7% dG, and 7% T
<220> FEATURE:
<221> NAME/KEY: misc_feature
<222> LOCATION: (37)..(37)
<223> OTHER INFORMATION: n is 21% dC and 79% T
<220> FEATURE:
<221> NAME/KEY: misc_feature
<222> LOCATION: (38)..(38)
<223> OTHER INFORMATION: n is 79% dA, 7% dC, 7% dG, and 7% T
<220> FEATURE:
<221> NAME/KEY: misc_feature
<222> LOCATION: (39)..(39)
<223> OTHER INFORMATION: n is 7% dA, 79% dC, 7% dG, and 7% T
<220> FEATURE:
<221> NAME/KEY: misc_feature
<222> LOCATION: (40)..(40)
<223> OTHER INFORMATION: n is 79% dC and 21% T
<220> FEATURE:
<221> NAME/KEY: misc_feature
<222> LOCATION: (41)..(41)
<223> OTHER INFORMATION: n is 7% dA, 7% dC, 79% dG, and 7% T
<220> FEATURE:
<221> NAME/KEY: misc_feature
<222> LOCATION: (42)..(42)
<223> OTHER INFORMATION: n is 7% dA, 7% dC, 7% dG, and 79% T
<220> FEATURE:
```

```
<221> NAME/KEY: misc_feature
<222> LOCATION: (43)..(43)
<223> OTHER INFORMATION: n is 21% dC and 79% T
<220> FEATURE:
<221> NAME/KEY: misc_feature
<222> LOCATION: (44)..(45)
<223> OTHER INFORMATION: n is 7% dA, 7% dC, 7% dG, and 79% T
<220> FEATURE:
<221> NAME/KEY: misc_feature
<222> LOCATION: (46)..(46)
<223> OTHER INFORMATION: n is 21% dC and 79% T
<220> FEATURE:
<221> NAME/KEY: misc_feature
<222> LOCATION: (47)..(47)
<223> OTHER INFORMATION: n is 7% dA, 7% dC, 79% dG, and 7% T
<220> FEATURE:
<221> NAME/KEY: misc_feature
<222> LOCATION: (48)..(48)
<223> OTHER INFORMATION: n is 7% dA, 79% dC, 7% dG, and 7% T
<220> FEATURE:
<221> NAME/KEY: misc_feature
<222> LOCATION: (49)..(49)
<223> OTHER INFORMATION: n is 79% dC and 21% T
<220> FEATURE:
<221> NAME/KEY: misc_feature
<222> LOCATION: (50)..(51)
<223> OTHER INFORMATION: n is 7% dA, 79% dC, 7% dG, and 7% T
<220> FEATURE:
<221> NAME/KEY: misc_feature
<222> LOCATION: (52)..(52)
<223> OTHER INFORMATION: n is 79% dC and 21% T
<220> FEATURE:
<221> NAME/KEY: misc_feature
<222> LOCATION: (53)..(54)
<223> OTHER INFORMATION: n is 7% dA, 7% dC, 79% dG, and 7% T
<220> FEATURE:
<221> NAME/KEY: misc_feature
<222> LOCATION: (55)..(55)
<223> OTHER INFORMATION: n is 79% dC and 21% T
<220> FEATURE:
<221> NAME/KEY: misc_feature
<222> LOCATION: (56)..(56)
<223> OTHER INFORMATION: n is 79% dA, 7% dC, 7% dG, and 7% T
<220> FEATURE:
<221> NAME/KEY: misc_feature
<222> LOCATION: (57)..(57)
<223> OTHER INFORMATION: n is 7% dA, 79% dC, 7% dG, and 7% T
<220> FEATURE:
<221> NAME/KEY: misc_feature
<222> LOCATION: (58)..(58)
<223> OTHER INFORMATION: n is 79% dC and 21% T
<220> FEATURE:
<221> NAME/KEY: misc_feature
<222> LOCATION: (59)..(60)
<223> OTHER INFORMATION: n is 7% dA, 7% dC, 7% dG, and 79% T
<220> FEATURE:
<221> NAME/KEY: misc_feature
<222> LOCATION: (61)..(61)
<223> OTHER INFORMATION: n is 79% dC and 21% T
<220> FEATURE:
<221> NAME/KEY: misc_feature
<222> LOCATION: (62)..(62)
<223> OTHER INFORMATION: n is 7% dA, 7% dC, 7% dG, and 79% T
<220> FEATURE:
<221> NAME/KEY: misc_feature
<222> LOCATION: (63)..(63)
<223> OTHER INFORMATION: n is 7% dA, 7% dC, 79% dG, and 7% T

<400> SEQUENCE: 22
cgaatcagat tggaccagnn nnnnnnnnnn nnnnnnnnnn nnnnnnnnnn nnnnnnnnnn      60
nnngagtcca gatgtaggta g                                                81

<210> SEQ ID NO 23
<211> LENGTH: 18
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation
<220> FEATURE:
<221> NAME/KEY: misc_feature
<222> LOCATION: (18)..(18)
<223> OTHER INFORMATION: Modified by 3' dideoxy-C

<400> SEQUENCE: 23
gagtccagat gtaggtag                                                  18

<210> SEQ ID NO 24
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 24
ctacctacat ctggactcca gaaggtgatg caaaggcaaa cggtaggaga gagaatatag    60
tggctggtcc aatctgattc g                                              81

<210> SEQ ID NO 25
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 25
cgaatcagat tggaccagcc actatattct ctctcctacc gtttgccttt gcatcacctt    60
ctggagtcca gatgtaggta g                                              81

<210> SEQ ID NO 26
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 26
ctacctacat ctggactctc agcgcagaag gtgagggcaa aaacggtaga agaatcattg    60
ttgctggtcc aatctgattc g                                              81

<210> SEQ ID NO 27
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 27
cgaatcagat tggaccagca acaatgattc ttctaccgtt tttgccctca ccttctgcgc    60
tgagagtcca gatgtaggta g                                              81
```

<210> SEQ ID NO 28
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 28
ctacctacat ctggactctg atcaggataa gtagtgctaa agacatgaaa gaggttgtag    60
agactggtcc aatctgattc g                                              81

<210> SEQ ID NO 29
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 29
cgaatcagat tggaccagtc tctacaacct ctttcatgtc tttagcacta cttatcctga    60
tcagagtcca gatgtaggta g                                              81

<210> SEQ ID NO 30
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 30
ctacctacat ctggactcga ataggtaccg ctaaagacgt gatagaaacg aaaagcattg    60
gggctggtcc aatctgattc g                                              81

<210> SEQ ID NO 31
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 31
cgaatcagat tggaccagcc ccaatgcttt tcgtttctat cacgtcttta gcggtaccta    60
ttcgagtcca gatgtaggta g                                              81

<210> SEQ ID NO 32
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 32
ctacctacat ctggactcca gaaggtgccg ggggcaaaaa cggtagaaga atcagtaacg    60

```
tggctggtcc aatctgattc g                                               81
```

<210> SEQ ID NO 33
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 33

```
cgaatcagat tggaccagcc acgttactga ttcttctacc gttttttgccc ccggcacctt   60 ctggagtcca gatgtaggta g                                               81
```

<210> SEQ ID NO 34
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 34

```
ctacctacat ctggactcgg aacaacgcag aaggagccgt ggagaaggca gaagaggttg   60
aaactggtcc aatctgattc g                                               81
```

<210> SEQ ID NO 35
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 35

```
cgaatcagat tggaccagtt tcaacctctt ctgccttctc cacggctcct tctgcgttgt   60
tccgagtcca gatgtaggta g                                               81
```

<210> SEQ ID NO 36
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 36

```
ctacctacat ctggactcca gaaggtgaaa gtaagagaac aaacggtaga ggaataggga   60
agactggtcc aatctgattc g                                               81
```

<210> SEQ ID NO 37
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 37

```
cgaatcagat tggaccagtc ttccctattc ctctaccgtt tgttctctta ctttcacctt   60
```
ctggagtcca gatgtaggta g                                                  81

<210> SEQ ID NO 38
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 38
cgaatcagat tggaccag                                                      18

<210> SEQ ID NO 39
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 39
ctacctacat ctggactcca gaaggtgccg ggggcaaaaa cggtagaaga atcagtaacg         60
tggctggtcc aatctgattc g                                                  81

<210> SEQ ID NO 40
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation
<220> FEATURE:
<221> NAME/KEY: misc_feature
<222> LOCATION: (18)..(18)
<223> OTHER INFORMATION: Modified by 5' dual biotin, int spacer 18, and
      3' dideoxy-C

<400> SEQUENCE: 40
gagtccagat gtaggtag                                                      18

<210> SEQ ID NO 41
<211> LENGTH: 14
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation
<220> FEATURE:
<221> NAME/KEY: misc_feature
<222> LOCATION: (14)..(14)
<223> OTHER INFORMATION: Modified by 5' dual biotin, int spacer 18, and
      3' dideoxy-C

<400> SEQUENCE: 41
gagtccagat gtag                                                          14

<210> SEQ ID NO 42
<211> LENGTH: 18
<212> TYPE: DNA
<213> ORGANISM: Artificial Sequence

```
<220> FEATURE:
<223> OTHER INFORMATION: Synthetic polynucleotide

<400> SEQUENCE: 42
ccacgttact gattcugc                                                 18

<210> SEQ ID NO 43
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 43
ctacctacat ctggactcca gaaggtggca gggtaaacaa cggtagcaga atcagtaacg   60
tgg                                                                 63

<210> SEQ ID NO 44
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation
<220> FEATURE:
<221> NAME/KEY: misc_feature
<222> LOCATION: (18)..(18)
<223> OTHER INFORMATION: Modified by int spacer 18 and 3' AlexF647N

<400> SEQUENCE: 44
gagtccagat gtaggtag                                                 18

<210> SEQ ID NO 45
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 45
tgctaccgtt gtttaccctg ccaccttctg                                    30

<210> SEQ ID NO 46
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 46
ctacctacat ctggactcca gaaggtggca gggtaaacaa cggtagcaga atcagtaacg   60
tggctg                                                              66

<210> SEQ ID NO 47
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (48)..(48)
<223> OTHER INFORMATION: Modified by 3' inverted dT

<400> SEQUENCE: 47
tgctaccgtt gtttaccctg ccaccttctg gagtccagat gtaggtag                    48

<210> SEQ ID NO 48
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t

<400> SEQUENCE: 48
ctcggatgaa cctggactyn nynnynnynn ynnynnynny nnynnynnyn nynnynnynn        60
```
ynnggactga gtccagagta a        81

<210> SEQ ID NO 49
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 49
ttactctgga ctcagtcc        18

<210> SEQ ID NO 50
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 50
ttactctgga ctcagtcc        18

<210> SEQ ID NO 51
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation

<400> SEQUENCE: 51
ggactgagtc cagagtaa        18

<210> SEQ ID NO 52
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 52
ctcggatgaa cctggact        18

<210> SEQ ID NO 53
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(39)
<223> OTHER INFORMATION: n is a, c, g, or t

<400> SEQUENCE: 53
acactctttc cctacacgac gctcttccga tctnnnnnnt tactctggac tcagtcc        57

<210> SEQ ID NO 54
<211> LENGTH: 51
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(33)
<223> OTHER INFORMATION: n is a, c, g, or t

<400> SEQUENCE: 54
tggagttcag acgtgtgctc ttccgatctn nnnctcggat gaacctggac t          51

<210> SEQ ID NO 55
<211> LENGTH: 49
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (29)..(30)
<223> OTHER INFORMATION: Modified by 8-base barcode

<400> SEQUENCE: 55
aatgatacgg cgaccaccga gatctacaca cactctttcc ctacacgac             49

<210> SEQ ID NO 56
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(25)
<223> OTHER INFORMATION: Modified by 8-base barcode

<400> SEQUENCE: 56
caagcagaag acggcatacg agatgtgact ggagttcaga cgtgtgct              48

<210> SEQ ID NO 57
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 57
ttactctgga ctcagtcctg gtggccactg gcagcaccgt cacggaggct gagactgccg 60
caaagtccag gttcatccga g                                          81

<210> SEQ ID NO 58
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 58
ttactctgga ctcagtccac aggagggata ccggaagggc aaaggccgta gccagaacaa 60
aaaagtccag gttcatccga g                                          81
```

<210> SEQ ID NO 59
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 59
ttactctgga ctcagtccac aacgcagccg gaagcaccac aggagaggcg gtaaccagca        60
acaagtccag gttcatccga g                                                 81

<210> SEQ ID NO 60
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 60
ttactctgga ctcagtcctc ggaagcgtca cgacggtaac cggcactgag agcaacacca        60
caaagtccag gttcatccga g                                                 81

<210> SEQ ID NO 61
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 61
ttactctgga ctcagtcctg gctaaggcga ccacgggcac tgcaaccaca gccaaagggg        60
tgaagtccag gttcatccga g                                                 81

<210> SEQ ID NO 62
<211> LENGTH: 81
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 62
ttactctgga ctcagtccca atgagggaga gaggggaag ggcgacaaag gccgtaacca         60
ggaagtccag gttcatccga g                                                 81

<210> SEQ ID NO 63
<211> LENGTH: 81
<212> TYPE: DNA
<213> ORGANISM: Artificial Sequence
<220> FEATURE:

```
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 63
ttactctgga ctcagtcccc ggaggaatga gtacgaggaa gggcaacgaa ataaacagca    60
gcaagtccag gttcatccga g                                              81

<210> SEQ ID NO 64
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' phosphorylation
<220> FEATURE:
<221> NAME/KEY: misc_feature
<222> LOCATION: (18)..(18)
<223> OTHER INFORMATION: Modified by 3' dideoxy-C

<400> SEQUENCE: 64
ggactgagtc cagagtaa                                                  18

<210> SEQ ID NO 65
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by 5' dual biotin and int spacer 18

<400> SEQUENCE: 65
ctcggatgaa cctggact                                                  18

<210> SEQ ID NO 66
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 66
ttactctgga ctcagtcccc ggaggaatga gtacgaggaa gggcaacgaa ataaacagca    60
gcaagtccag gttcatccga g                                              81

<210> SEQ ID NO 67
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 67
ccacgttact gattcttcta ccgttttttgc ccccggcacc ttctg                   45

<210> SEQ ID NO 68
<211> LENGTH: 45
<212> TYPE: DNA
<213> ORGANISM: Artificial Sequence
```

```
<220> FEATURE:
<223> OTHER INFORMATION: Synthetic polynucleotide

<400> SEQUENCE: 68
tgctgctgtt tatttcgttg cccttcctcg tactcattcc tccgg            45

<210> SEQ ID NO 69
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 69
ttgaaagtgc aagagacacc gcga                                   24

<210> SEQ ID NO 70
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 70
atgttactgg tatcgtgagc ggga                                   24

<210> SEQ ID NO 71
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 71
tagatatggc tagggtcaag ggca                                   24

<210> SEQ ID NO 72
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 72
aagtaacagg aaacgagacg gcca                                   24

<210> SEQ ID NO 73
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 73
cgaatcagat tggaccagcc acgttactga ttcttctacc gttttttgccc ccggcacctt    60 ctggagtcca gatgtaggta g                                              81

<210> SEQ ID NO 74
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 74
```
gctaccgttg tttaccctgc caccttctgg agtccagatc taggtag       47

<210> SEQ ID NO 75
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 75
ttgcggcagt ctcagcctcc gtgacggtgc tgccagtggc cacca       45

<210> SEQ ID NO 76
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 76
tttttgttct ggctacggcc tttgcccttc cggtatccct cctgt       45

<210> SEQ ID NO 77
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 77
tgttgctggt taccgcctct cctgtggtgc ttccggctgc gttgt       45

<210> SEQ ID NO 78
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 78
ttgtggtgtt gctctcagtg ccggttaccg tcgtgacgct tccga       45

<210> SEQ ID NO 79
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 79
tcaccccttt ggctgtggtt gcagtgcccg tggtcgcctt agcca       45

<210> SEQ ID NO 80
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 80
tcctggttac ggcctttgtc gcccttcccc ctctctccct cattg       45

<210> SEQ ID NO 81
<211> LENGTH: 45
<212> TYPE: DNA
<213> ORGANISM: Artificial Sequence

```
<220> FEATURE:
<223> OTHER INFORMATION: Synthetic polynucleotide

<400> SEQUENCE: 81
tgctgctgtt tatttcgttg cccttcctcg tactcattcc tccgg            45

<210> SEQ ID NO 82
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 82
ctcggatgaa cctggacttg ctgctgttta tttcgttgcc cttcctcgta ctcattcctc    60
cggggactga gtccagagta a                                              81

<210> SEQ ID NO 83
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 83
tttcaacctc ttctgccttc tccacggctc cttctgcgtt gttcc            45

<210> SEQ ID NO 84
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 84
ccccaatgct tttcgtttct atcacgtctt tagcggtacc tattc            45

<210> SEQ ID NO 85
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 85
tctctacaac ctctttcatg tctttagcac tacttatcct gatca            45

<210> SEQ ID NO 86
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 86
ccacgttact gattcttcta ccgtttttgc ccccggcacc ttctg            45

<210> SEQ ID NO 87
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 87
```
tcttccctat tcctctaccg tttgttctct tactttcacc ttctg    45

<210> SEQ ID NO 88
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 88
ccactatatt ctctctccta ccgtttgcct ttgcatcacc ttctg    45

<210> SEQ ID NO 89
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 89
caacaatgat tcttctaccg tttttgccct caccttctgc gctga    45

<210> SEQ ID NO 90
<211> LENGTH: 81
<212> TYPE: DNA
<213> ORGANISM: Artificial Sequence
<220> FEATURE:
<223> OTHER INFORMATION: Synthetic polynucleotide

<400> SEQUENCE: 90
cgaatcagat tggaccagcc acgttactga ttcttctacc gttttgcccc cggcaccttt    60
ctggagtcca gatgtaggta g    81

<210> SEQ ID NO 91
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 91
tcttctaccg tttttgcccc cggcaccttc tggagtccag atgtaggtag    50

<210> SEQ ID NO 92
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 92
gctaccgttg tttaccctgc caccttctgg agtccagatg taggtag    47

<210> SEQ ID NO 93
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 93
tctgctaccg ttgtttaccc tgccaccttc tggagtccag atgtag    46

<210> SEQ ID NO 94
<211> LENGTH: 48

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by C8F17-DMT
<220> FEATURE:
<221> NAME/KEY: misc_feature
<222> LOCATION: (48)..(48)
<223> OTHER INFORMATION: Modified by InvT

<400> SEQUENCE: 94
tgctaccgtt gtttaccctg ccaccttctg gagtccagat gtaggtag                 48

<210> SEQ ID NO 95
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by C8F17-DMT
<220> FEATURE:
<221> NAME/KEY: misc_feature
<222> LOCATION: (48)..(48)
<223> OTHER INFORMATION: Modified by InvT

<400> SEQUENCE: 95
tgctaccgtt gtttaccctg ccaccttctg gagtccagat gtaggtag                 48

<210> SEQ ID NO 96
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Modified by C8F17-DMT
<220> FEATURE:
<221> NAME/KEY: misc_feature
<222> LOCATION: (48)..(48)
<223> OTHER INFORMATION: Modified by InvT

<400> SEQUENCE: 96
tgctaccgtt gtttaccctg ccaccttctg gagtccagat gtaggtag                 48

<210> SEQ ID NO 97
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (48)..(48)
<223> OTHER INFORMATION: Modified by InvT

<400> SEQUENCE: 97
tgctaccgtt gtttaccctg ccaccttctg gagtccagat gtaggtag                 48
```

EVOLUTION OF BIOACTIVE SEQUENCE-DEFINED SYNTHETIC POLYMERS USING DNA-TEMPLATED POLYMERIZATION

RELATED APPLICATIONS

This application is a national stage filing under 35 U.S.C. § 371 of international PCT application, PCT/US2018/041127, filed Jul. 6, 2018, which claims priority under 35 U.S.C. § 119(e) to U.S. Provisional Application, U.S. Ser. No. 62/638,901, filed on Mar. 5, 2018, and to U.S. Provisional Application, U.S. Ser. No. 62/529,787, filed on Jul. 7, 2017, each of which is incorporated herein by reference.

GOVERNMENT SUPPORT

This invention was made with government support under grant numbers N66001-14-2-4053 awarded by the Department of Defense, and GM118062 and GM065865 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jan. 6, 2020, is named H082470267US02-SEQ-WWZ and is 36,010 bytes in size.

BACKGROUND OF INVENTION

Polymerases and ribosomes impose structural requirements on the building blocks that can be polymerized and thereby limit the diversity of synthetic polymers that are accessible to directed evolution. Accordingly, there remains a need for efficient and effective methodologies that allow for the generation of modified nucleic acid based polymers to create chemically diverse sequence-defined highly functionalized nucleic acid based polymers.

BRIEF SUMMARY OF INVENTION

Using a test-tube translation and Darwinian selection system, sequence-defined synthetic polymers containing many chosen side-chains were evolved that bind proteins of biomedical interest. The evolution of sequence-defined synthetic polymers made of building blocks beyond those compatible with polymerase enzymes or the ribosome has the potential to generate new classes of receptors, catalysts, and materials. A ligase-mediated DNA-templated polymerization system and in vitro selection was used to evolve highly functionalized nucleic acid polymers (HFNAPs) made from 32 building blocks containing eight chemically diverse side-chains on a DNA backbone. Through iterated cycles of polymer translation, selection, and reverse translation, HFNAPs that bind PCSK9 and IL-6, two protein targets implicated in human diseases were discovered. Mutation and reselection of an active PCSK9-binding polymer yielded evolved polymers with high affinity ($K_D$=3 nM). This evolved polymer potently inhibited binding between PCSK9 and the LDL receptor. Structure-activity relationship studies revealed that specific side-chains at defined positions in the polymers are required for binding to their respective targets. The findings expand the chemical space of evolvable polymers to include densely functionalized nucleic acids with diverse, researcher-defined chemical repertoires. It should be appreciated that the disclosure provides modified nucleic acid bases, for example any of the modified cytosine and thymine bases provided herein.

EXAMPLES

Some aspects of the disclosure are based at least in part on the surprising discovery that modified tri-nucleotide polymers may be assembled using nucleic acid chemistry to evolve sequence-defined highly functionalized nucleic acid polymers that are capable of binding proteins (e.g., PCSK9 and IL-6) that are implicated in human diseases.

The gene-encoded synthesis and Darwinian selection of sequence-defined biopolymers are fundamental features of all known forms of life. These processes have been harnessed in the laboratory to evolve RNA (1-3), DNA (4-6), and polypeptides (7-10) with a variety of binding and catalytic properties through iterated cycles of biopolymer translation, selection, replication, and mutation. The speed and effectiveness of the evolutionary process has inspired efforts to apply these principles to the much larger chemical space of synthetic polymers (11). To date, however, the evolution of sequence-defined non-natural polymers in the laboratory has been limited to analogs of nucleic acids (12-15) and polypeptides (16) that can be synthesized by polymerases and ribosomes. Polymerases and ribosomes impose structural requirements on the building blocks that can be polymerized and thereby limit the diversity of synthetic polymers that are accessible to directed evolution. For example, polymerases use only mononucleotides as substrates, precluding the ability to encode a diverse set of codons and side chains. Known classes of polymerase-synthesized functional non-natural nucleic acid polymers, including those derived from non-natural sugar backbones (17-20), uniform installation of hydrophobic (21-28) or positively charged (29-35) side-chains on nucleobases, or introduction of novel nucleobases among the four possibilities (36-38), therefore have chemical diversities that are only modestly expanded beyond those of natural DNA and RNA, and fall short of the much more diverse chemical functionality present in proteins.

Figure 1:
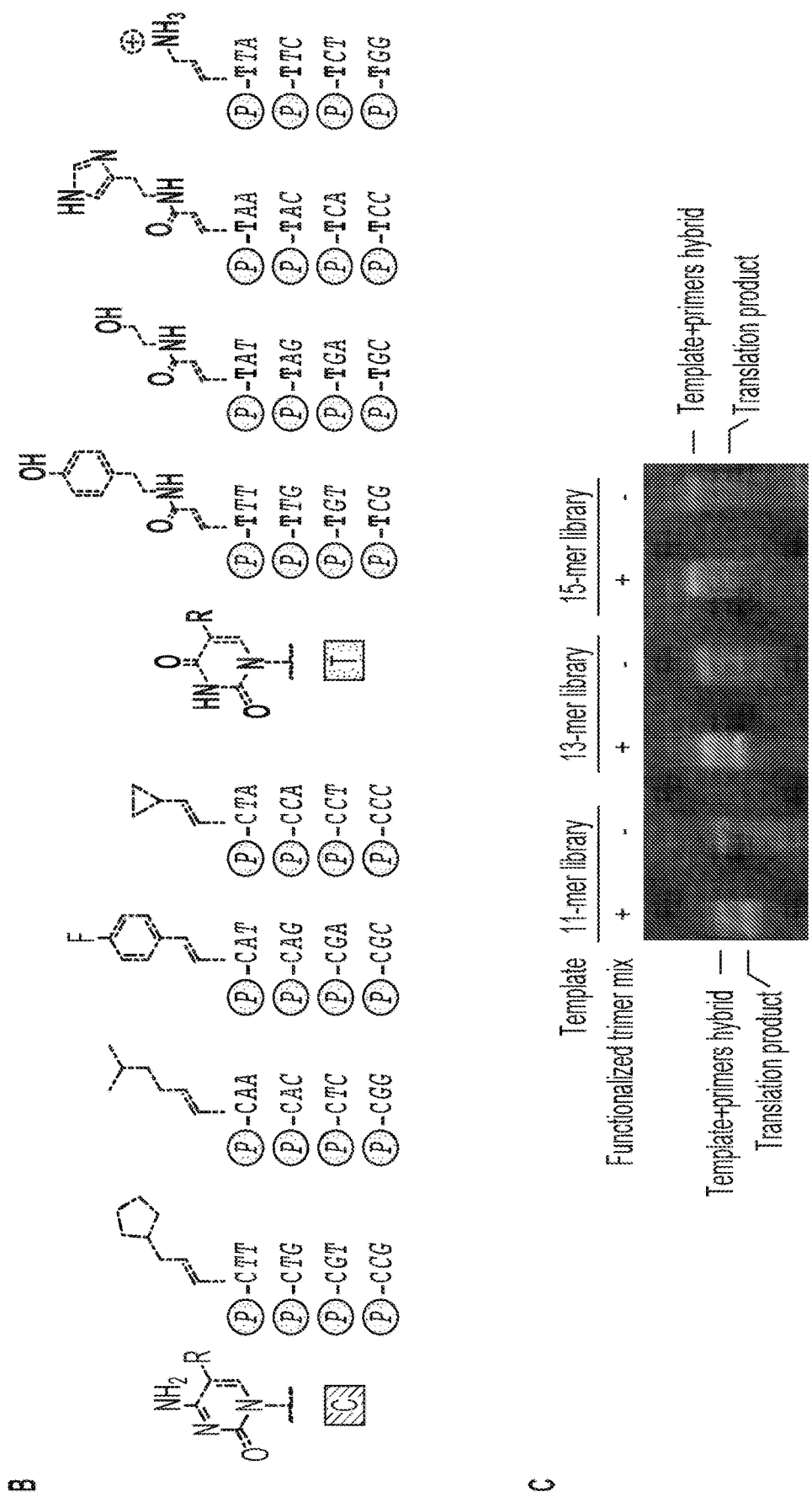
FIG. 1. Shows design and construction of the sequence-defined polymer library. (A) Reaction scheme for DNA ligase-mediated translation of DNA templates into sequence-defined highly functionalized nucleic acid polymers (HFNAPs). (B) Structures of 5'-phosphorylated trinucleotide building blocks for HFNAP library synthesis. (C) Translation of libraries of randomized DNA templates into HFNAPs that incorporate up to 15 consecutive functionalized trinucleotide building blocks. (D) A complete cycle of HFNAP translation, HFNAP strand isolation, and reverse translation back into DNA faithfully recovered sequence information from the original DNA templates. In control experiments in which the trinucleotide building blocks were omitted from the polymerization reactions, the PCR step did not generate any amplicons of the correct size.
Figure 1:
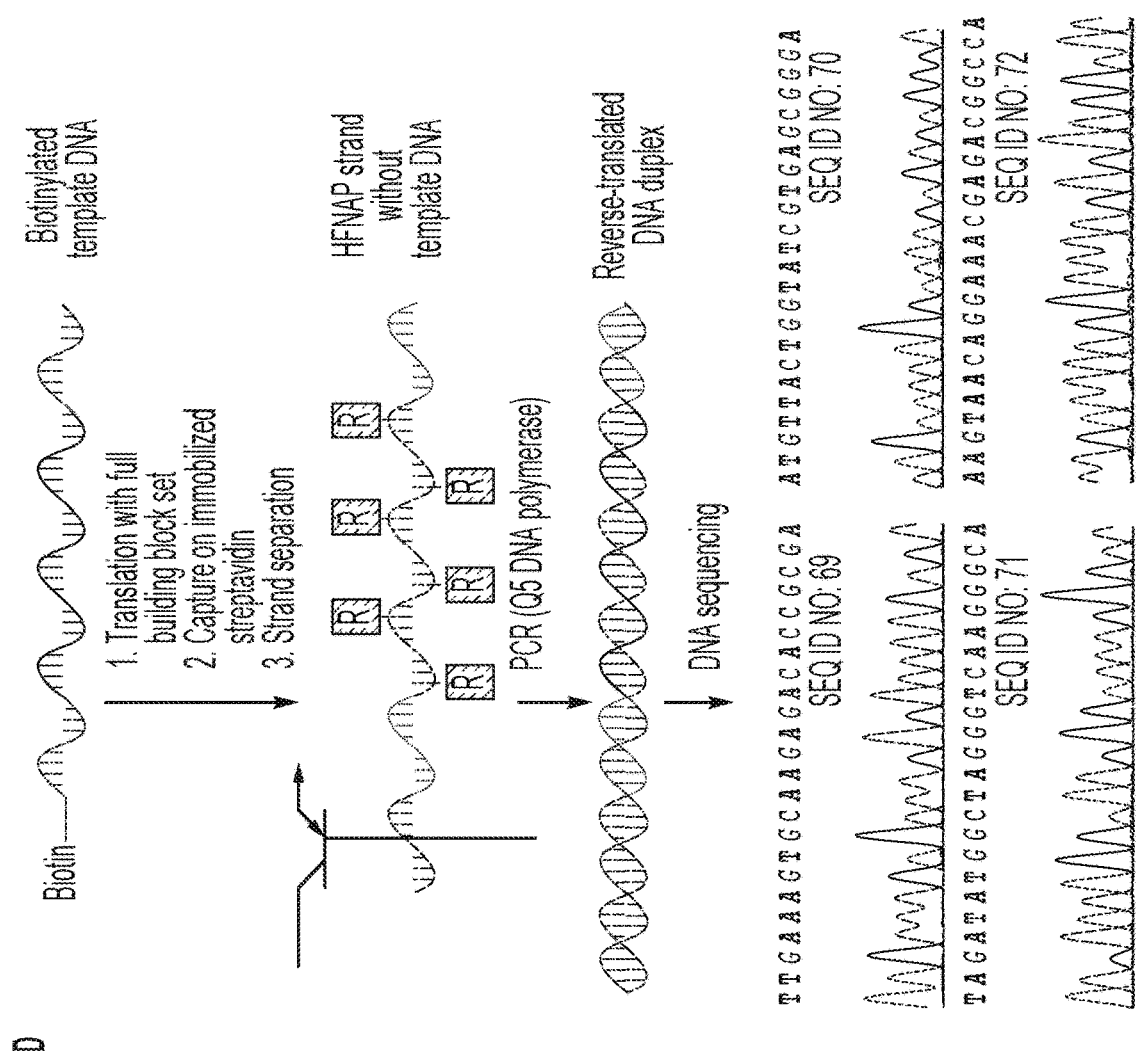

Previously an in vitro system was developed that uses DNA ligase to translate DNA sequences into sequence-defined highly functionalized nucleic acid polymers (HFNAPs) containing a wide range of side-chains chosen by the researcher (39). In a previous report, it was shown that DNA sequences can be translated into HFNAPs using DNA ligase to catalyze the polymerization of up to 50 consecutive short, chemically functionalized oligonucleotide building blocks along a DNA template (39) (FIG. 1A). It was discovered that T4 DNA ligase accepts trinucleotide building blocks with a wide range of side-chains on the 5' nucleobase, including side-chains at the C5 position of pyrimidine nucleobases that are both synthetically accessible and unlikely to disrupt Watson-Crick base pairing (39).

This artificial translation system allows researchers, in principle, to mimic and even expand the chemical repertoire of protein building blocks in an evolvable synthetic polymer system. The broad chemical scope of HFNAPs gives them the potential to adopt unique folding and functional properties distinct from those of known natural or non-natural nucleic acid polymers. The original HFNAP system proved unable to support the evolution of functional polymers, however, likely because of the limited diversity provided by its eight-codon genetic code and the long, flexible linkers present in the building blocks. In this study a new HFNAP "genetic code", translation system, and in vitro selection system was designed that overcomes these challenges, then applied the resulting HFNAP evolution system to generate sequence-defined synthetic polymers that binds two protein targets of biomedical interest.

Results

The new genetic code was designed to offer a high degree of both codon and side-chain diversity to evolving polymers (FIG. 1B). The maximum number of different trinucleotides containing a 5' pyrimidine (all 32 possible YNN combinations, where Y=C or T and N=A, C, G, or T) as codons was included. The corresponding 32 building blocks were each linked to one of eight side-chains (four codons per side-chain) that include hydrophobic, aliphatic, aromatic, halogenated, polar, and charged groups, several of which are not found among proteinogenic amino acid side-chains. The linkers between side-chains and nucleobases were redesigned compared with our original genetic code with limited conformational flexibility in order to increase the likelihood that the polymer backbone, nucleobases, and side-chains would cooperatively adopt defined folded structures. Each side-chain was assigned to a set of four codons that collectively contained the same balance of A/T versus C/G bases following the side-chain-functionalized 5' pyrimidine base.

Translation DNA-templated polymerization (artificial "translation") reactions were improved by screening ligase enzymes and adjusting polymerization conditions. It was found that subjecting translation reactions to a slow (0.01° C./s) temperature ramp to 4° C. before initiating ligation with T3 DNA ligase substantially improved yields of full-length HFNAP from libraries of DNA templates containing random coding regions of 45 nt, which encoded the incorporation of 15 consecutive side-chain-functionalized trinucleotide building blocks of mixed sequence (FIG. 1C). To test the ability of translated polymers to be "reverse-translated" back into DNA, thereby enabling iterated cycles of translation, selection, reverse translation, and PCR amplification, polymerization was performed on four templates that each encoded the incorporation of eight different building blocks and collectively covered all 32 building blocks, and then subjected the resulting HFNAP products, separated from template DNA, to reverse translation in a PCR reaction using Q5 DNA polymerase (39) (FIG. 1D). One of the PCR primers binds a 3'-overhang (FIG. 1D) present in the HFNAP products but absent in template DNA, precluding the amplification of any contaminating template DNA. DNA sequencing of the resulting PCR products showed that the original sequence information in the templates was faithfully recovered (FIG. 1D), indicating that both translation from DNA to HFNAPs and reverse translation from HFNAPs to their encoding DNA occur with high sequence fidelity using this set of building blocks.

These observations are qualitatively consistent with results from Hili and coworkers, who reported fidelities ranging from 95.1% to 98.4% per codon for ligase-mediated DNA-templated polymerization of functionalized pentanucleotides (40). Perfect fidelity is not expected for a ligase-mediated polymerization, which lacks proofreading mechanisms, but we reasoned that the level of fidelity in our system may be sufficient to support iterated selection for functional polymers, consistent with our previous mock selection results (39). Modest levels of mutations may also confer a benefit to the selection, as reported by Benner and coworkers for selections of aptamers containing novel nucleobases (37).

Figure 2:
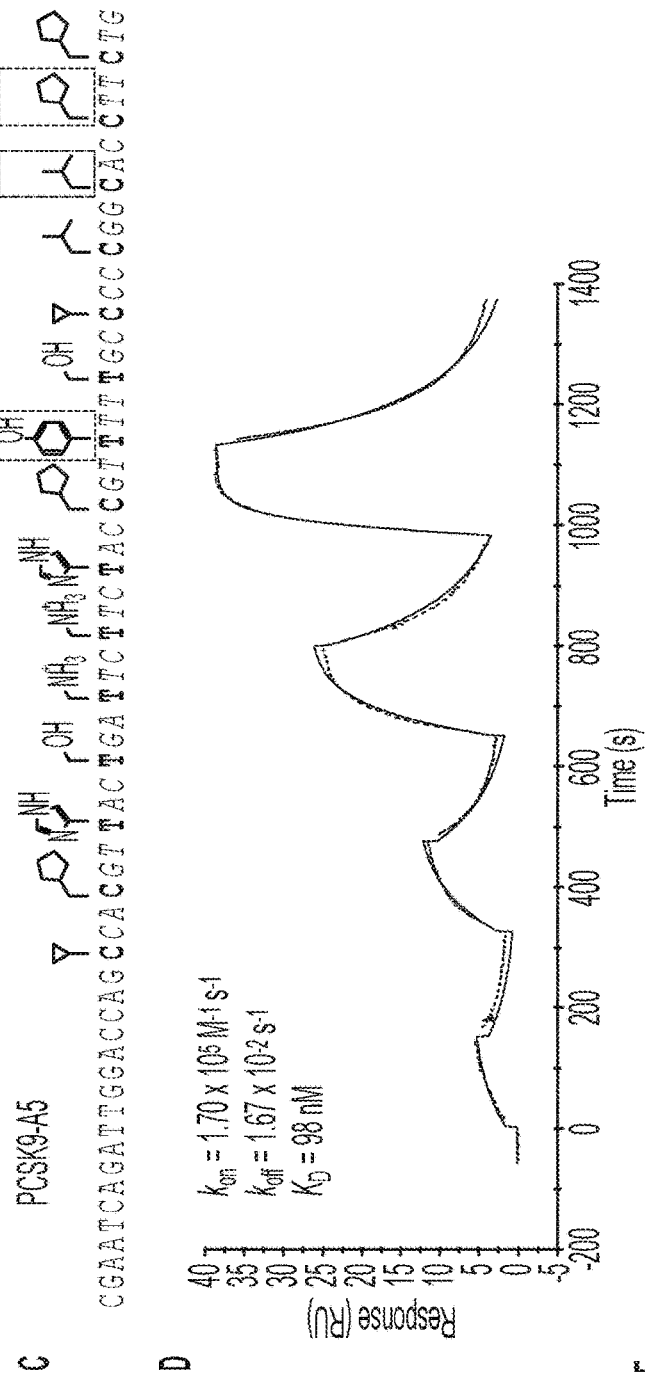
FIG. 2. Shows selection of PCSK9-binding polymers from a random HFNAP library. (A) Overview of translation, selection, and reverse translation scheme. (B) PCSK9 binding selection progress. The HFNAP pool's bulk affinity to PCSK9-coated beads was assessed by quantifying the amount of HFNAP in the flow-through versus the elution at each round of selection by quantitative PCR. Higher values in the graph indicate higher ratios of polymers that bound to immobilized PCSK9 and were eluted relative to polymers that flowed through the immobilized PCSK9. (C) Sequence and side-chain structure of selected polymer PCSK9-A5. Side-chains essential for binding activity are boxed. (D) SPR sensogram characterizing binding kinetics between surface-immobilized PCSK9-A5 polymer and the target PCSK9 protein. The concentrations of injected PCSK9 were 10, 30, 100, and 300 nM. The observed sensogram is shown in red and the fitted curve with the kinetic parameters listed is shown in black. (E) Kinetic parameters for binding of PCSK9-A5 or its side-chain-deficient variants to PCSK9 protein, as measured by SPR. For the variants "TTT ΔSide chain", "TTT Linker only", and "CTT ΔSide chain", no SPR signal was observed at highest analyte concentration tested (300 nM PCSK9).

Encouraged by these developments, a library of HFNAPs was generated containing 15 consecutive building blocks drawn from the set of 32 (theoretical polymer library space=$3\times10^{22}$; average HFNAP molecular weight=28 kDa) and subjected the resulting library (starting quantity=$3\times10^{12}$ molecules) to iterated rounds of in vitro selection for binding to PCSK9 protein, a target implicated in low-density lipoprotein (LDL) metabolism and cardiovascular disease (41-43) (FIG. 2A). The HFNAP library was incubated with PCSK9 protein immobilized on agarose beads. After washing the beads with buffer, the bound HFNAPs were eluted by boiling the beads in buffer containing detergent. The surviving HFNAPs were reverse translated in a PCR reaction using Q5 DNA polymerase, and the resulting double-stranded DNAs were purified by PAGE. The non-template strands were removed by alkaline denaturation, and the streptavidin-bound template strands were translated back into HFNAPs by ligase-catalyzed DNA-templated polymerization for the next round of PCSK9-binding selection. It is noted that the ability of HFNAPs to be directly reverse-translated by a DNA polymerase, though not an absolute requirement for iterated selection as demonstrated by the use of display methods to evolve nucleic acids (17, 44), provides a practical and high-fidelity way to complete a selection cycle.

As the iterated rounds of selection progressed, the fraction of HFNAP that was retained on PCSK9-linked beads generally increased, consistent with enrichment of PCSK9-binding polymers, even though selection stringency was steadily elevated by decreasing the amount of PCSK9 protein (FIG. 2B). At the eighth round of selection, the polymer population was retained by PCSK9 protein-conjugated agarose beads with an efficiency of approximately 10%. In contrast, less than 0.1% of the same polymer population was retained on agarose beads not conjugated to any protein (FIG. 2B), suggesting that the ability of the selected polymers to bind PCSK9-linked beads arose from their ability to bind PCSK9, rather than agarose beads.

Figure 5:
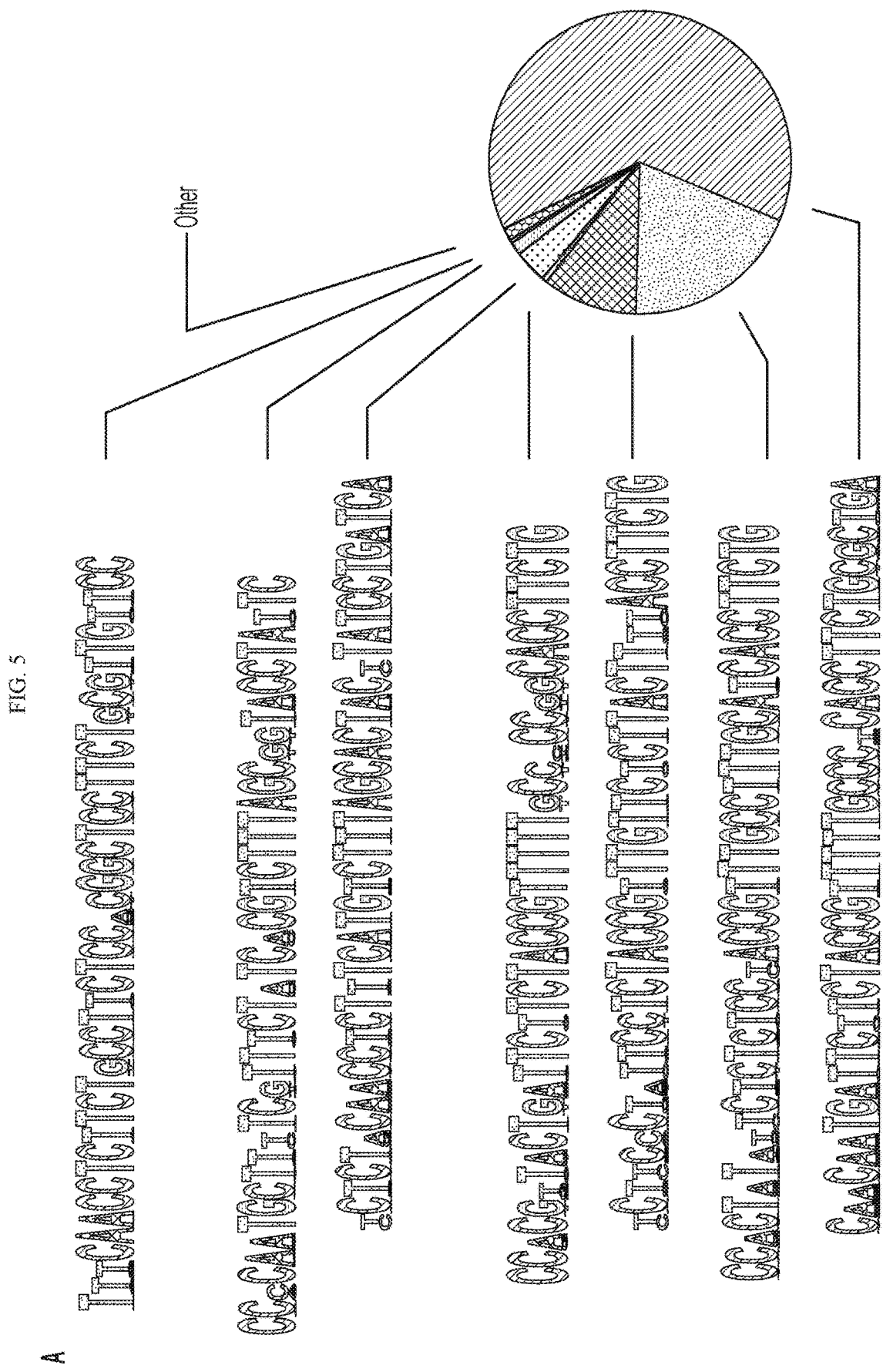
FIG. 5. Shows sequence homology and characterization of selection-enriched PCSK9-binding HFNAPs. (A) Relative abundances and sequence logos of the dominant seven sequence clusters after nine rounds of PCSK9-binding selection from a naïve library. (B) Retention of selection-enriched HFNAPs (only the variable, functionalized parts of the sequences are shown) on immobilized PCSK9 (target; top bars) and immobilized thrombin (non-target; middle bars) and of sequence-matched unfunctionalized DNA on immobilized PCSK9 (bottom bars), as quantified by qPCR. n.d.=not determined.

Results from high-throughput DNA sequencing after nine rounds of selection indicated that the HFNAP pool had strongly converged to just seven sequence families containing conserved sub-sequences suggestive of common binding motifs (FIG. 5A). Sequences within the same family were likely descendants of a single parental polymer derived through mutations that accumulated through the selection process, as evidenced by high levels of homology. The seven most highly enriched HFNAPs were individually synthesized by ligase-mediated DNA-templated polymerization and tested their retention on immobilized PCSK9 or immobilized thrombin, an unrelated protein. Five of the seven tested polymers exhibited substantial apparent binding activity to immobilized PCSK9 beyond any apparent binding to immobilized thrombin. Unfunctionalized DNA sequences (lacking any side-chains) corresponding to these seven HFNAPs were also assayed and no evident PCSK9-binding activity was observed (FIG. 5B). Together, these results suggest that the HFNAP populations emerging from nine rounds of in vitro selection converged on a small number of polymer families that bind immobilized PCSK9 in a manner dependent on the polymers' side-chains.

Figure 6:
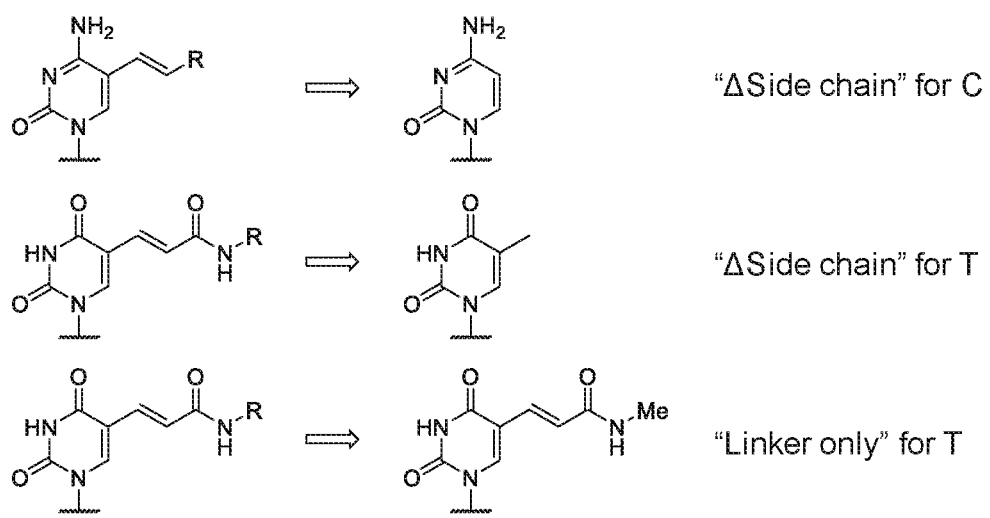
FIG. 6. Shows structures of bases in side-chain mutants characterized during structure-activity relationship studies of PCSK9-A5 and PCSK9-Evo5.

PCSK9-A5, the polymer with the highest apparent PCSK9 binding activity (FIG. 2C) was characterized. Biotinylated PCSK9-A5 was synthesized by templated translation and confirmed its binding affinity for PCSK9 (dissociation constant $K_D$=98 nM) by surface plasmon resonance (SPR) (FIG. 2D). To probe the role of the side-chain functional groups, side-chain mutants of PCSK9-A5 were synthesized in which all instances of each building block were replaced by the corresponding trinucleotide either lacking any side-chain or containing a linker but missing the side-chain's functional group (FIG. 6). The removal of a single phenol side-chain in codon 9 or a single cyclopentyl side-chain in codon 14 completely abolished the binding between PCSK9-A5 and its target (FIGS. 2C and 2E). Furthermore, the removal of the isopentyl side-chain at codon 13 resulted in an approximately two-fold reduction in affinity (FIGS. 2C and 2E). The individual removal of other side-chains had less significant effects on binding affinity. However, they may play important roles in PCSK9 binding in the context of the entire polymer.

Figure 3:
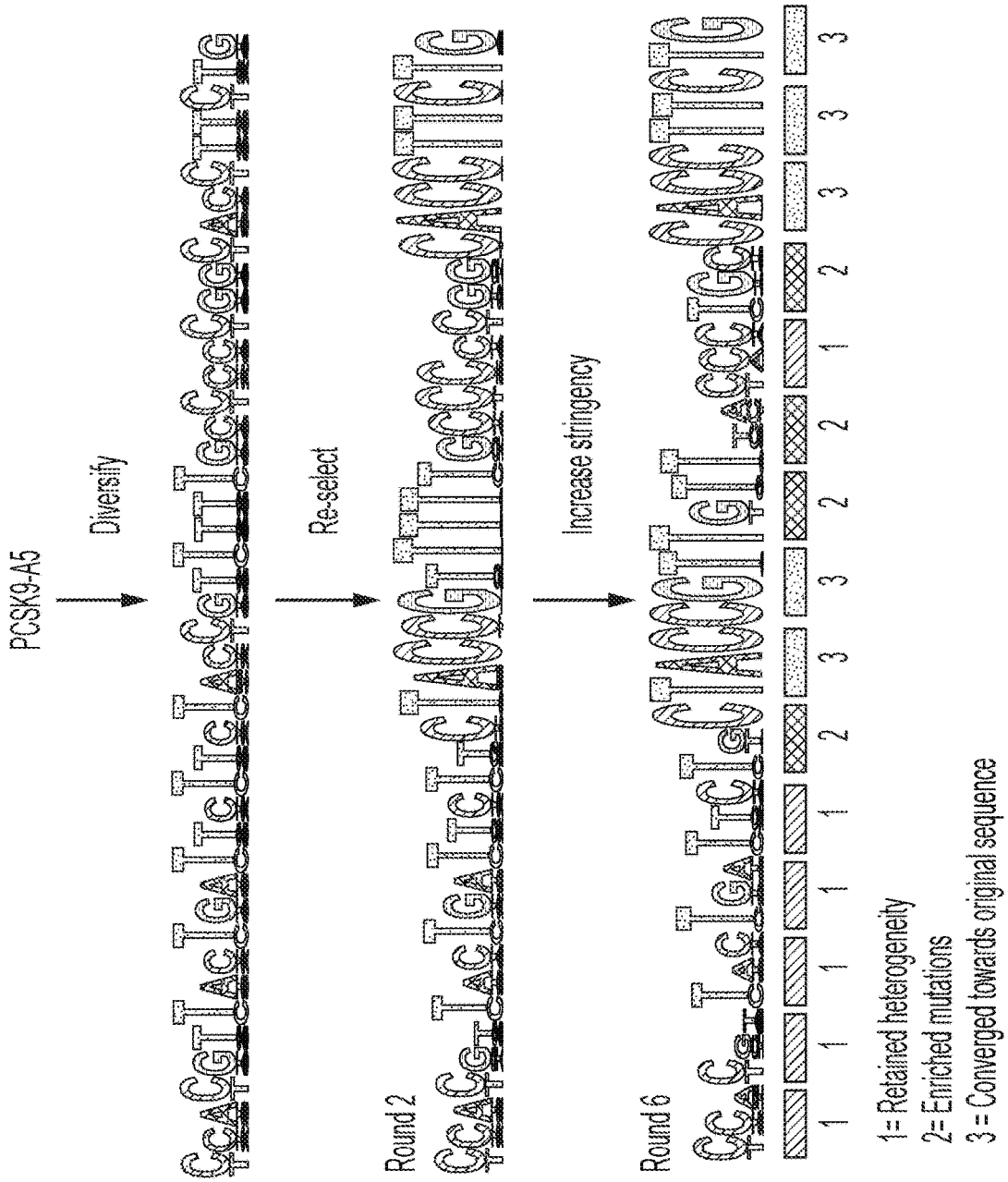
FIG. 3. Shows evolution of an improved PCSK9-binding polymer. (A) Evolution scheme and DNA sequencing results of the diversification and iterated selection of PCSK9-A5 variants with increased PCSK9 binding activity. (B) Affinity maturation of the diversified PCSK9-A5 pool. The evolving polymer pool's bulk affinity to immobilized PCSK9 was assessed by quantifying the amount of HFNAP in the flow-through and the elution at each round of selection by quantitative PCR. (C) Sequence and side-chain structure of the resulting PCSK9-Evo5 polymer. Side chains essential for binding activity are boxed. (D) Kinetic parameters for binding of PCSK9-Evo5 or its side-chain-deficient variants to PCSK9 protein, as measured by SPR. For the variants "TGT ΔSide chain", "TGT Linker only", and "CTT ΔSide chain", no SPR signal was observed at the highest analyte concentration tested (60 nM PCSK9). For the variant "CAC ΔSide chain", the binding interaction fits a two-state reaction kinetic model with KD≈420 nM. Representative sensograms are provided in FIG. 8. (E) SPR sensogram characterizing binding kinetics between PCSK9-Evo5-syn and surface-immobilized PCSK9 protein. The concentrations of injected PCSK9-Evo5-syn were 1.8, 6, 18, 60, and 180 nM. The observed sensogram is shown in red and the fitted curve with the kinetic parameters listed is shown in black. (F) SPR response on an LDLR-coated surface produced by flowing PCSK9 in the presence of either PCSK9-Evo5-syn, unfunctionalized DNA of identical sequence to PCSK9-Evo5-syn, unlabeled LDLR, or a known PCSK9-neutralizing monoclonal antibody. The SPR response shown is normalized to the response in experiments without any competitor (defined as an SPR response of 1). Raw sensograms are provided in FIG. 12.
Figure 3:
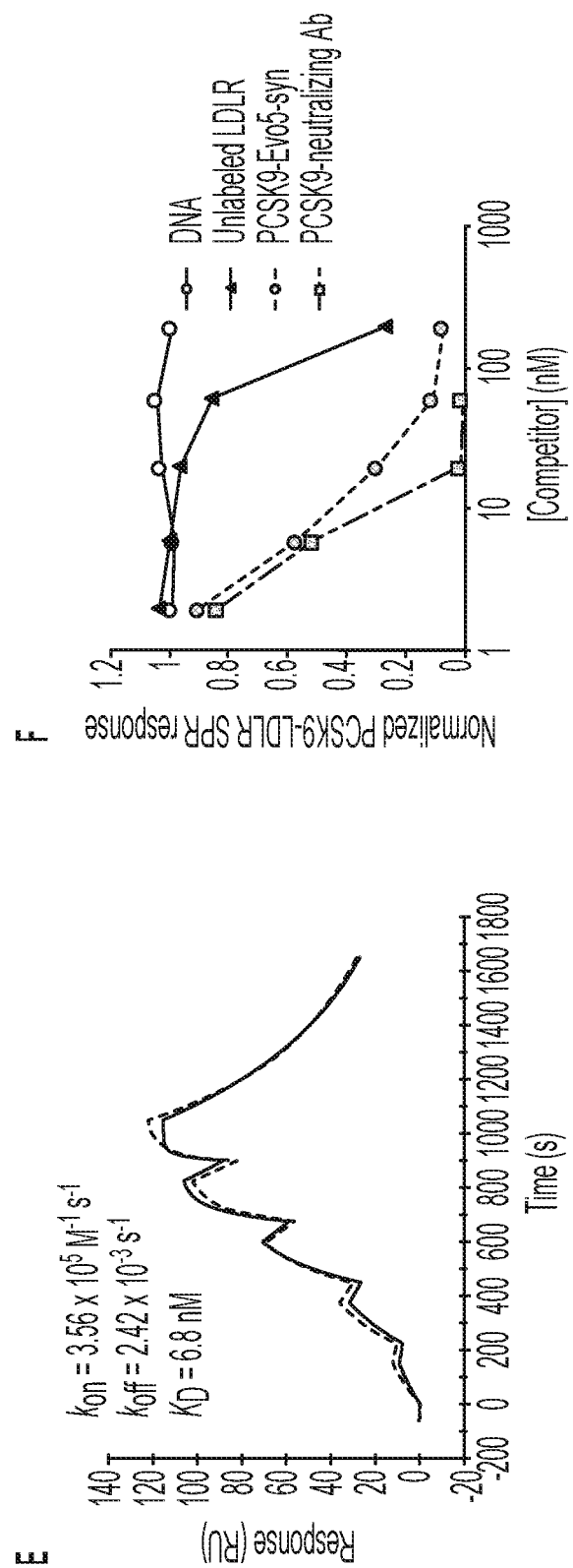
Figure 7:
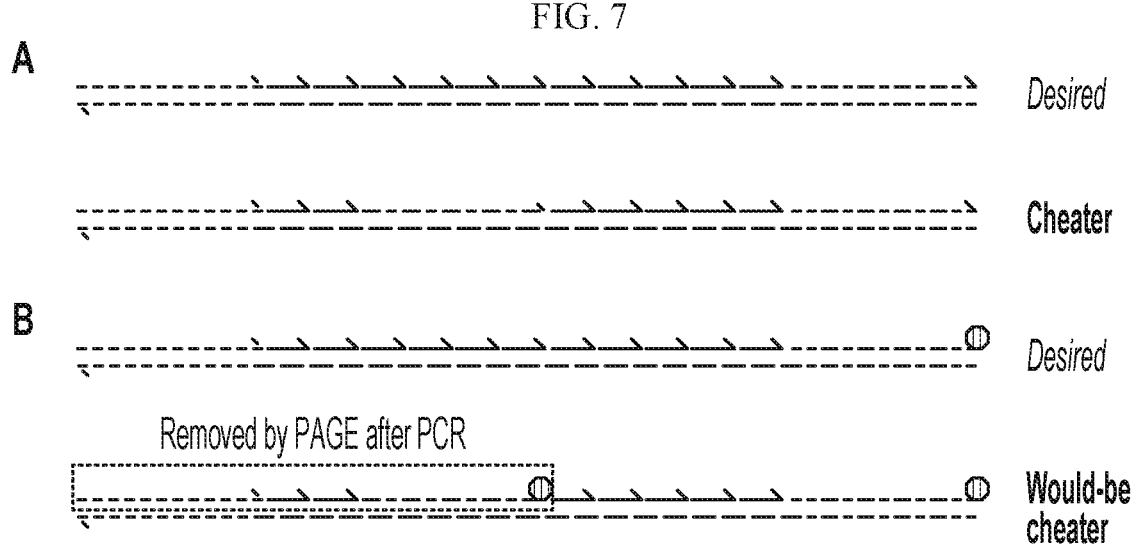
FIG. 7. Shows cheater suppression strategy. (A) In addition to the desired polymerization reaction (top), incorporation of a polymerization primer in the coding region can generate undesired cheaters (bottom) that rapidly amplify during PCR due to their small size and eventually dominate the sequence pool over rounds of selection. (B) Using a non-extendable 2',3'-dideoxyribose-terminated 3' polymerization primer addresses this problem, as truncated cheaters can be removed during PAGE purification.

Given the vast sequence space of the HFNAP library ($3\times10^{22}$ possible polymers), evolution would likely generate polymer variants with improved activity in the initial population of $3\times10^{12}$ HFNAP molecules. To evolve the PCSK9-A5 polymer into variants with improved PCSK9 affinity, a library of mutated PCSK9-A5 templates was synthesized containing 79% identity and 21% diversity (79:21 at the pyrimidine-only first position and 79:7:7:7 at the second and third positions of each codon) for each nucleotide in the variable region (FIG. 3A). The resulting mutated PCSK9-A5 library was subjected to six additional iterated cycles of translation and selection for PCSK9 binding (FIG. 7). After just one round of enrichment at a stringency level comparable to that of the last round of initial selection, the mutated PCSK9-A5 library exhibited bulk affinity for PCSK9-conjugated beads (FIG. 3B). High-throughput DNA sequencing revealed that the mutant population after a second round of translation and selection began to converge toward the sequence of PCSK9-A5 at many positions (FIG. 3A). In subsequent rounds, the amount of immobilized PCSK9 was reduced to further increase selection stringency. Four additional rounds of translation and selection resulted in steadily improved retention of the polymer population on immobilized PCSK9 (FIG. 3B).

High-throughput sequencing revealed new consensus codons at four out of 15 positions within the population of evolved polymers (FIG. 3A). Among these four positions, codons 6, 10, and 12 evolved a different side-chain compared with that of PCSK9-A5, while codon 9 evolved a different codon (TGT instead of TTT) encoding the same phenol side-chain at this position. In addition, five other codons converged to the original sequence in PCSK9-A5, and six other codon positions, mostly near the 5' end, retained sequence heterogeneity introduced during mutation, suggesting that these positions do not strongly contribute to binding activity (FIG. 3A). The three side-chain functional groups that were shown to be crucial to the PCSK9-binding activity of PCSK9-A5 were all maintained in the consensus sequence of the evolved polymer population.

Figure 8:
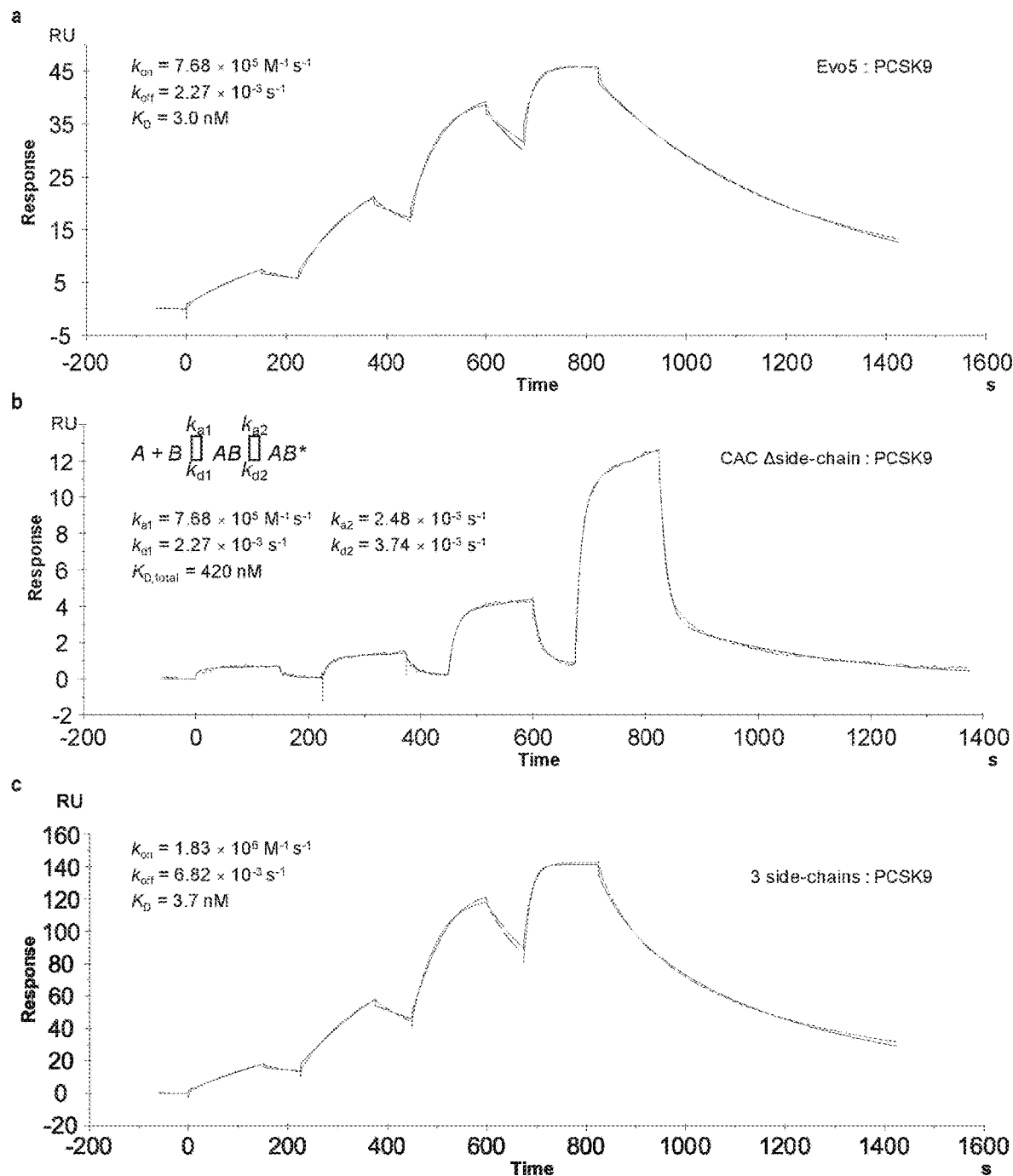
FIG. 8. Shows SPR sensograms characterizing binding kinetics between PCSK9 protein and (A) surface-immobilized biotinylated PCSK9-Evo5 or (B) surface-immobilized biotinylated PCSK9-Evo5-"CACΔSide chain" or (C) surface-immobilized biotinylated PCSK9-"3 side chains." The concentrations of injected PCSK9 were 2, 6, 20, and 60 nM. The raw sensograms are shown in red and the fitted curves with the kinetic parameters listed are shown in black.
Figure 9:
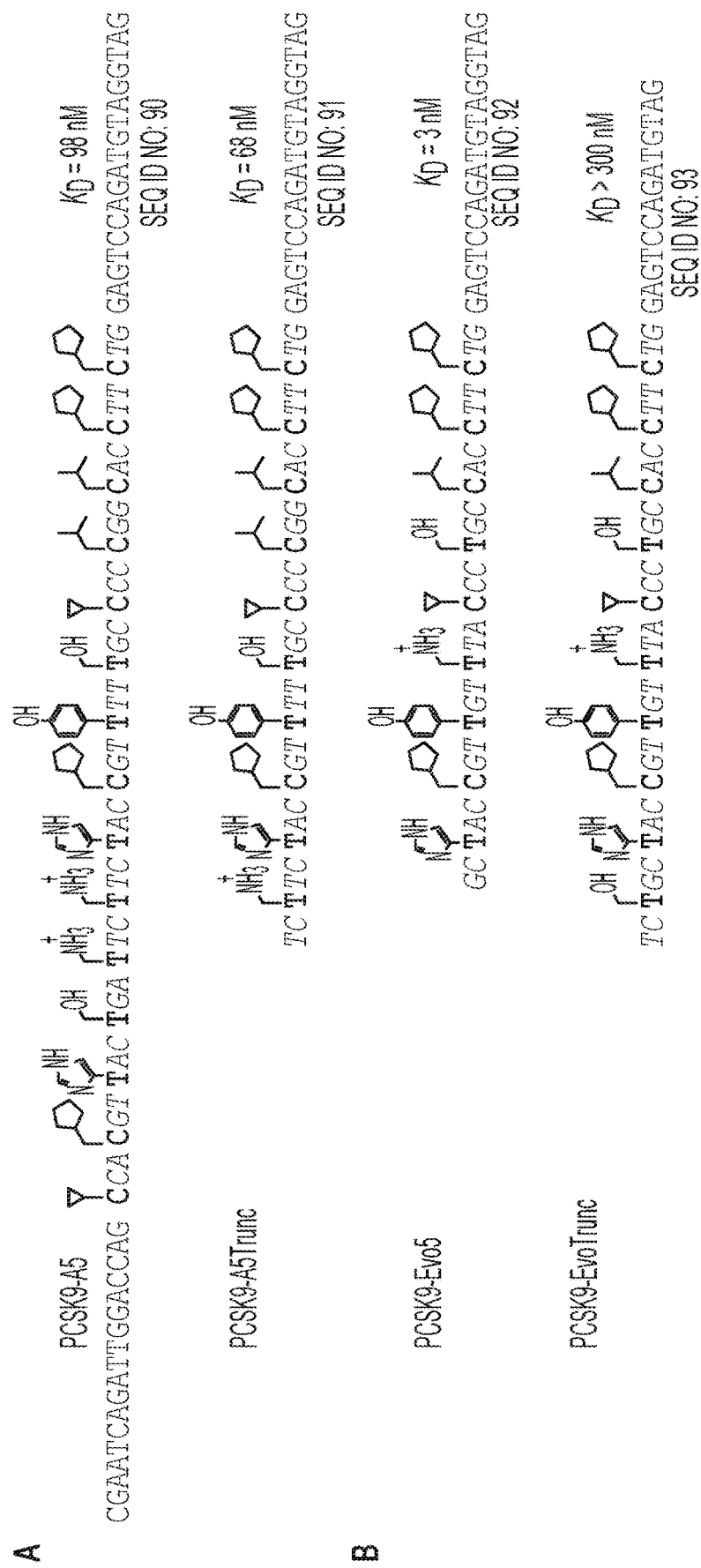
FIG. 9. Shows effects of truncating (A) PCSK9-A5 and (B) PCSK9-Evo5. No binding of up to 300 nM solution-phase PCSK9 to surface-immobilized PCSK9-EvoTrunc was observed by SPR.

A biotinylated, truncated HFNAP (designated PCSK9-Evo5; FIG. 3C) was synthesized retaining only the evolved consensus sequence and the 3' constant region, and measured its affinity for PCSK9 to be $K_D$=3.0 nM (FIG. 3D and FIG. 8A), representing a 33-fold increase over that of PCSK9-A5. In contrast, a similarly truncated version of PCSK9-A5 (designated PCSK9-A5Trunc) did not substantially improve affinity ($K_D$=68 nM) over that of full-length PCSK9-A5 ($K_D$=98 nM) (FIG. 9A). Additional truncation of PCSK9-Evo5 from the 3'-end resulted in complete loss of affinity (FIG. 9B). Similar to the structure-activity relationships observed for PCSK9-A5, the removal of a single phenol or cyclopentyl side-chain from PCSK9-Evo5 abolished its affinity to PCSK9 protein (FIG. 3D), and the removal of the isopentyl side-chain severely impaired target binding (the binding interaction approximately fits a two-state reaction kinetic model with $K_D\approx420$ nM; FIGS. 3D and 8B). The individual removal of other side-chains had less significant effects on binding affinity; indeed an HFNAP containing only three side chains (phenol at position 9, isopentyl at position 21, and cyclopentyl at position 24) and the rest of the Evo5 sequence as unfunctionalized DNA maintains strong binding to PCSK9 ($K_D$=3.7 nM; FIGS. 3D and 8B). Together, these results establish the evolution (iterated selection with intervening mutation and replication) of a sequence-defined synthetic polymer with improved target affinity from mutation followed by iterated translation, selection, and reverse translation.

Figure 10:
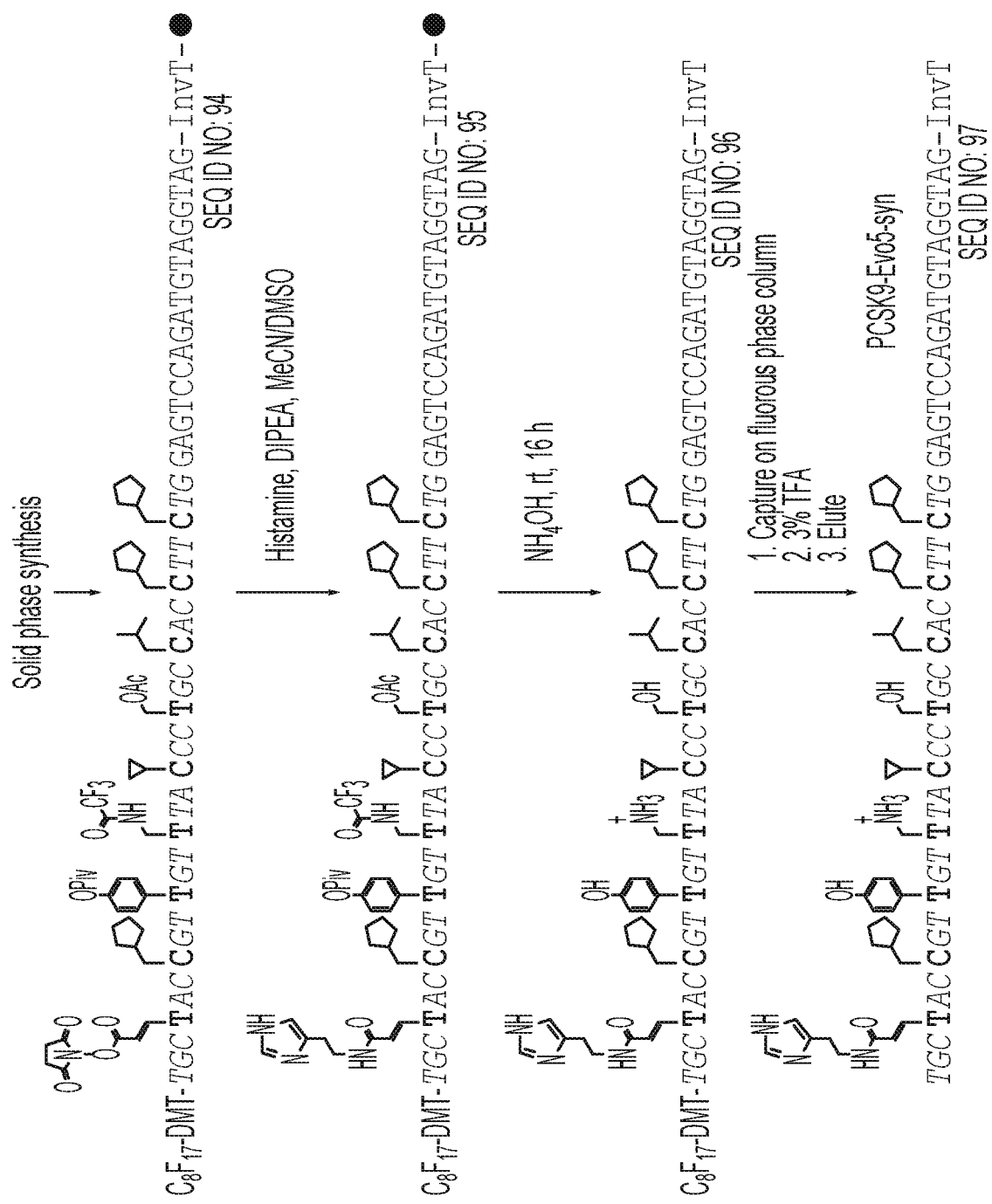
FIG. 10. Shows multi-milligram-scale synthesis scheme for PCSK9-Evo5-syn.
Figure 11:
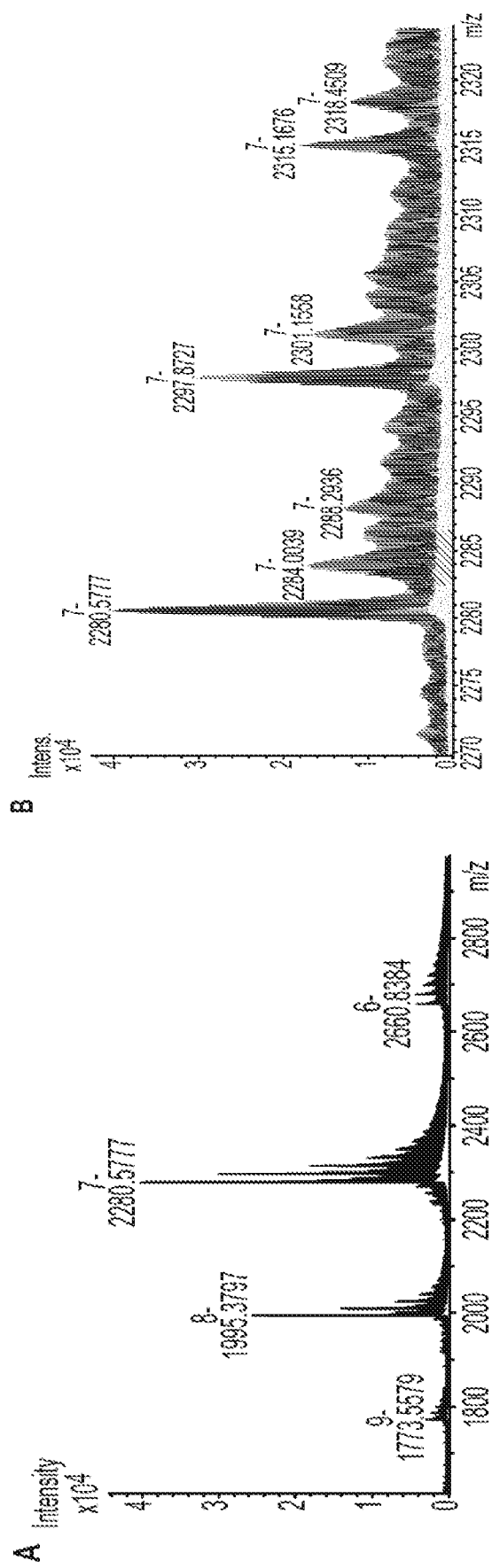
FIG. 11. Shows ESI-MS spectrum of PCSK9-Evo5-syn (molecular formula: $C_{536}H_{683}N_{177}O_{305}P_{48}$). (A) Full spectrum. (B) Spectrum detailing the "7-" group of peaks, showing the peak clusters for [M-7H]7- (around m/z 2280.5777), as well as the sodium adduct (around m/z 2284.0039), the Tris adduct (around m/z 2297.8727), and other multiple adducts. (C) Top: observed spectrum of the [M-7H]7- peak cluster. Bottom: predicted spectrum based on the molecular formula and isotopic abundances.
Figure 11:
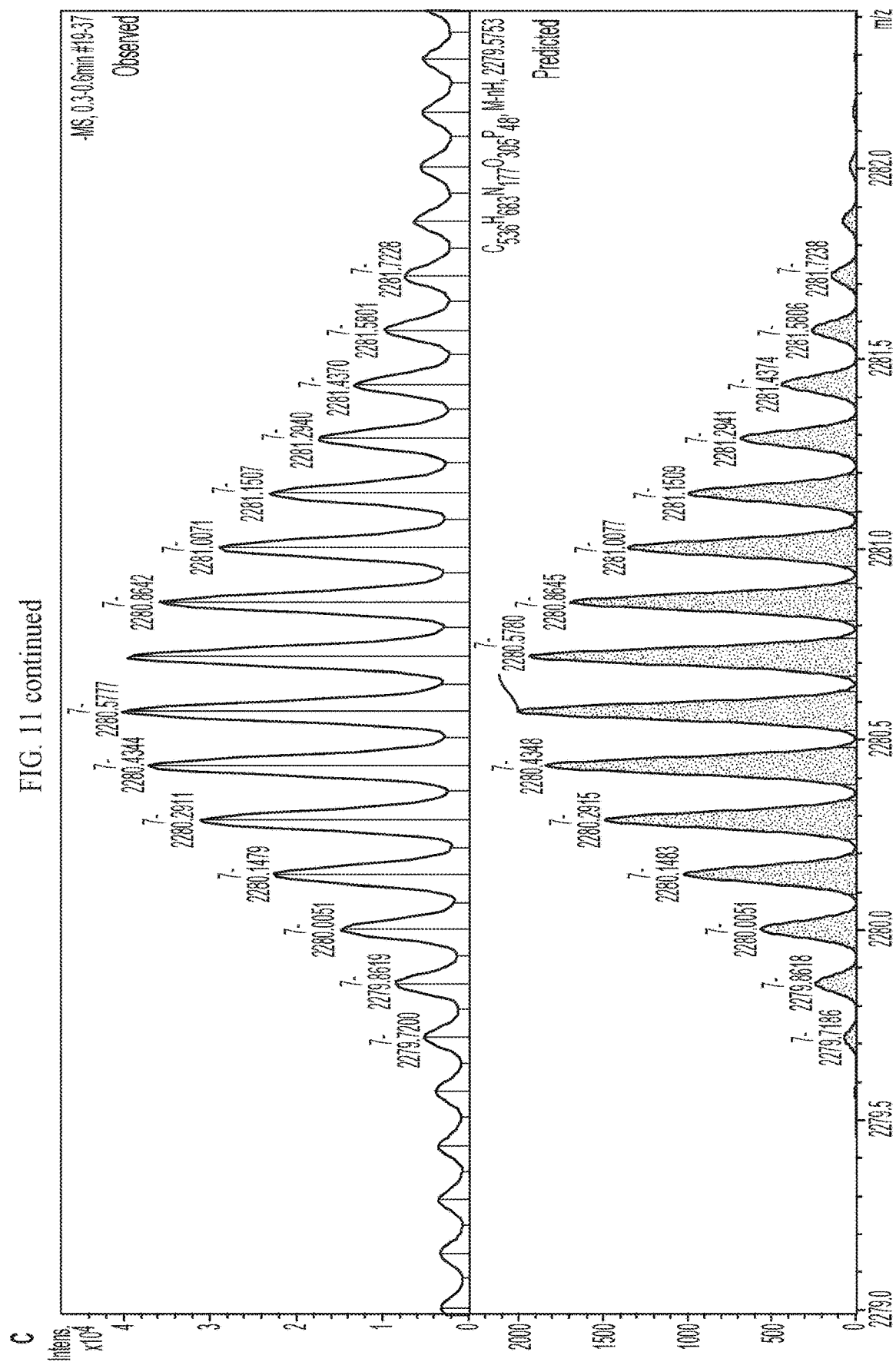

To further characterize PCSK9-Evo5, the multi-milligram-scale total synthesis of a variant of PCSK9-Evo5 (PCSK9-Evo5-syn) was executed, which has an additional 3' inverted dT base for exonuclease resistance (46), using standard phosphoramidite chemistry on solid support (FIG. 10). It was planned to install all side-chain-functionalized building blocks entirely through corresponding side-chain-functionalized phosphoramidite reagents, with the nucleophilic functional groups protected with base-labile protecting groups that would be removed under standard oligonucleotide deprotection conditions. Although most of the side-chain-functionalized nucleoside phosphoramidites were readily synthesized (Methods), the imidazole-bearing thymidine reagent proved difficult to prepare. PCSK9-Evo5-syn was therefore synthesized on solid phase with an activated ester (NHS-carboxy-dT) in place of the imidazole-functionalized thymidine, and coupled histamine to that position in the bead-bound polymer chain to install the imidazole side-chain before global deprotection and cleavage from solid support with ammonium hydroxide (FIG. 10). The identity of PCSK9-Evo5-syn (approximately 2 mg from a one-micromole solid-phase synthesis, ~13% overall yield) was confirmed by high-resolution mass spectrometry (FIG. 11). High-affinity binding ($K_D$=6.8 nM) between totally synthetic PCSK9-Evo5-syn and biotinylated Avi-tagged PCSK9 was confirmed by SPR (FIG. 3E).

Figure 12:
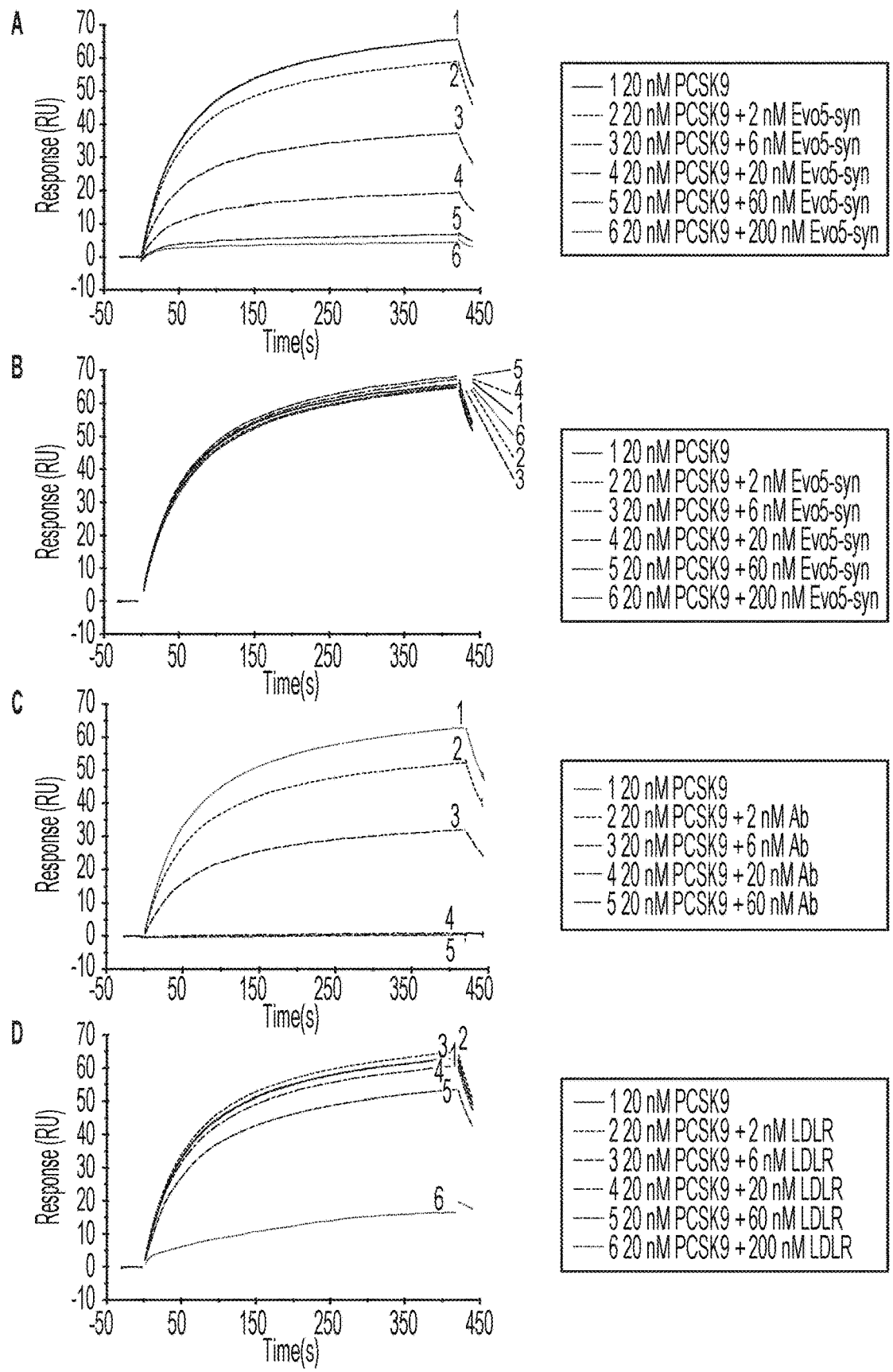
FIG. 12. Shows SPR sensograms characterizing the interaction between surface-immobilized LDLR and PCSK9 pre-incubated with varying concentrations of (A) PCSK9-Evo5-syn, (B) sequence-matched unfunctionalized DNA, (C) a known PCSK9-neutralizing antibody, or (D) unlabeled LDLR.
Figure 13:
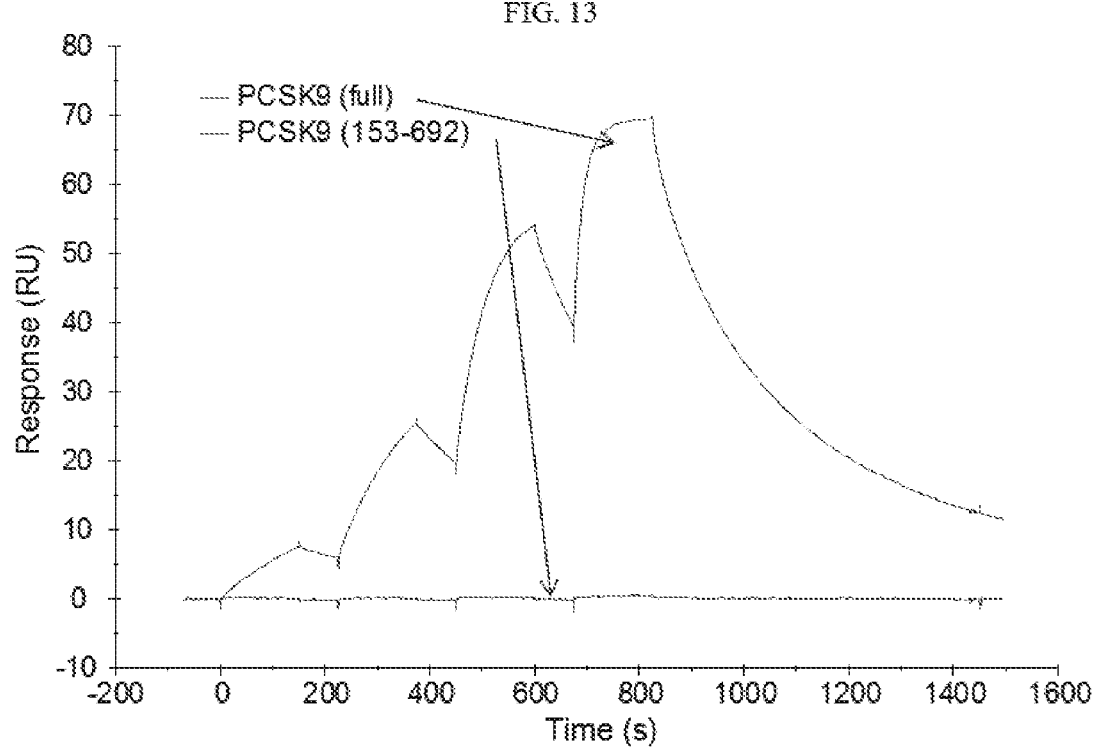
FIG. 13. Shows SPR sensograms characterizing binding kinetics between surface-immobilized biotinylated PCSK9-Evo5 and either full-length PCSK9 protein or a truncated PCSK9 protein missing the prodomain. The concentrations of injected protein were 2, 6, 20, and 60 nM.

PCSK9 regulates cholesterol metabolism by binding the LDL receptor (LDLR) and promoting the lysosomal degradation of LDLR (42). The ability of PCSK9-Evo5-syn to disrupt PCSK9-LDLR binding in an SPR assay was tested. PCSK9-Evo5-syn dose-dependently reduced binding of PCSK9 to surface-immobilized LDLR (FIG. 3F and FIG. 12A) The potency of PCSK9-Evo5-syn inhibition of PCSK9-LDLR binding ($IC_{50}$=~9 nM) was similar to that of a known PCSK9-neutralizing monoclonal antibody (FIG. 3F and FIG. 12C). In contrast, unfunctionalized DNA of the same sequence as PCSK9-Evo5-syn produced no inhibitory effect (FIG. 3F and FIG. 12B), consistent with the necessity of the side chains implicated in PCSK9 binding (FIGS. 2C-E and FIGS. 3C-D). The affinity of surface-immobilized PCSK9-Evo5 to different PCSK9 protein constructs was also tested and it was found that a truncated PCSK9 variant lacking the prodomain exhibited no apparent binding to PCSK9-Evo5 (FIG. 13), implicating the PCSK9 prodomain, known to be involved in a secondary binding interface between PCSK9 and LDLR (47), in mediating the interaction of PCSK9 with PCSK9-Evo5.

Figure 4:
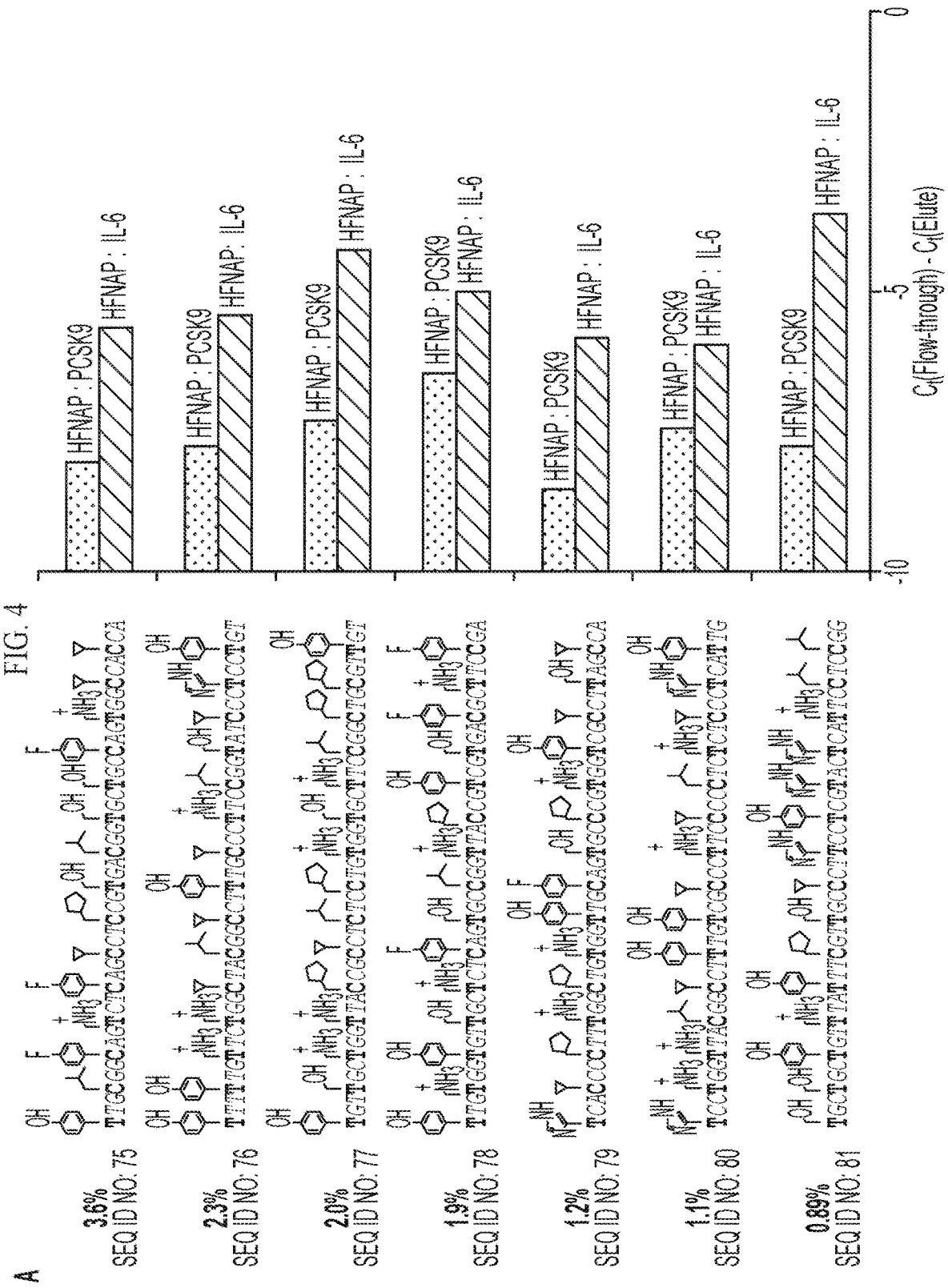
FIG. 4. Shows characterization of IL-6-binding HFNAPs selected from a random library. (A) Retention of individual selection-enriched HFNAPs on immobilized IL-6 (target; bottom bars) or immobilized PCSK9 (non-target; top bars). The percentages of each sequence in the pool after seven rounds of selection are listed to the left. (B) Sequence and side-chain structure of IL6-A7. Side-chains essential for binding activity are boxed. (C) SPR sensogram characterizing binding kinetics between biotinylated IL6-A7 and its target IL-6 protein. The concentrations of injected IL-6 were 10, 30, 100, and 300 nM. The observed sensogram is shown in red and the fitted curve with the kinetic parameters listed is shown in black.
Figure 4:
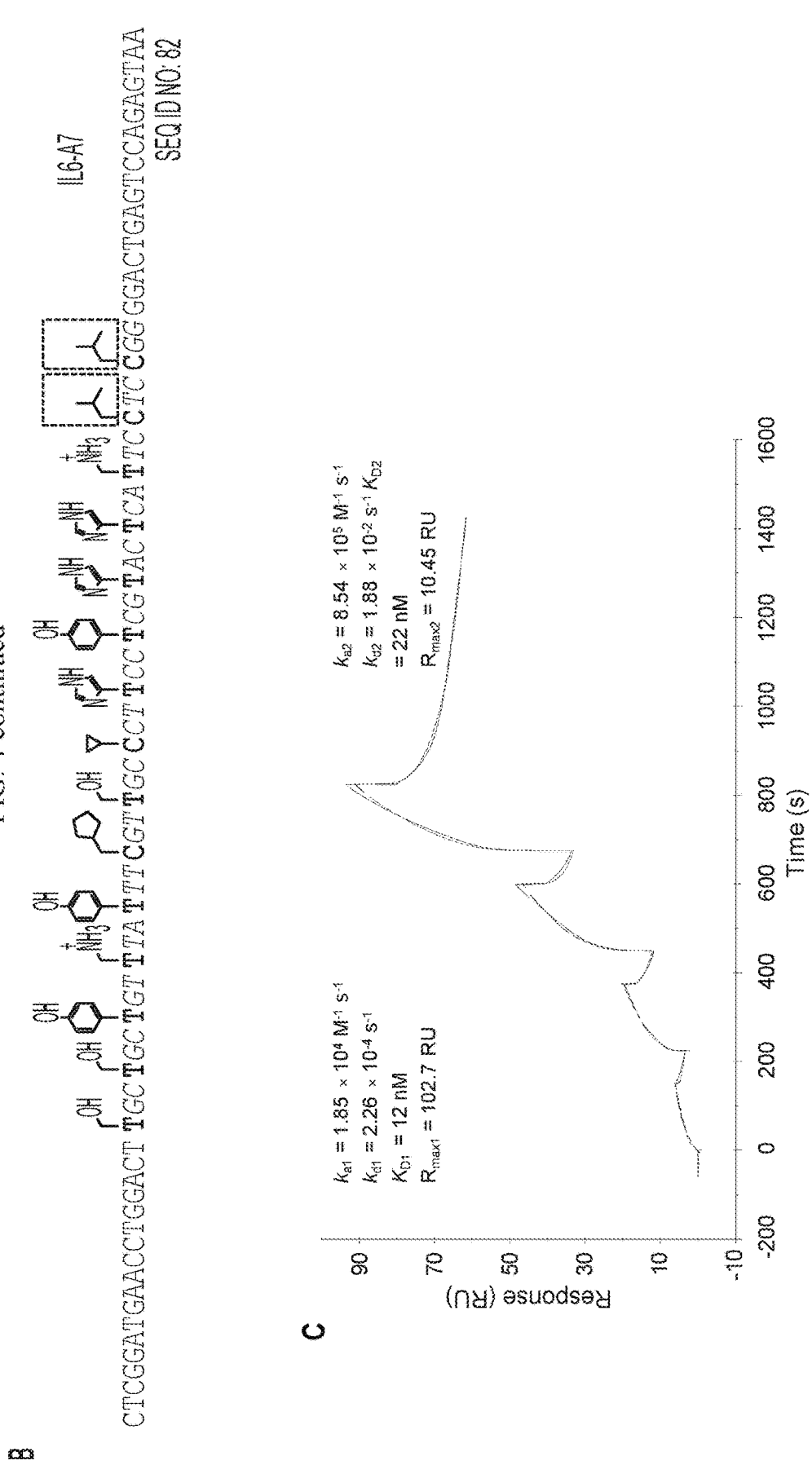

To test the generality of our polymer evolution system and to investigate the potential of this new class of polymers to evolve receptors to different proteins, a separate selection for HFNAPs that bind a protein unrelated to PCSK9 was performed. Human interleukin-6 (IL-6), a key cytokine involved in inflammation and the target of many drugs and drug candidates (48), including modified DNA aptamers (24, 25) was chosen. After seven iterated cycles of translation, selection for binding to immobilized IL-6 protein, reverse translation, and amplification, the most abundant sequence accounted for 3.6% of the population (FIG. 4A). The top seven HFNAPs were individually synthesized and assayed for binding to immobilized IL-6.

Based on its high apparent binding activity to immobilized IL-6, but not to immobilized PCSK9 (FIG. 4A), the HFNAP IL6-A7 (FIG. 4B) was chosen for further characterization. Binding of biotinylated IL6-A7 to the target IL-6 protein was confirmed by SPR. Although the binding kinetics of IL6-A7 to IL-6 protein did not conform to a classical one-to-one binding model, a phenomenon often observed in aptamer-protein binding (18, 24) fitting to a heterogeneous ligand model resulted in an apparent affinity of $K_D$=12 nM for the major component and $K_D$=22 nM for the minor component (FIG. 4C).

Figure 14:
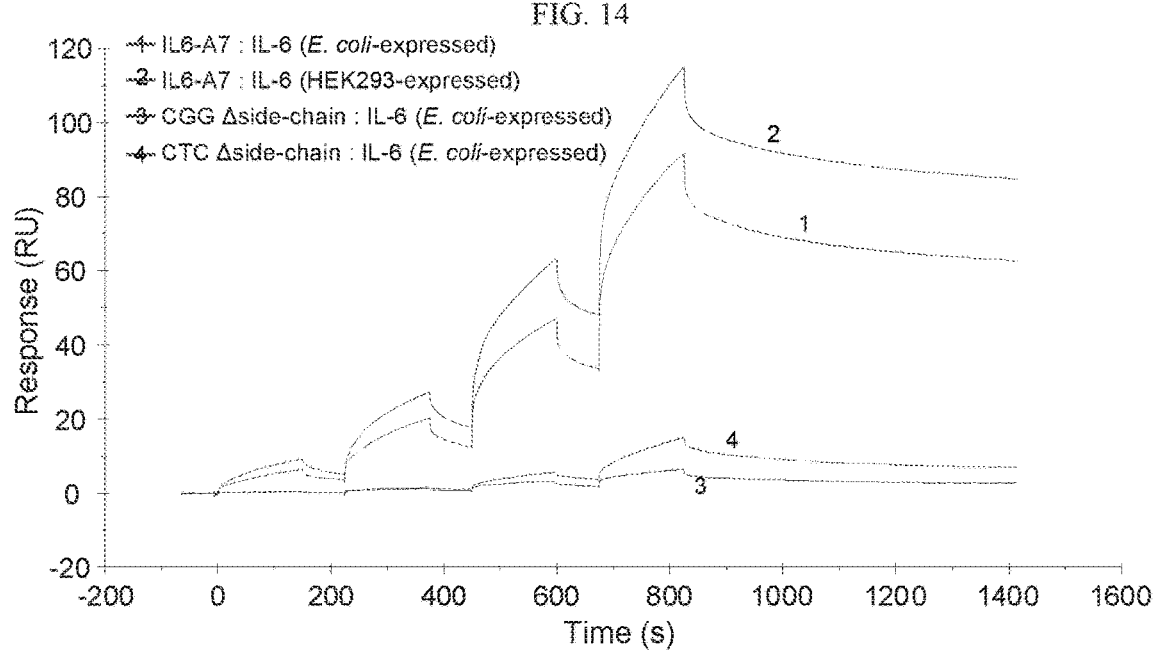
FIG. 14. Shows SPR sensograms characterizing binding kinetics between biotinylated IL6-A7 (1) or two side-chain variants (3 and 4) and *E. coli*-expressed IL-6 protein, and between biotinylated IL6-A7 and HEK293 cell-expressed IL-6 protein (2). For all experiments, comparable amounts of the biotinylated HFNAPs (all between 90 and 120 RU) were immobilized on the active flow cell. The concentrations of injected IL-6 were 10, 30, 100, and 300 nM.
Figure 15:
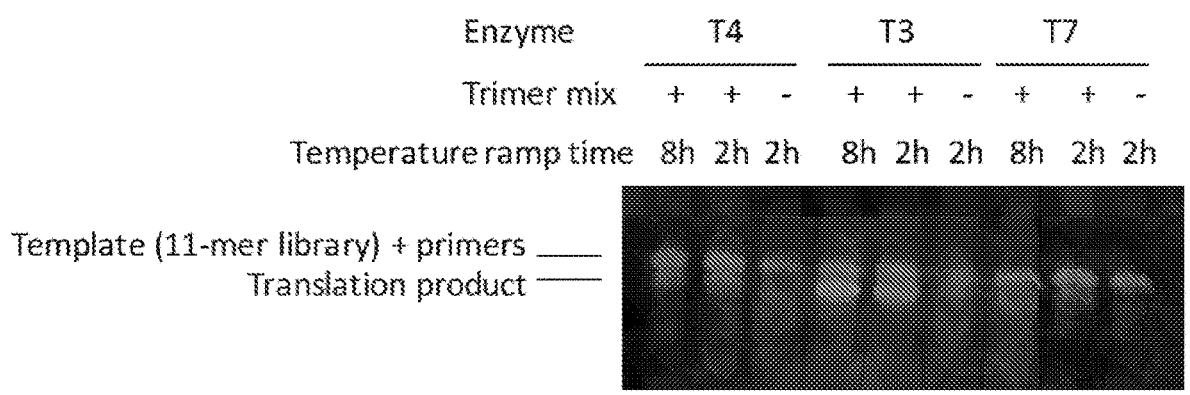
FIG. 15. Screening of ligases for polymerization. The translation reactions, as well as control reactions from which the trinucleotide building blocks were omitted, were analyzed by polyacrylamide gel electrophoresis on a non-denaturing 10% TBE gel and imaged by SYBR Gold staining. T3 DNA ligase mediated higher translation efficiency than T4 and T7 DNA ligases. Increasing the temperature ramp-down time from 2 hours to 8 hours had little effect on translation yield.

The binding kinetics and affinity of IL6-A7 to *E. coli*-expressed IL-6 (used in the selection) and to human HEK293 cell-expressed IL-6 protein were comparable (FIG. 14). SPR was used to measure the IL-6 affinity of IL6-A7 side-chain mutants in which all instances of a trimer building block were replaced by the corresponding trinucleotide lacking any side-chain. The mutants missing isopentyl side-chain in either codon 14 or codon 15 exhibited severely impaired binding (FIG. 14), implicating these two side chains as key determinants of IL-6 binding activity in IL6-A7.

Discussion

We used a ligase-mediated DNA-templated polymerization system and in vitro selection to evolve HFNAPs, nucleic acid polymers that are densely functionalized with chemically diverse side-chains. HFNAPs that bind PCSK9 and IL-6 were selected from random polymer libraries. Through diversification and reselection, we evolved an improved PCSK9-binding HFNAP (Evo5) with KD=3 nM. We characterized structure-activity relationships within this polymer, revealing side chains at specific positions that are critical to target-binding activity. Evo5 potently inhibits binding between PCSK9 and the LDL receptor.

Collectively, these findings represent the first laboratory evolution of functional, genetically encoded sequence-defined synthetic polymers without the constraints imposed by polymerases or ribosomes. The DNA-templated, ligase-based translation system developed here supports many rounds of iterated selection of polymers with diverse side-chains, including side-chains that mimic and extend beyond the repertoire of amino acid side-chains found in proteins. Both the PCSK9-binding and IL-6-binding polymers generated in this system exhibit position-dependent and side-chain dependent structure-activity relationships resembling those of proteins. Finally, it is noted that the PCSK9-binding polymers generated in this work depend on the presence of multiple side-chains with different physical properties, consistent with the importance of chemical diversity to the functional potential of these polymers.

Recently, Gawande and coworkers performed selections for PCSK9 aptamers from modified DNA libraries in which all instances of one or both pyrimidines (C and/or T) were replaced by side-chain-functionalized variants (27). High-affinity aptamers with dissociation constants similar to those of FDA-approved anti-PCSK9 monoclonal antibodies (evolocumab, KD=8.0 pM49, and alirocumab, KD=0.58 nM50) were enriched from doubly modified libraries in which hydrophobic or phenolic side chains were present on 50% of the nucleobases on average. Aptamers enriched from singly modified libraries (25% hydrophobic side chains on average) were less potent (KD≥100 pM), while libraries containing hydrophilic side chains or consisting of unmodified DNA did not produce aptamers with KD≤30 nM. Consistent with their findings, the highest affinity binders from our HFNAP library, which contains a roughly equal mix of hydrophilic and hydrophobic side chains installed at 33% total frequency, has KD=3 nM to PCSK9. We note, though, that different modifications may be suitable for other applications, as demonstrated by DNA-based catalysts functionalized with nitrogen nucleophiles as side-chains (29-33, 35). Therefore, the diverse, balanced set of side-chains in HFNAPs, similar to the natural repertoire of proteins, may be more versatile in other settings.

The ligase-based polymerization method allows straightforward redesign of the genetic code of the polymer, as it was exploited to expand the sequence and structural diversity of the polymers used in this work compared with those of another system (39). This feature also enables researchers to generate and select HFNAPs with side-chains tailored toward specific applications, as recently demonstrated by Hili and coworkers for scaffolding peptides on a DNA template(51). Moreover, the side-chain flexibility of this polymer evolution system raises the possibility of performing parallel evolution experiments with libraries of different side-chain compositions to shed light on the fundamental relationship between the structure of the building blocks in a genetic code and the evolutionary potential of the resulting polymers.

Methods

Additional experimental procedures and characterization data are provided herein.

Synthesis of HFNAP by Templated Translation Via DNA Ligase-Mediated Polymerization DNA template [up to 10 pmol, either in solution or immobilized on MyOne Streptavidin C1 magnetic beads (ThermoFisher Scientific)], polymerization initiation and termination primers (1.5 equivalents each relative to template), functionalized trinucleotide building blocks (10 equivalents relative to template for each occurrence of the corresponding codon) and 10× T4 RNA ligase reaction buffer (New England Biolabs; 1 μL) were mixed in a total volume of 8 μL in a PCR tube. The mixture was subjected to the following temperature program on a thermocycler: 95° C. for 10 sec; 65° C. for 4 min; a ramp from 65° C. to 4° C. at 0.1° C. per 10 s. To the PCR tube were added 1 μL of 10 mM ATP and 1 μL of T3 DNA ligase (New England Biolabs). The reaction was incubated at 4° C. for 12 h and then at 16° C. for 2 h.

Selections of HFNAP that Bind Protein Targets

Selection bait was prepared by immobilizing recombinant protein onto AminoLink Plus aldehyde-functionalized agarose resin via reductive amination with a MicroLink Protein Coupling Kit (ThermoFisher Scientific). Loading was 1 mg PCSK9 protein (ACROBiosystems) per mL resin for the initial PCSK9 binder selection and the first two rounds of PCSK9 binder re-selection; 150 μg PCSK9 per mL resin for rounds 3-5 of the re-selection; 40 μg protein per mL resin for round 6 of the re-selection; and 250 μg IL-6 protein (PeproTech) per mL resin throughout the IL-6 binder selection.

To initiate the selection, primer extension was performed with a biotinylated primer on 5 pmol of the sense strand randomized DNA library (Integrated DNA Technologies or TriLink BioTechnologies) with Klenow (exo-) polymerase (New England Biolabs). Biotinylated species was captured on streptavidin magnetic beads, which were then washed three times with 20 mM NaOH and then twice with 1× T4 RNA ligase reaction buffer. The bead-immobilized template strand library was then translated in a ligase-mediated polymerization to produce HFNAPs. The beads were suspended in 20 mM NaOH to denature the HFNAP-template hybrids. HFNAP strands in the supernatant were cleaned up with a MinElute column (Qiagen).

The HFNAP library was added to DPBS (with calcium and magnesium; Lonza) supplemented with BSA (0.1 mg/ml final) and Tween-20 (0.01% final), and then incubated with PCSK9 resin in a micro-spin filtration column (Pierce) at room temperature for 1 h on a rotor. (The amounts of resin-bound protein used in each round of the PCSK9 selection are indicated in FIG. 2b. Throughout the IL-6 selection, 240 pmol of immobilized IL-6 protein was used in each round.) The flow-through was collected by centrifugation at 1000 g into an Eppendorf tube. The beads were washed three times with 50 μL each of DPBS. The column was cut open, and the beads were collected by centrifugation into an Eppendorf tube and then incubated in 50 μL of lithium dodecyl sulfate (LDS) loading buffer (Life Technologies) at 95° C. for 15 min. After cooling, HFNAP strands were isolated from the mixture by cleaning up with a QiaQuick column (Qiagen), eluting the HFNAP into 50 μL of water.

Samples of 1 μL each from the flow-through, the three washes, and the elution were quantified by qPCR (20 μL reaction volume) using the iTaq Supermix (Bio-rad). The number of cycles for the qPCR curve of the elution sample to reach the end of exponential growth was used as the number of cycles for the preparative PCR (400 μL reaction volume split into 8×50 μL) of the selection elution pool (20 μL) with Q5 Hot Start High-Fidelity 2× Master Mix (New England Biolabs), using a biotinylated primer for the strand that will serve as translation template. The PCR product was cleaned up with a MinElute column and PAGE purified on a non-denaturing 10% TBE gel. A portion (indicated in FIG. 2b) of the dsDNA product was captured on streptavidin magnetic beads to initiate the next round of selection.

Surface Plasmon Resonance (SPR) Assays

All SPR assays were performed at 25° C. on a Biacore X100 or Biacore T200 (GE Healthcare Life Sciences). Binding kinetics between enzymatically synthesized biotinylated HFNAPs and unlabeled recombinant proteins were measured using single-cycle kinetics with the Biotin CAPture kit (GE Life Sciences) using 0.9×HBS-EP buffer (GE Life Sciences) at a flow rate of 30 μL/min. The injected PCSK9 concentration ranged from 10 to 300 nM for PCSK9-A5 and its variants, or from 2 to 60 nM for PCSK9-Evo5 and its variants. The injected IL-6 concentration ranged from 10 to 300 nM.

Binding kinetics between chemically synthesized PCSK9-Evo5-syn and biotinylated Avi-tagged PCSK9 (ACROBiosystems) were measured using single-cycle kinetics on a Series S SA chip (GE Life Sciences) using 0.9×HBS-EP buffer at a flow rate of 30 μL/min. The injected PCSK9-Evo5-syn concentration ranged from 1.8 to 180 nM.

Binding of PCSK9 on surface-immobilized LDLR in the presence of various competing agents was measured on a Series S SA chip using 10 mM HEPES, 150 mM NaCl, 0.1 mM $CaCl_2$), 0.005% Tween-20, pH 7.5 as bulk buffer at a flow rate of 10 μL/min. The injected solutions contained 20 nM PCSK9 and various competing agents ranging from 2 to 200 nM.

Data Availability

The principal data supporting the findings of this work are available within the figures and information provided herein. Additional data that support the findings of this study are available from the authors on request.

REFERENCES AND NOTES

1. Ellington, A. D. & Szostak, J. W. In vitro selection of RNA molecules that bind specific ligands. Nature 346, 818-822 (1990).
2. Tuerk, C. & Gold, L. Systematic evolution of ligands by exponential enrichment: RNA ligands to bacteriophage T4 DNA polymerase. Science 249, 505-510 (1990).
3. Robertson, D. L. & Joyce, G. F. Selection in vitro of an RNA enzyme that specifically cleaves single-stranded DNA. Nature 344, 467-468 (1990).
4. Bock, L. C., Griffin, L. C., Latham, J. A., Vermaas, E. H. & Toole, J. J. Selection of single-stranded DNA molecules that bind and inhibit human thrombin. Nature 355, 564-566 (1992).
5. Ellington, A. D. & Szostak, J. W. Selection in vitro of single-stranded DNA molecules that fold into specific ligand-binding structures. Nature 355, 850-852 (1992).
6. Breaker, R. R. & Joyce, G. F. A DNA enzyme that cleaves RNA. Chem. Biol. 1, 223-229 (1994).
7. Mattheakis, L. C., Bhatt, R. R. & Dower, W. J. An in vitro polysome display system for identifying ligands from very large peptide libraries. Proc. Natl. Acad. Sci. U.S.A. 91, 9022-9026 (1994).
8. Roberts, R. W. & Szostak, J. W. RNA-peptide fusions for the in vitro selection of peptides and proteins. Proc. Natl. Acad. Sci. U.S.A. 94, 12297-12302 (1997).
9. Nemoto, N., Miyamoto-Sato, E., Husimi, Y. & Yanagawa, H. In vitro virus: Bonding of mRNA bearing puromycin at the 3'-terminal end to the C-terminal end of its encoded protein on the ribosome in vitro. FEBS Lett. 414, 405-408 (1997).
10. Yamaguchi, J. et al. cDNA display: a novel screening method for functional disulfide-rich peptides by solid-phase synthesis and stabilization of mRNA-protein fusions. Nucleic Acids Res. 37, e108 (2009).

11. Brudno, Y. & Liu, D. R. Recent Progress Toward the Templated Synthesis and Directed Evolution of Sequence-Defined Synthetic Polymers. Chem. Biol. 16, 265-276 (2009).
12. Chaput, J. C., Yu, H. & Zhang, S. The Emerging World of Synthetic Genetics. Chem. Biol. 19, 1360-1371 (2012).
13. Pinheiro, V. B. & Holliger, P. The XNA world: progress towards replication and evolution of synthetic genetic polymers. Curr. Opin. Chem. Biol. 16, 245-252 (2012).
14. Pinheiro, V. B. & Holliger, P. Towards XNA nanotechnology: new materials from synthetic genetic polymers. Trends Biotechnol. 32, 321-328 (2014).
15. Hollenstein, M. Nucleoside Triphosphates Building Blocks for the Modification of Nucleic Acids. Molecules 17, 13569-13591 (2012).
16. Rogers, J. M. & Suga, H. Discovering functional, non-proteinogenic amino acid containing, peptides using genetic code reprogramming. Org. Biomol. Chem. 13, 9353-9363 (2015).
17. Yu, H., Zhang, S. & Chaput, J. C. Darwinian evolution of an alternative genetic system provides support for TNA as an RNA progenitor. Nat. Chem. 4, 183-187 (2012).
18. Pinheiro, V. B. et al. Synthetic Genetic Polymers Capable of Heredity and Evolution. Science 336, 341-344 (2012).
19. Taylor, A. I. et al. Catalysts from synthetic genetic polymers. Nature 518, 427-430 (2014).
20. Dunn, M. R. & Chaput, J. C. Reverse Transcription of Threose Nucleic Acid by a Naturally Occurring DNA Polymerase. ChemBioChem 17, 1804-1808 (2016).
21. Vaught, J. D. et al. Expanding the chemistry of DNA for in vitro selection. J. Am. Chem. Soc. 132, 4141-4151 (2010).
22. Gold, L. et al. Aptamer-Based Multiplexed Proteomic Technology for Biomarker Discovery. PLoS One 5, e15004 (2010).
23. Davies, D. R. et al. Unique motifs and hydrophobic interactions shape the binding of modified DNA ligands to protein targets. Proc. Natl. Acad. Sci. U.S.A. 109, 19971-19976 (2012).
24. Gupta, S. et al. Chemically-Modified DNA Aptamers Bind Interleukin-6 with High Affinity and Inhibit Signaling by Blocking its Interaction with Interleukin-6 Receptor. J. Biol. Chem. 289, 8706-8719 (2014).
25. Gelinas, A. D. et al. Crystal Structure of Interleukin-6 in Complex with a Modified Nucleic Acid Ligand. J. Biol. Chem. 289, 8720-8734 (2014).
26. Imaizumi, Y. et al. Efficacy of Base-Modification on Target Binding of Small Molecule DNA Aptamers. J. Am. Chem. Soc. 135, 9412-9419 (2013).
27. Gawande, B. N. et al. Selection of DNA aptamers with two modified bases. Proc. Natl. Acad. Sci. U.S.A. 114, 2898-2903 (2017).
28. Tolle, F., Brändle, G. M., Matzner, D. & Mayer, G. A Versatile Approach Towards Nucleobase-Modified Aptamers. Angew. Chem. Int. Ed. 54, 10971-10974 (2015).
29. Santoro, S. W., Joyce, G. F., Sakthivel, K., Gramatikova, S. & Barbas, C. F., III. RNA cleavage by a DNA enzyme with extended chemical functionality. J. Am. Chem. Soc. 122, 2433-2439 (2000).
30. Perrin, D. M., Garestier, T. & Héléne, C. Expanding the catalytic repertoire of nucleic acid catalysts: simultaneous incorporation of two modified deoxyribonucleoside triphosphates bearing ammonium and imidazolyl functionalities. Nucleosides Nucleotides 18, 377-391 (1999).
31. Perrin, D. M., Garestier, T. & Héléne, C. Bridging the Gap between Proteins and Nucleic Acids: A Metal-Independent RNAseA Mimic with Two Protein-Like Functionalities. J. Am. Chem. Soc. 123, 1556-1563 (2001).
32. Lermer, L., Roupioz, Y., Ting, R. & Perrin, D. M. Toward an RNaseA mimic: A DNAzyme with imidazoles and cationic amines. J. Am. Chem. Soc. 124, 9960-9961 (2002).
33. Hollenstein, M., Hipolito, C. J., Lam, C. H. & Perrin, D. M. A self-cleaving DNA enzyme modified with amines, guanidines and imidazoles operates independently of divalent metal cations (M2+). Nucleic Acids Res. 37, 1638-1649 (2009).
34. Shoji, A., Kuwahara, M., Ozaki, H. & Sawai, H. Modified DNA Aptamer That Binds the (R)-Isomer of a Thalidomide Derivative with High Enantioselectivity. J. Am. Chem. Soc. 129, 1456-1464 (2007).
35. Sidorov, A. V., Grasby, J. A. & Williams, D. M. Sequence-specific cleavage of RNA in the absence of divalent metal ions by a DNAzyme incorporating imidazolyl and amino functionalities. Nucleic Acids Res. 32, 1591-1601 (2004).
36. Sefah, K. et al. In vitro selection with artificial expanded genetic information systems. Proc. Natl. Acad. Sci. U.S.A. 111, 1449-1454 (2014).
37. Zhang, L. et al. Evolution of functional six-nucleotide DNA. J. Am. Chem. Soc. 137, 6734-6737 (2015).
38. Kimoto, M., Yamashige, R., Matsunaga, K., Yokoyama, S. & Hirao, I. Generation of high-affinity DNA aptamers using an expanded genetic alphabet. Nat. Biotechnol. 31, 453-457 (2013).
39. Hili, R., Niu, J. & Liu, D. R. DNA ligase-mediated translation of DNA into densely functionalized nucleic acid polymers. J. Am. Chem. Soc. 135, 98-101 (2013).
40. Lei, Y., Kong, D. & Hili, R. A High-Fidelity Codon Set for the T4 DNA Ligase-Catalyzed Polymerization of Modified Oligonucleotides. ACS Comb. Sci. 17, 716-721 (2015).
41. Cohen, J. C., Boerwinkle, E., Mosley, T. H., Jr. & Hobbs, H. H. Sequence Variations in PCSK9, Low LDL, and Protection against Coronary Heart Disease. N. Engl. J. Med. 354, 1264-1272 (2006).
42. Lambert, G., Charlton, F., Rye, K.-A. & Piper, D. E. Molecular basis of PCSK9 function. Atherosclerosis 203, 1-7 (2009).
43. Stein, E. A. et al. Effect of a Monoclonal Antibody to PCSK9 on LDL Cholesterol. N. Engl. J. Med. 366, 1108-1118 (2012).
44. Brudno, Y., Birnbaum, M. E., Kleiner, R. E. & Liu, D. R. An in vitro translation, selection and amplification system for peptide nucleic acids. Nat. Chem. Biol. 6, 148-155 (2010).
45. Zuker, M. Mfold web server for nucleic acid folding and hybridization prediction. Nucleic Acids Res. 31, 3406-3415 (2003).
46. Ortigao, J. F. R. et al. Antisense Effect of Oligodeoxynucleotides with Inverted Terminal Internucleotidic Linkages: A Minimal Modification Protecting against Nucleolytic Degradation. Antisense Res. Dev. 2, 129-146 (1992).
47. Lo Surdo, P. et al. Mechanistic implications for LDL receptor degradation from the PCSK9/LDLR structure at neutral pH. EMBO Rep. 12, 1300-1305 (2011).
48. Hunter, C. A. & Jones, S. A. IL-6 as a keystone cytokine in health and disease. Nat. Immunol. 16, 448-457 (2015).

49. Gibbs, J. P. et al. Impact of Target-Mediated Elimination on the Dose and Regimen of Evolocumab, a Human Monoclonal Antibody Against Proprotein Convertase Subtilisin/Kexin Type 9 (PCSK9). J. Clin. Pharmacol. 57, 616-626 (2017).
50. Kühnast, S. et al. Alirocumab inhibits atherosclerosis, improves the plaque morphology, and enhances the effects of a statin. J. Lipid Res. 55, 2103-2112 (2014).
51. Guo, C., Watkins, C. P. & Hili, R. Sequence-Defined Scaffolding of Peptides on Nucleic Acid Polymers. J. Am. Chem. Soc. 137, 11191-11196 (2015).

Materials and Methods

General Information

Unless otherwise specified, all materials and compounds were prepared using commercially available reagents from Sigma-Aldrich, and used without further purification. Water was purified with a Milli-Q purification system. DNA oligonucleotides without nucleobase side chain functional groups were purchased from Integrated DNA Technologies (IDT) unless noted otherwise. In-house synthesis of side-chain-functionalized DNA was performed on a PerSeptive Biosystems Expedite 8909 DNA synthesizer and purified by reverse-phase high-pressure liquid chromatography (HPLC, Agilent 1200) using a C18 stationary phase (Waters XBridge Prep C18, 5 m, 10×250 mm) and an acetonitrile/100 mM triethylammonium acetate gradient. All materials and reagents used for oligonucleotide synthesis were purchased from Glen Research, Berry & Associates, or ChemGenes, or custom synthesized by WuXi AppTec. Oligonucleotide and protein concentrations were quantified by UV spectroscopy using a Nanodrop ND1000 spectrophotometer, using extinction coefficients calculated with the IDT Oligo Analyzer and Expasy ProtParam web servers, respectively. Non-commercial oligonucleotides were characterized at the Harvard FAS Small Molecule Mass Spectrometry Facility by ESI-MS on a Bruker Impact II q-TOF mass spectrometer equipped with an Agilent 1290 uHPLC using flow injection analysis. Polyacrylamide gels were purchased from Bio-Rad. Sanger sequencing was performed by Eton BioSciences and analyzed with ApE—A plasmid Editor. Quantitative polymerase chain reactions (qPCRs) were performed on a Bio-rad CFX96 system. Deep sequencing was performed on an Illumina MiSeq. Surface plasmon resonance (SPR) analysis was carried out on a Biacore X100 or Biacore T200 (GE Healthcare Life Sciences). Time-resolved FRET assays were performed on a Tecan Infinite M1000 PRO microplate reader.

Oligonucleotide Sequences

All occurrences of U below are 2'-deoxy-U. Commercially available oligonucleotide modifiers are denoted by shorthand notations used by IDT.

Evaluation of Translation Yield on Template Libraries

| Name | Sequence |
|---|---|
| Template-11codon | CGTACGGTCGACGCTAGCNNRNNRNNRNNRNNR NNRNNRNNRNNRNNRNNRCACGTGGAGCTCGGA TCC (SEQ ID NO: 1) |
| Template-13codon | CGTACGGTCGACGCTAGCNNRNNRNNRNNRNNR NNRNNRNNRNNRNNRNNRNNRNNRCACGTGGAG CTCGGATCC (SEQ ID NO: 2) |
| Template-15codon | CGTACGGTCGACGCTAGCNNRNNRNNRNNRNNR NNRNNRNNRNNRNNRNNRNNRNNRNNRNNRCAC GTGGAGCTCGGATCC (SEQ ID NO: 3) |
| pp1-library | /5Phos/GCTAGCGTCGACCGTACG (SEQ ID NO: 4) |
| pp2-library | GGATCCGAGCTCCACGTG (SEQ ID NO: 5) |

Validation of Sequence Specificity of Translation and Amplification

| Name | Sequence |
|---|---|
| Template-Bt-CATA | /52-Bio//iSp18/CGTACGGTCGACGCTAG CTTGAAAGTGCAAGAGACACCGCGACACGTGG AGCTCGGATCC (SEQ ID NO: 6) |
| Template-Bt-CBTB | /52-Bio//iSp18/CGTACGGTCGACGCTAG CATGTTACTGGTATCGTGAGCGGGACACGTGG AGCTCGGATCC (SEQ ID NO: 7) |
| Template-Bt-CCTC | /52-Bio//iSp18/CGTACGGTCGACGCTAG CTAGATATGGCTAGGGTCAAGGGCACACGTGG AGCTCGGATCC (SEQ ID NO: 8) |
| Template-Bt-CDTD | /52-Bio//iSp18/CGTACGGTCGACGCTAG CAAGTAACAGGAAACGAGACGGCCACACGTGG AGCTCGGAUCC (SEQ ID NO: 9) |
| pp1-library-T7 | /5Phos/GCTAGCGTCGACCGTACGAGCGTCG CTACGCGTGAC (SEQ ID NO: 10) |
| pp2-library | GGATCCGAGCTCCACGTG (SEQ ID NO: 11) |
| T7-out-PCR2 | TAATACGACTCACTATAGGGCTCGATTTAATT TCGCCGACGTGATGACATTCCAGGCAGTGTCA CGCGTAGCGACGCT (SEQ ID NO: 12) |

PCSK9 Binder Selection and Evolution

| Name | Sequence |
|---|---|
| Naive library AZ15 | CGA ATC AGA TTG GAC CAG YNN YNN YNN YNN YNN YNN YNN YNN YNN YNN YNN YNN YNN YNN YNN GAG TCC AGA TGT AGG TAG (SEQ ID NO: 13) |
| BtBt-ExtA | /52-Bio//iSp18/CTA CCT ACA TCT GGA CTC (SEQ ID NO: 14) |
| ExtA | CTA CCT ACA TCT GGA CTC (SEQ ID NO: 15) |
| pp1A | /5Phos/GAG TCC AGA TGT AGG TAG (SEQ ID NO: 16) |
| pp2Z | CGA ATC AGA TTG GAC CAG (SEQ ID NO: 17) |
| MiSeqA | ACA CTC TTT CCC TAC ACG ACG CTC TTC CGA TCT NNNN CTA CCT ACA TCT GGA CTC (SEQ ID NO: 18) |
| MiSeqZ | TGG AGT TCA GAC GTG TGC TCT TCC GAT CT NNNN CGA ATC AGA TTG GAC CAG (SEQ ID NO: 19) |
| IlluminaAdapterFwd | AATGATACGGCGACCACCGAGATCTACAC [8-base barcode]ACACTCTTTCCCTA CACGAC (SEQ ID NO: 20) |
| IlluminaAdapterRev | CAAGCAGAAGACGGCATACGAGAT[8-base barcode]GTGACTGGAGTTCAGACGTGTGC T (SEQ ID NO: 21) |

| Name | Sequence |
|---|---|
| Rediv library AZ15 | CGA ATC AGA TTG GAC CAG XZP XFO JPZ JFP JOZ JOZ JPZ XFO JOO JFZ XZZ XFF XPZ XOO XOF GAG TCC AGA TGT AGG TAG (SEQ ID NO: 22)<br>X = 79% dC, 21% T<br>Z = 7% dA, 79% dC, 7% dG, 7% T<br>P = 79% dA, 7% dC, 7% dG, 7% T |

| Name | Sequence |
|---|---|
| | F = 7% dA, 7% dC, 79% dG, 7% T<br>O = 7% dA, 7% dC, 7% dG, 79% T<br>J = 21% dC, 79% T |
| pp1A-3ddC | /5Phos/GAG TCC AGA TGT AGG TAG/3ddC/ (SEQ ID NO: 23) |

Synthesis of Putative PCSK9 Binders for Bead Retention Assay

| Name | Sequence |
|---|---|
| pp1A | /5Phos/GAG TCC AGA TGT AGG TAG (SEQ ID NO: 16) |
| pp2Z | CGA ATC AGA TTG GAC CAG (SEQ ID NO: 17) |
| PCSK9A1-BtTempl | /52-Bio//iSp18/CTA CCT ACA TCT GGA CTC CAG AAG GTG ATG CAA AGG CAA ACG GTA GGA GAG AGA ATA TAG TGG CTG GTC CAA TCT GAT TCG (SEQ ID NO: 24) |
| PCSK9A1-DNA | CGA ATC AGA TTG GAC CAG CCA CTA TAT TCT CTC TCC TAC CGT TTG CCT TTG CAT CAC CTT CTG GAG TCC AGA TGT AGG TAG (SEQ ID NO: 25) |
| PCSK9A2-BtTempl | /52-Bio//iSp18/CTA CCT ACA TCT GGA CTC TCA GCG CAG AAG GTG AGG GCA AAA CGT GAA GAA TCA TTG TTG CTG GTC CAA TCT GAT TCG (SEQ ID NO: 26) |
| PCSK9A2-DNA | CGA ATC AGA TTG GAC CAG CAA CAA TGA TTC TTC TAC CGT TTT TGC CCT CAC CTT CTG CGC TGA GAG TCC AGA TGT AGG TAG (SEQ ID NO: 27) |
| PCSK9A3-BtTempl | /52-Bio//iSp18/CTA CCT ACA TCT GGA CTC TGA TCA GGA TAA GTA GTG CTA AAG ACA TGA AAG AGG TTG TAG AGA CTG GTC CAA TCT GAT TCG (SEQ ID NO: 28) |
| PCSK9A3-DNA | CGA ATC AGA TTG GAC CAG TCT CTA CAA CCT CTT TCA TGT CTT TAG CAC TAC TTA TCC TGA TCA GAG TCC AGA TGT AGG TAG (SEQ ID NO: 29) |
| PCSK9A4-BtTempl | /52-Bio//iSp18/CTA CCT ACA TCT GGA CTC GAA TAG GTA CCG CTA AAG ACG TGA TAG AAA CGA AAA GCA TTG GGG CTG GTC CAA TCT GAT TCG (SEQ ID NO: 30) |
| PCSK9A4-DNA | CGA ATC AGA TTG GAC CAG CCC CAA TGC TTT TCG TTT CTA TCA CGT CTT TAG CGG TAC CTA TTC GAG TCC AGA TGT AGG TAG (SEQ ID NO: 31) |
| PCSK9A5-BtTempl | /52-Bio//iSp18/CTA CCT ACA TCT GGA CTC CAG AAG GTG CCG GGG GCA AAA CGT GAA GAA TCA GTA ACG TGG CTG GTC CAA TCT GAT TCG (SEQ ID NO: 32) |
| PCSK9A5-DNA | CGA ATC AGA TTG GAC CAG CCA CGT TAC TGA TTC TTC TAC CGT TTT TGC CCC GGC AC CTT CTG GAG TCC AGA TGT AGG TAG (SEQ ID NO: 33) |
| PCSK9A6-BtTempl | /52-Bio//iSp18/CTA CCT ACA TCT GGA CTC GGA ACA ACG CAG AAG GAG CCG TGG AGA AGG CAG AAG AGG TTG AAA CTG GTC CAA TCT GAT TCG (SEQ ID NO: 34) |
| PCSK9A6-DNA | CGA ATC AGA TTG GAC CAG TTT CAA CCT CTT CTG CCT TCT CCA CGG CTC CTT CTG CGT TGT TCC GAG TCC AGA TGT AGG TAG (SEQ ID NO: 35) |
| PCSK9A7-BtTempl | /52-Bio//iSp18/CTA CCT ACA TCT GGA CTC CAG AAG GTG AAA GTA AGA GAA CAA ACG GTA GAG GAA TAG GGA AGA CTG GTC CAA TCT GAT TCG (SEQ ID NO: 36) |
| PCSK9A7-DNA | CGA ATC AGA TTG GAC CAG TCT TCC CTA TTC CTC TAC CGT TTG TTC TCT TAC TTT CAC CTT CTG GAG TCC AGA TGT AGG TAG (SEQ ID NO: 37) |

Synthesis of Biotinylated PCSK9-A5 and Variants for Surface Plasmon Resonance Assay

| Name | Sequence |
| --- | --- |
| pp1A | /5Phos/GAG TCC AGA TGT AGG TAG (SEQ ID NO: 16) |
| BtBt-pp2Z | /52-Bio//iSp18/CGA ATC AGA TTG GAC CAG (SEQ ID NO: 38) |
| PCSK9A5-Templ | CTA CCT ACA TCT GGA CTC CAG AAG GTG CCG GGG GCA AAA ACG GTA GAA GAA TCA GTA ACG TGG CTG TCA AAT CTG ATT CG (SEQ ID NO: 39) |

Synthesis of Biotinylated PCSK9-Evo5 and Variants for Surface Plasmon Resonance Assay

| Name | Sequence |
| --- | --- |
| pp1A-3primeStBt | /5Phos/GAG TCC AGA TGT AGG TAG/iSp18/iBiodT/3Bio/ (SEQ ID NO: 40) |
| pp1A-3primeStBt-14nt | /5Phos/GAG TCC AGA TGT AG/i5p18/iBiodT/3Bio/ (SEQ ID NO: 41) |
| Evo5-pp2-dU | CCA CGT TAC TGA TTC UGC (SEQ ID NO: 42) |
| PCSK9Evo5-Templ | CTA CCT ACA TCT GGA CTC CAG AAG GTG GCA GGG TAA ACA ACG GTA GCA GAA TCA GTA ACG TGG (SEQ ID NO: 43) |

Synthesis of PCSK9-Evo5-Fluor and Negative Control for EMSA Assay

| Name | Sequence |
| --- | --- |
| pp1A-Alexa647 | /5phos/*GAG TCC AGA TGT AGG TAG*/iSp18//3AlexF647N/ (SEQ ID NO: 44) |
| Evo_5 DNA-LeftHalf | *TGCTACCGTTGTTTACCCTGCCACCTTCTG* (SEQ ID NO: 45) |
| BtBt_Evo5-Template | /52-Bio//iSp18/*CTA CCT ACA TCT GGA CTC CAG AAG GTG GCA GGG TAA ACA ACG GTA GCA GAA TCA GTA ACG TGG CTG* (SEQ ID NO: 46) |

Negative Control for PCSK9-Evo5-Syn SPR Assay

| Name | Sequence |
| --- | --- |
| Evo5DNA-InvdT | TGC TAC CGT TGT TTA CCC TGC CAC CTT CTG GAG TCC AGA TGT AGG TAG/3InvdT/ (SEQ ID NO: 47) |

IL-6 Binder Selection

| Name | Sequence |
| --- | --- |
| Naïve library CW15 | CTC GGA TGA ACC TGG ACT YNN YNN YNN YNN YNN YNN YNN YNN YNN YNN YNN YNN YNN YNN GGA CTG AGT CCA GAG TAA (SEQ ID NO: 48) |

| Name | Sequence |
| --- | --- |
| BtBt-ExtC | /52-Bio//i5p18/TTA CTC TGG ACT CAG TCC (SEQ ID NO: 49) |
| ExtC | TTA CTC TGG ACT CAG TCC (SEQ ID NO: 50) |
| pp1C | /5Phos/GGA CTG AGT CCA GAG TAA (SEQ ID NO: 51) |
| pp2W | CTC GGA TGA ACC TGG ACT (SEQ ID NO: 52) |
| MiSeqC | ACA CTC TTT CCC TAC ACG ACG CTC TTC CGA TCT NNNNNN TTA CTC TGG ACT CAG TCC (SEQ ID NO: 53) |
| MiSeqW | TGG AGT TCA GAC GTG TGC TCT TCC GAT CT NNNN CTC GGA TGA ACC TGG ACT (SEQ ID NO: 54) |
| IlluminaAdapterFwd | AATGATACGGCGACCACCGAGATCTACAC [8-base barcode]ACACTCTTTCCCT ACACGAC (SEQ ID NO: 55) |
| IlluminaAdapterRev | CAAGCAGAAGACGGCATACGAGAT[8-base barcode]GTGACTGGAGTTCA GACGTGTGCT (SEQ ID NO: 56) |

Synthesis of Putative IL-6-Binding HFNAPs for Bead Retention Assay

| Name | Sequence |
| --- | --- |
| pp1C | /5phos/GGA CTG AGT CCA GAG TAA (SEQ ID NO: 51) |
| pp2W | CTC GGA TGA ACC TGG ACT (SEQ ID NO: 52) |
| IL6-A1-BtTempl | /52-Bio//iSp18/TTA CTC TGG ACT CAG TCC TGG TGG CCA CTG GCA GCA CCG TCA CGG AGG CTG AGA CTG CCG CAA AGT CCA GGT TCA TCC GAG (SEQ ID NO: 57) |
| IL6-A2-BtTempl | /52-Bio//iSp18/TTA CTC TGG ACT CAG TCC ACA GGA GGG ATA CCG AAA GGG CAA AGG CCG TAG CCA GAA CAA AAA AGT CCA GGT TCA TCC GAG (SEQ ID NO: 58) |
| IL6-A3-BtTempl | /52-Bio//iSp18/TTA CTC TGG ACT CAG TCC ACA ACG CAG CCG GAA GCA CCA CAG GAG AGG CGG TAA CCA GCA ACA AGT CCA GGT TCA TCC GAG (SEQ ID NO: 59) |
| IL6-A4-BtTempl | /52-Bio//iSp18/TTA CTC TGG ACT CAG TCC TCG GAA GCG TCA CGA CGG TAA CCG GCA CTG AGA GCA ACA CCA CAA AGT CCA GGT TCA TCC GAG (SEQ ID NO: 60) |
| IL6-A5-BtTempl | /52-Bio//iSp18/TTA CTC TGG ACT CAG TCC TGG CTA AGG CGA CCA GGG GCA CTG CAA CCA CGA CCA AAG GGG TGA AGT CCA GGT TCA TCC GAG (SEQ ID NO: 61) |
| IL6-A6-BtTempl | /52-Bio//iSp18/TTA CTC TGG ACT CAG TCC CAA TGA GGG AGA GAG GGG GAA GGG CGA CAA AGG CCG TAA CCA GGA AGT CCA GGT TCA TCC GAG (SEQ ID NO: 62) |
| IL6-A7-BtTempl | /52-Bio//iSp18/TTA CTC TGG ACT CAG TCC CCG GAG GAA TGA GTA CGA GGA AGG GCA ACG AAA TAA ACA GCA GCA AGT CCA GGT TCA TCC GAG (SEQ ID NO: 63) |

Synthesis of Biotinylated IL6-A7 and Variants for Surface Plasmon Resonance Assay

| Name | Sequence |
|---|---|
| pp1C-3ddC | /5Phos/GGACTGAGTCCAGAGTAA/3ddC/ (SEQ ID NO: 64) |
| BtBt-pp2W | /52-Bio//iSp18/CTCGGATGAACCTGGACT (SEQ ID NO: 65) |
| IL6-A7-Templ | TTA CTC TGG ACT CAG TCC CCG GAG GAA TGA GTA CGA GGA AGG GCA ACG AAA TAA ACA GCA GCA AGT CCA GGT TCA TCC GAG (SEQ ID NO: 66) |

Synthesis and Characterization of Phosphoramidite Intermediates

Compounds were prepared and characterized by Wuxi AppTec Co. under the direction of Xun Hong. The protocols and characterization furnished along with these compounds are printed here. NMR spectra were recorded on a Bruker Avance 400 MHz for $^1$H NMR. Chemical shifts are reported in ppm (S). Chromatographic purifications were by flash chromatography using 100~200 mesh silica gel. Anhydrous solvents were pre-treated with 3 Å MS column before use. All commercially available reagents were used as received unless otherwise stated.

General Synthetic Routes:

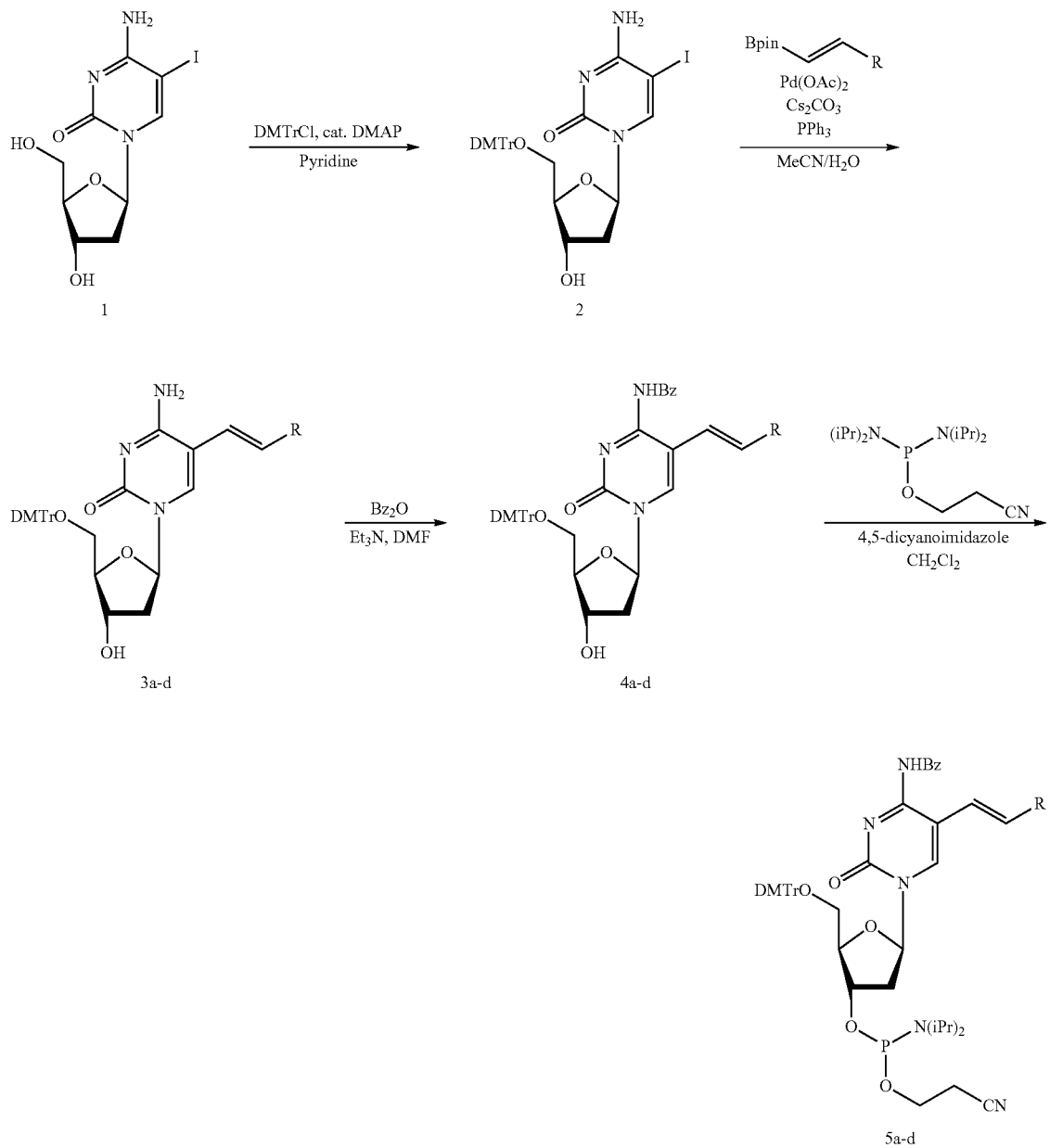

-continued
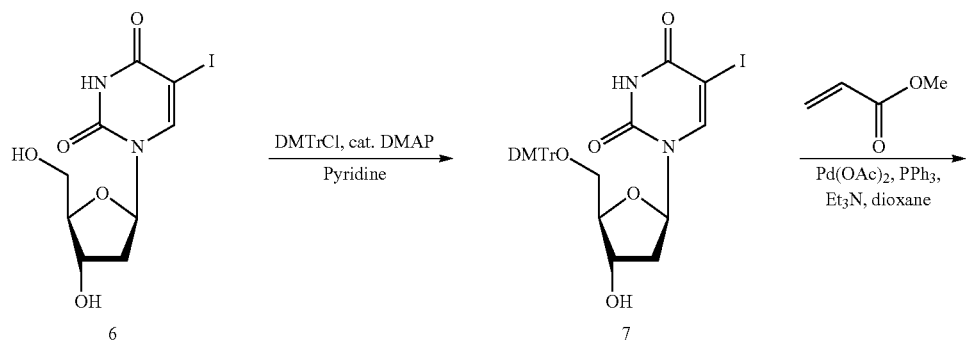
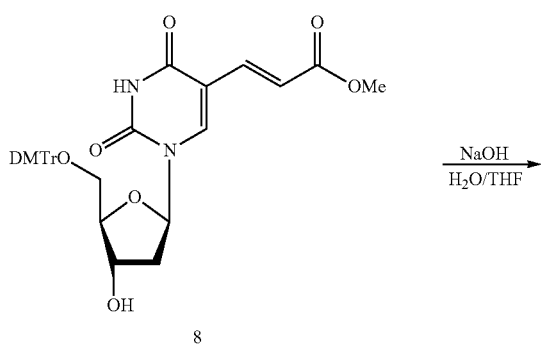
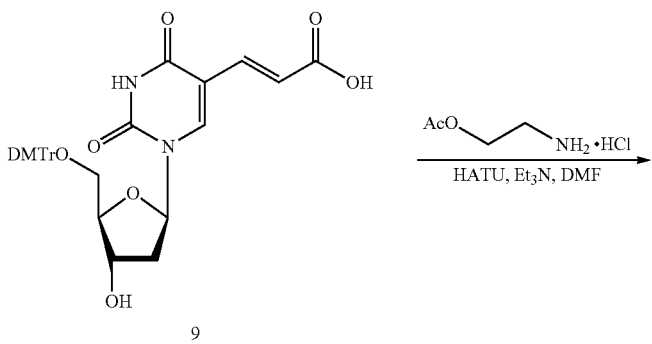
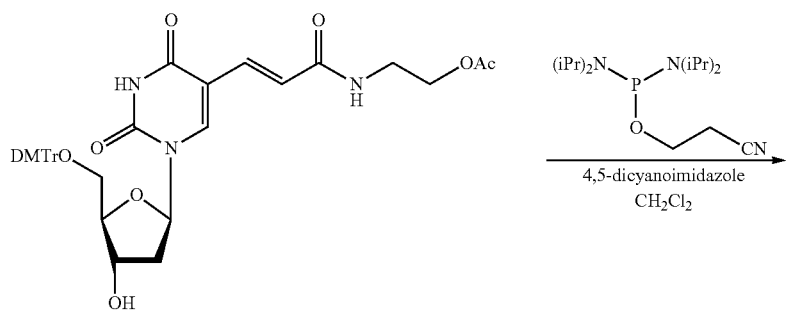

-continued
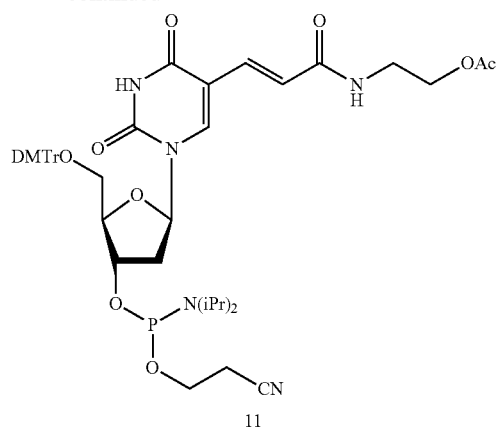
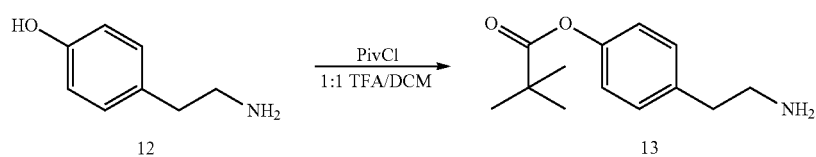
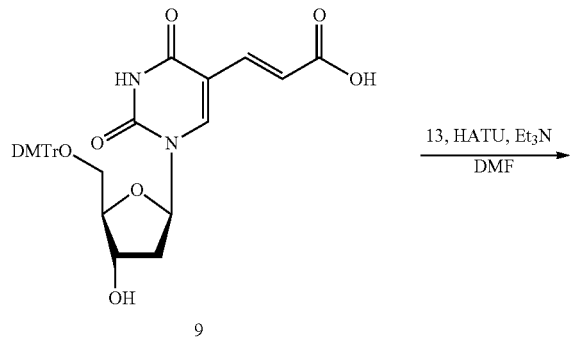
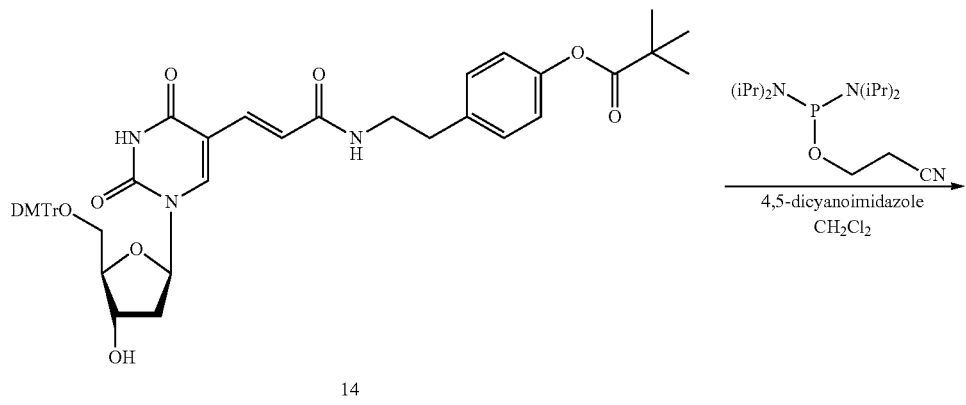

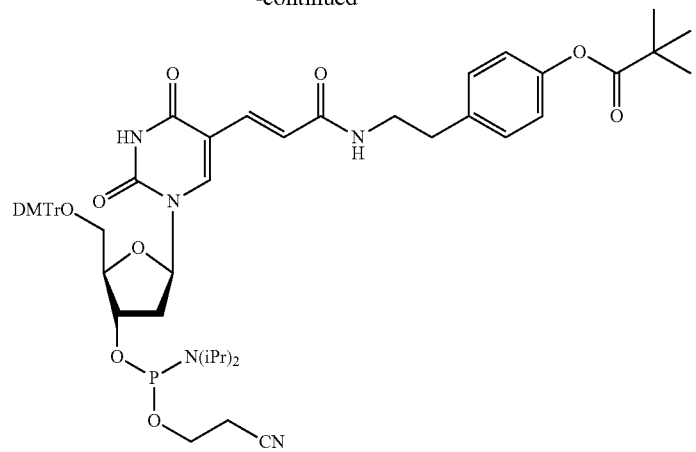

15

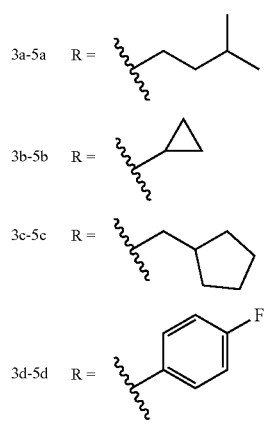

Synthesis of Phosphoramidites 5a-d

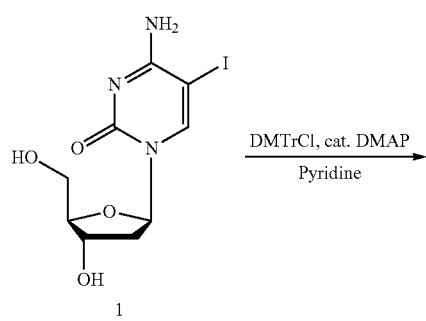

To a solution of 1 (40.0 g, 113.2 mmol, 1 equiv) and DMAP (0.113 g, 1.13 mmol, 0.01 equiv) in pyridine (400 mL) was added dropwise DMTrCl (40.2 g, 119 mmol, 1.05 equiv) and at 0° C. The mixture was stirred at 25° C. for 16 h. TLC (DCM/MeOH=20/1) indicated that 1 was consumed completely. The reaction mixture was concentrated with MeOH (50 mL) under reduced pressure to remove pyridine. The residue was purified by column chromatography (SiO$_2$, DCM/MeOH=50/1 to 20/1) to give the 2 (62 g, yield 84%) as a white foam. $^1$H NMR (400 MHz, DMSO-d$_6$) δ 8.65 (d, J=4.02 Hz, 1H), 7.99 (s, 1H), 7.53 (dd, J=7.28, 5.77 Hz, 1H), 7.36-7.42 (m, 2H), 7.20-7.35 (m, 6H), 6.90 (d, J=9.03 Hz, 4H), 6.09 (t, J=6.78 Hz, 1H), 4.15-4.24 (m, 1H), 3.91 (d, J=3.51 Hz, 1H), 3.74 (s, 6H), 3.18 (d, J=3.01 Hz, 2H), 2.22 (ddd, J=13.30, 5.77, 3.01 Hz, 1H), 2.06-2.16 (m, 1H).

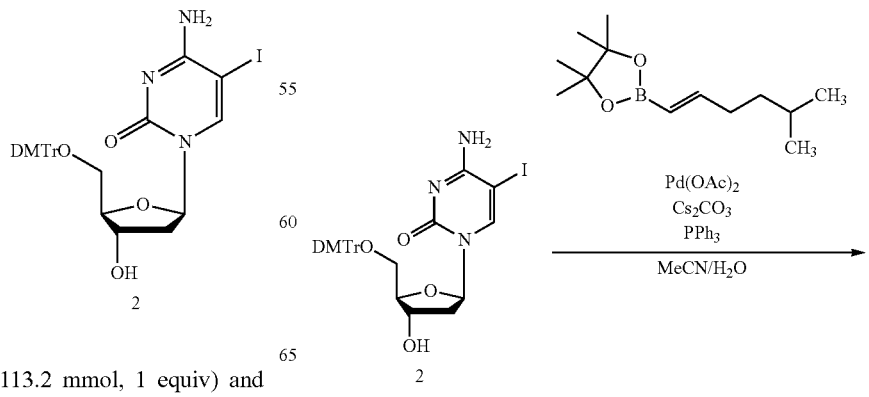

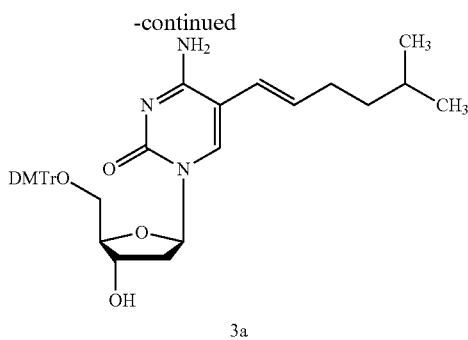

3a

To a solution of 2 (6 g, 9.15 mmol, 1 equiv), Cs$_2$CO$_3$ (8.95 g, 27.5 mmol, 3 equiv), (E)-4,4,5,5-tetramethyl-2-(5-methylhex-1-en-1-yl)-1,3,2-dioxaborolane (2.46 g, 11 mmol, 1.2 equiv) and PPh$_3$ (1.2 g, 4.58 mmol, 0.5 equiv) in dioxane (700 mL) and water (30 mL) was added Pd(OAc)$_2$ (2.35 g, 10.5 mmol, 0.1 equiv) at 25° C. under N$_2$ current. The mixture was heated to 90° C. and stirred for 16 h. TLC (ethyl acetate/MeOH=20/1) showed 2 was consumed completely. The reaction mixture was diluted with water 50 mL and extracted with ethyl acetate (100 mL×2). The combined organic layers were washed with sat. aqueous NaCl (50 mL), dried over MgSO$_4$, filtered and concentrated under reduced pressure to give a residue. The residue was purified by column chromatography (SiO$_2$, DCM/MeOH=50/1 to 20:1) to give compound 3a (5.1 g, 8.15 mmol, 89% yield) was obtained as a light-yellow solid. $^1$H NMR (400 MHz, CDCl$_3$) δ 7.86 (s, 1H), 7.42 (d, J=7.53 Hz, 2H), 7.18-7.35 (m, 7H), 6.81 (d, J=7.53 Hz, 4H), 6.46 (t, J=6.53 Hz, 1H), 5.53-5.70 (m, 2H), 4.47-4.57 (m, 1H), 4.13 (d, J=3.01 Hz, 1H), 3.79 (s, 5H), 3.47 (dd, J=10.54, 3.01 Hz, 1H), 3.28 (dd, J=10.54, 3.01 Hz, 1H), 2.70 (ddd, J=13.55, 5.52, 3.01 Hz, 1H), 2.24 (dt, J=13.55, 6.78 Hz, 1H), 1.56-1.83 (m, 4H), 1.13-1.40 (m, 3H), 0.91 (dtd, J=9.47, 6.43, 6.43, 3.26 Hz, 2H), 0.75 (dd, J=6.78, 2.76 Hz, 6H).

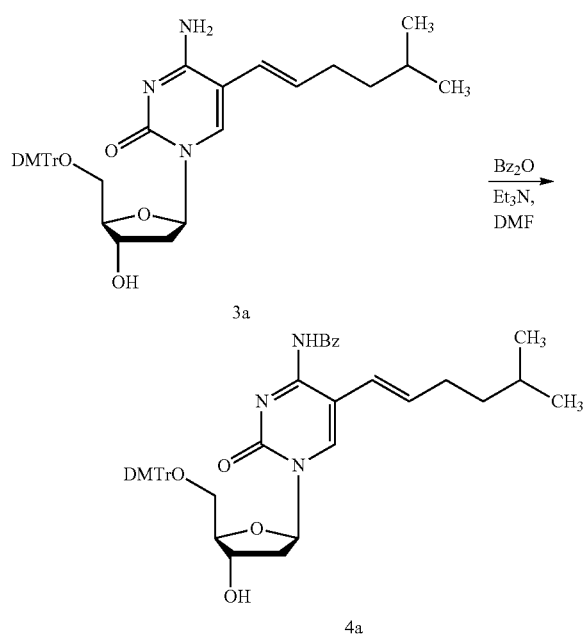

To a solution of 3a (4.23 g, 6.76 mmol, 1.00 equiv) in DMF (40.00 mL) was added Et$_3$N (1.03 g, 10.14 mmol, 1.41 mL, 1.50 equiv) and benzoic anhydride (1.84 g, 8.11 mmol, 1.53 mL, 1.20 equiv). The mixture was stirred at 0 to 25° C. for 16 h. TLC (petroleum ether/ethyl acetate=1/1) indicated 3a was consumed completely and the reaction was clean. The reaction mixture was quenched by addition water 20 mL at 0-5° C., and then extracted with ethyl acetate (50 mL). The combined organic layers were washed with sat. aqueous NaCl (20 mL), dried over MgSO$_4$, filtered and concentrated under reduced pressure to give a residue. The residue was purified by column chromatography (Basic SiO$_2$, petroleum ether/ethyl acetate=5/1 to 2/1) to a yellow solid. $^1$H NMR (400 MHz, CDCl$_3$) δ 13.52 (br. s., 1H), 8.30 (d, J=7.03 Hz, 2H), 7.96 (s, 1H), 7.50-7.57 (m, 1H), 7.40-7.50 (m, 4H), 7.21-7.37 (m, 7H), 6.84 (dd, J=8.53, 1.51 Hz, 4H), 6.40 (t, J=6.78 Hz, 1H), 6.21 (d, J=16.06 Hz, 1H), 5.92-6.03 (m, 1H), 4.55 (d, J=3.01 Hz, 1H), 4.10 (d, J=3.01 Hz, 1H), 3.79 (s, 6H), 3.56 (dd, J=10.54, 3.01 Hz, 1H), 3.31 (dd, J=10.54, 3.01 Hz, 1H), 2.52 (ddd, J=13.55, 5.77, 2.76 Hz, 1H), 2.35 (dt, J=13.68, 6.96 Hz, 1H), 2.09 (d, J=3.51 Hz, 1H), 1.72-1.91 (m, 2H), 1.41 (dt, J=13.43, 6.59 Hz, 1H), 0.83-1.00 (m, 2H), 0.77 (dd, J=6.53, 1.51 Hz, 6H).

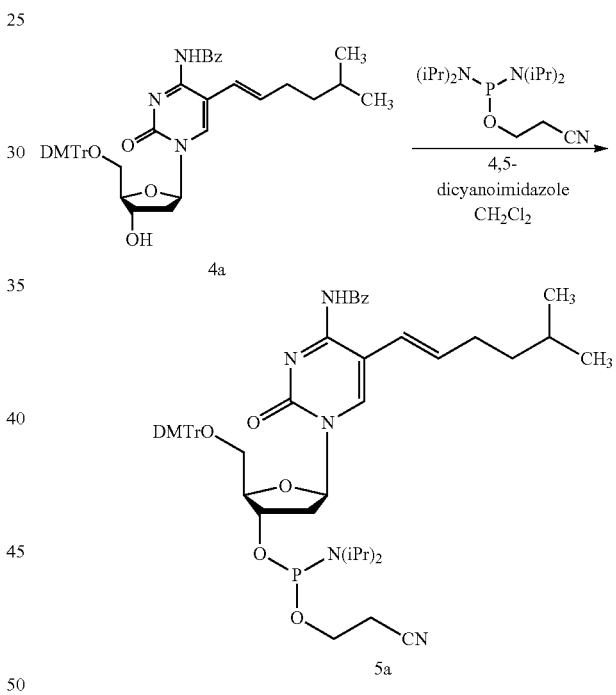

To a solution of 4a (2.87 g, 3.93 mmol, 1 equiv) and 4,5-dicyanoimidazole (0.696 g, 5.90 mmol, 1.5 equiv) in DCM (30 mL) was added drop wise of 3-bis(diisopropylamino) phosphanyloxypropanenitrile (1.42 g, 4.72 mmol, 1.2 equiv) at 0° C. under N$_2$ current. Then the mixture was stirred at 0-25° C. for 2 h under N$_2$ current. A clear yellow solution was obtained. TLC (petroleum ether/ethyl acetate=2/1) showed 4a was consumed completely. The reaction mixture was concentrated under reduced pressure to give a residue. The resulting residue was purified by column chromatography (basic SiO$_2$, petroleum ether/ethyl acetate=10/1 to 5/1) to give phosphoramidite 5a (1.75 g, 1.88 mmol, 48% yield) as a light-yellow foam. $^1$H NMR (400 MHz, CDCl$_3$) δ 13.51 (br. s., 1H) 8.30 (d, J=7.53 Hz, 2H) 7.99 (d, J=18.57 Hz, 1H) 7.50-7.58 (m, 1H) 7.41-7.50 (m, 4H) 7.21-7.37 (m, 8H) 6.84 (ddd, J=6.65, 4.64, 2.26 Hz, 4H) 6.36-6.48 (m, 1H) 6.18 (d, J=16.06 Hz, 1H) 5.88-6.02 (m, 1H) 4.62 (td, J=6.65, 3.26 Hz, 1H) 4.15-4.26 (m, 1H) 3.79 (d, J=2.51 Hz, 7H) 3.50-3.66 (m, 4H) 3.25 (dt, J=10.79, 3.39 Hz, 1H) 2.54-2.70 (m, 2H) 2.27-2.44 (m, 2H) 1.66-1.86 (m, 2H) 1.38 (dd, J=13.30, 6.78 Hz, 1H) 1.12-1.22 (m, 9H) 1.04 (d, J=7.03 Hz, 3H) 0.79-0.93 (m, 3H) 0.75 (t, J=5.77 Hz, 6H). $^{31}$P NMR (162 MHz, CDCl$_3$) δ 148.40-149.28 (m, 1 P). TLC petroleum ether/ethyl acetate=2/1 (R$_f$=0.43).

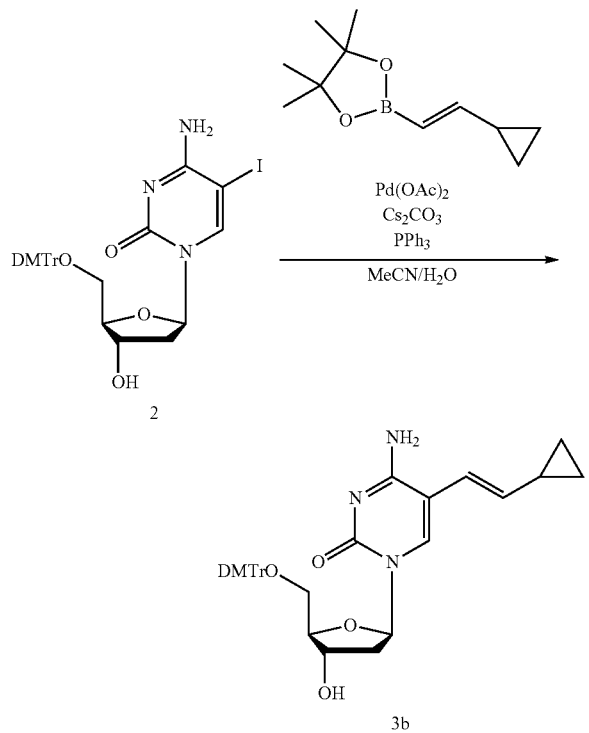

To a solution of 2 (8.00 g, 12.2 mmol, 1 equiv), Cs$_2$CO$_3$ (11.9 g, 36.6 mmol, 3 equiv), (E)-2-(2-cyclopropylvinyl)-4,4,5,5-tetramethyl-1,3,2-dioxaborolane (2.84 g, 14.7 mmol, 1.2 equiv) and PPh$_3$ (1.60 g, 6.10 mmol, 0.5 equiv) in dioxane (60 mL) and water (30 mL) was added Pd(OAc)$_2$ (0.274 g, 1.22 mmol, 0.1 equiv) at 25° C. under N$_2$ current. The mixture was heated to 90° C. and stirred for 16 h. TLC (ethyl acetate/MeOH=20/1) showed compound 2 was consumed completely. The reaction mixture was diluted with water 50 mL and extracted with ethyl acetate (100 mL×2). The combined organic layers were washed with sat. aqueous NaCl (50 mL), dried over MgSO$_4$, filtered and concentrated under reduced pressure to give a residue. The residue was purified by column chromatography (SiO$_2$, DCM/MeOH=50/1 to 20:1) to give 3b (7.00 g, 11.8 mmol, 96% yield), obtained as a light-yellow solid.

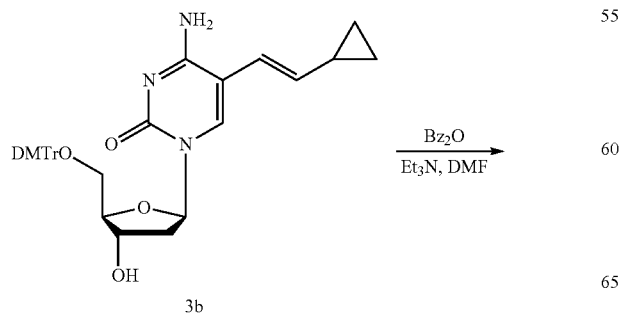

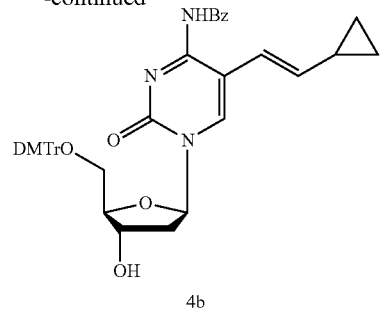

To a solution of 3b (3.4 g, 5.71 mmol, 1.00 equiv) in DMF (30.00 mL) was added Et$_3$N (0.693 g, 6.85 mmol, 1.50 equiv) and benzoic anhydride (1.42 g, 6.28 mmol, 1.20 equiv). The mixture was stirred at 0-25° C. for 16 h. TLC (DCM/MeOH=20/1) indicated 3b was consumed completely and the reaction was clean. The reaction mixture was quenched by addition sat. aqueous NaCl 20 mL at 25° C., and then extracted with ethyl acetate (50 mL). The combined organic layers were washed with sat. aqueous NaCl (20 mL), dried over MgSO$_4$, filtered and concentrated under reduced pressure to give a residue. The residue was purified by column chromatography (Basic SiO$_2$, petroleum ether/ethyl acetate=3/1 to 2:1) to give 4b (2.6 g, yield 66%) as a yellow solid. $^1$H NMR (400 MHz, CDCl$_3$) δ 13.53 (br. s., 1H), 8.29 (d, J=7.53 Hz, 2H), 7.92 (s, 1H) 7.50-7.57 (m, 1H), 7.41-7.49 (m, 4H), 7.21-7.37 (m, 8H), 6.85 (d, J=7.53 Hz, 4H), 6.39 (t, J=6.53 Hz, 1H), 6.30 (d, J=16.06 Hz, 1H), 5.60 (dd, J=15.56, 9.03 Hz, 1H), 4.48-4.56 (m, 1H), 4.08 (d, J=3.01 Hz, 1H), 3.80 (s, 6H), 3.56 (dd, J=10.54, 3.01 Hz, 1H), 3.28 (dd, J=10.79, 3.26 Hz, 1H), 2.51 (ddd, J=13.55, 6.02, 3.01 Hz, 1H), 2.32 (dt, J=13.93, 6.84 Hz, 1H), 2.19 (d, J=4.02 Hz, 1H), 1.28 (td, J=8.41, 4.77 Hz, 2H), 0.43-0.61 (m, 2H), −0.22-0.01 (m, 2H).

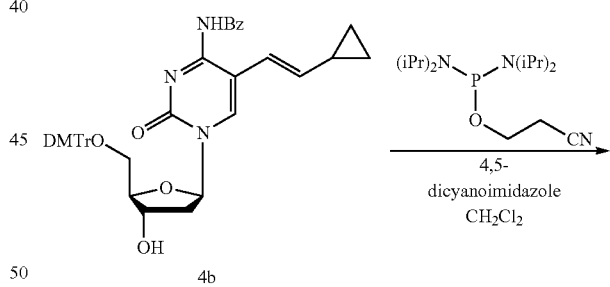

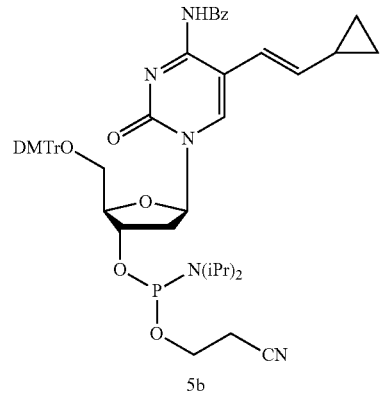

To a solution of 4b (2.25 g, 3.22 mmol, 1 equiv) and 4,5-dicyanoimidazole (0.570 g, 4.83 mmol, 1.5 equiv) in DCM (20 mL) was added dropwise of 3-bis(diisopropylamino) phosphanyloxypropanenitrile (1.16 g, 3.86 mmol, 1.2 equiv) at 0° C. under $N_2$ current. Then the mixture was stirred at 0-25° C. for 2 h under $N_2$ current. A clear yellow solution was obtained. TLC (DCM/MeOH=20/1) showed 4b was consumed completely. The reaction mixture was concentrated under reduced pressure to give a residue. The resulting residue was purified by column chromatography (basic $SiO_2$, petroleum ether/ethyl acetate=6/1 to 5/1) to give phosphoramidite 5b (2.20 g, 2.44 mmol, 75.9% yield) as a light-yellow foam. $^1$H NMR (400 MHz, $CDCl_3$) δ 13.53 (br. s., 1H) 8.29 (d, J=7.53 Hz, 2H) 7.95 (d, J=18.57 Hz, 1H) 7.50-7.57 (m, 1H) 7.41-7.49 (m, 4H) 7.21-7.38 (m, 7H) 6.85 (dd, J=7.53, 4.52 Hz, 4H) 6.36-6.46 (m, 1H) 6.28 (dd, J=15.81, 3.76 Hz, 1H) 5.57 (dd, J=15.81, 9.29 Hz, 1H) 4.59 (td, J=6.53, 3.01 Hz, 1H) 4.19 (dd, J=15.56, 2.01 Hz, 1H) 3.80 (d, J=2.51 Hz, 6H) 3.48-3.66 (m, 4H) 3.22 (dt, J=10.54, 3.01 Hz, 1H) 2.52-2.70 (m, 2H) 2.27-2.43 (m, 2H) 1.21-1.31 (m, 2H) 1.17 (dd, J=6.78, 2.76 Hz, 10H) 1.04 (d, J=6.53 Hz, 3H) 0.78-0.92 (m, 1H) 0.39-0.56 (m, 2H) −0.29−−0.08 (m, 2H). $^{31}$P NMR (162 MHz, $CDCl_3$) δ 148.36-149.25 (m, 1 P). TLC 20:1 DCM:methanol ($R_f$=0.85).

organic layers were washed with sat. aqueous NaCl (50 mL), dried over $MgSO_4$, filtered and concentrated under reduced pressure to give a residue. The residue was purified by column chromatography ($SiO_2$, DCM/MeOH=50/1 to 20:1) to give the 3c (4.90 g, 7.68 mmol, 83% yield) was obtained as a light-yellow solid. $^1$H NMR (400 MHz, $CDCl_3$) δ 7.82 (s, 1H), 7.43 (d, J=7.53 Hz, 2H), 7.19-7.36 (m, 8H), 6.82 (d, J=8.53 Hz, 4H), 6.52 (t, J=6.53 Hz, 1H), 5.55-5.69 (m, 2H), 4.46-4.55 (m, 1H), 4.16 (d, J=2.51 Hz, 2H), 3.72-3.84 (m, 6H), 3.45 (dd, J=10.04, 3.01 Hz, 1H), 3.29 (dd, J=10.29, 3.26 Hz, 1H), 3.09 (q, J=7.19 Hz, 1H), 2.74 (dt, J=10.79, 2.89 Hz, 1H), 2.21 (dt, J=13.80, 6.65 Hz, 1H), 1.72-1.86 (m, 2H), 1.35-1.59 (m, 9H), 0.92 (br. s., 2H).

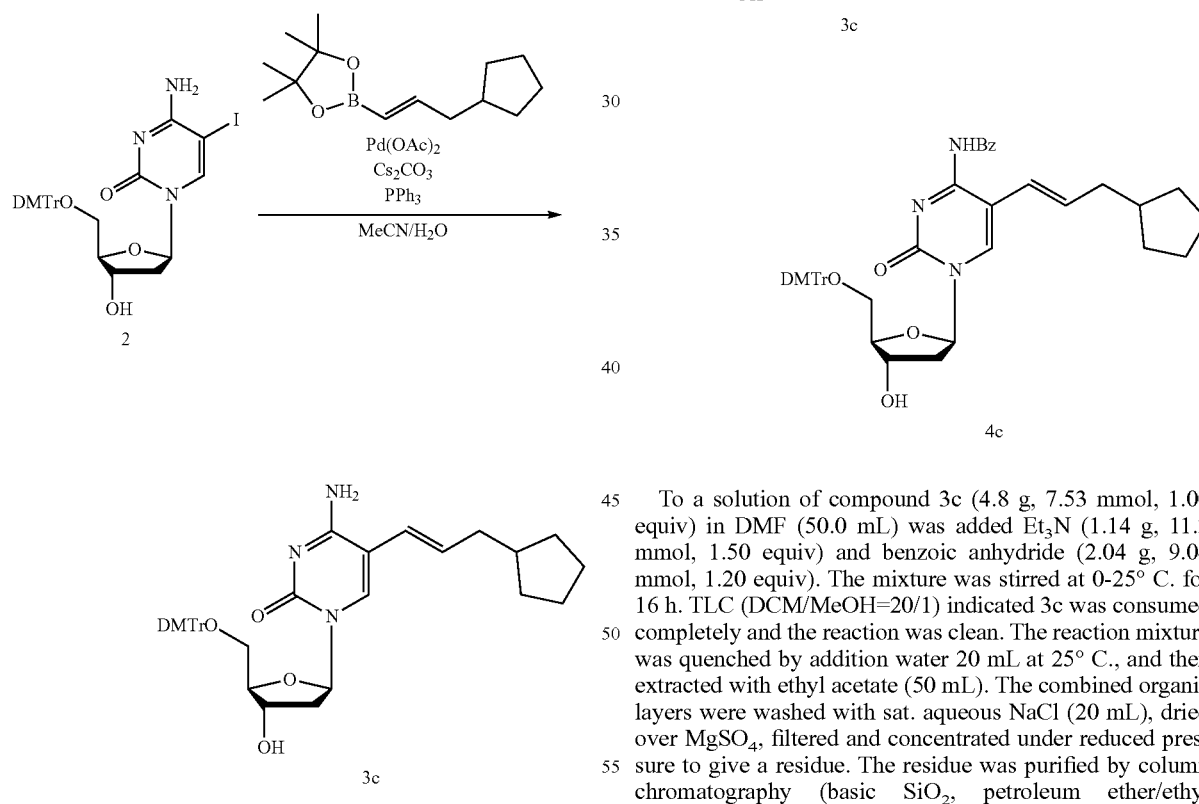

To a solution of 2 (6.00 g, 9.15 mmol, 1 equiv), $Cs_2CO_3$ (8.95 g, 27.5 mmol, 3 equiv), (E)-2-(2-cyclopropylvinyl)-4,4,5,5-tetramethyl-1,3,2-dioxaborolane (2.59 g, 11.0 mmol, 1.2 equiv) and $PPh_3$ (1.20 g, 4.58 mmol, 0.5 equiv) in dioxane (40 mL) and water (20 mL) was added $Pd(OAc)_2$ (0.274 g, 1.22 mmol, 0.1 equiv) at 25° C. under $N_2$ current. The mixture was heated to 90° C. and stirred for 16 h. TLC (DCM/MeOH=20/1) showed 2 was consumed completely. The reaction mixture was diluted with water (50 mL) and extracted with ethyl acetate (100 mL×2). The combined To a solution of compound 3c (4.8 g, 7.53 mmol, 1.00 equiv) in DMF (50.0 mL) was added $Et_3N$ (1.14 g, 11.3 mmol, 1.50 equiv) and benzoic anhydride (2.04 g, 9.04 mmol, 1.20 equiv). The mixture was stirred at 0-25° C. for 16 h. TLC (DCM/MeOH=20/1) indicated 3c was consumed completely and the reaction was clean. The reaction mixture was quenched by addition water 20 mL at 25° C., and then extracted with ethyl acetate (50 mL). The combined organic layers were washed with sat. aqueous NaCl (20 mL), dried over $MgSO_4$, filtered and concentrated under reduced pressure to give a residue. The residue was purified by column chromatography (basic $SiO_2$, petroleum ether/ethyl acetate=5/1 to 2:1) to give compound 4c (3.60 g, yield 64%) as a yellow solid. $^1$H NMR (400 MHz, $CDCl_3$) δ 13.52 (br. s., 1H), 8.30 (d, J=7.53 Hz, 2H), 7.90 (s, 1H), 7.50-7.57 (m, 1H), 7.40-7.48 (m, 4H), 7.20-7.37 (m, 8H), 6.84 (d, J=8.03 Hz, 4H), 6.39 (t, J=6.53 Hz, 1H), 6.13 (s, 2H), 4.51-4.58 (m, 1H), 4.10 (d, J=3.01 Hz, 1H), 3.79 (s, 6H), 3.53 (dd, J=10.54, 3.51 Hz, 1H), 3.33 (dd, J=10.54, 3.51 Hz, 1H), 2.52 (ddd, J=13.68, 5.90, 3.01 Hz, 1H), 2.33 (dt, J=13.55, 6.78 Hz, 1H), 2.18 (d, J=3.51 Hz, 1H), 1.79-1.94 (m, 2H), 1.37-1.61 (m, 7H), 1.00 (br. s., 2H). TLC DCM/MeOH=20/1 ($R_f$=0.43).

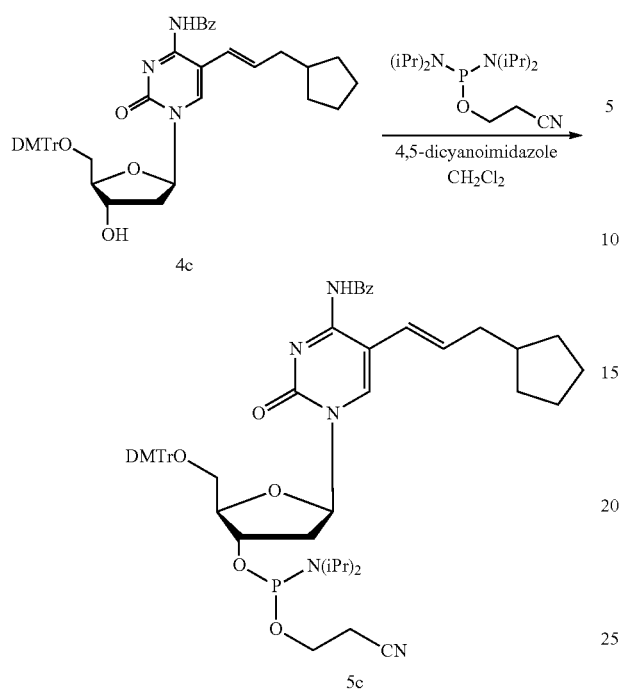

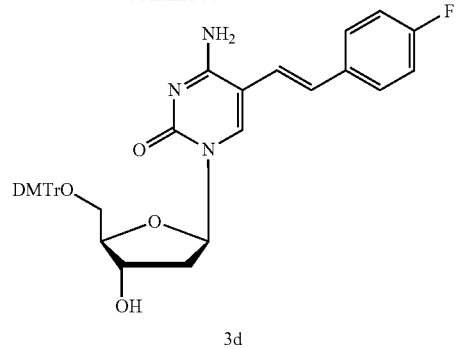

To a solution of 4c (2.40 g, 3.24 mmol, 1 equiv) and 4,5-dicyanoimidazole (0.574 g, 4.86 mmol, 1.5 equiv) in DCM (20 mL) was added dropwise of 3-bis(diisopropylamino) phosphanyloxypropanenitrile (1.17 g, 3.89 mmol, 1.2 equiv) at 0° C. under $N_2$ current. Then the mixture was stirred at 0-25° C. for 2 h under $N_2$ current. A clear yellow solution was obtained. TLC (petroleum ether/ethyl acetate=2/1) showed 4c was consumed completely. The reaction mixture was concentrated under reduced pressure to give a residue, which was purified by column chromatography (basic $SiO_2$, petroleum ether/ethyl acetate=10/1 to 6/1) to give phosphoramidite 5c (1.70 g, 2.44 mmol, 56% yield) as a white foam. $^1$H NMR (400 MHz, CDCl$_3$) δ 13.51 (br. s., 1H), 8.30 (d, J=7.03 Hz, 2H), 7.93 (d, J=18.57 Hz, 1H), 7.50-7.57 (m, 1H), 7.41-7.49 (m, 4H), 7.22-7.37 (m, 8H), 6.84 (dd, J=7.53, 5.02 Hz, 4H), 6.36-6.46 (m, 1H), 6.03-6.18 (m, 2H), 4.62 (td, J=6.78, 3.01 Hz, 1H), 4.16-4.26 (m, 1H), 3.79 (d, J=2.51 Hz, 6H), 3.49-3.66 (m, 4H), 3.27 (dt, J=10.54, 3.76 Hz, 1H), 2.53-2.70 (m, 2H), 2.27-2.44 (m, 2H), 1.72-1.91 (m, 2H), 1.35-1.56 (m, 6H), 1.14-1.23 (m, 9H), 1.05 (d, J=6.53 Hz, 2H), 0.97 (d, J=3.01 Hz, 3H). $^{31}$P NMR (162 MHz, CDCl$_3$) δ 148.49-149.26 (m, 1 P).

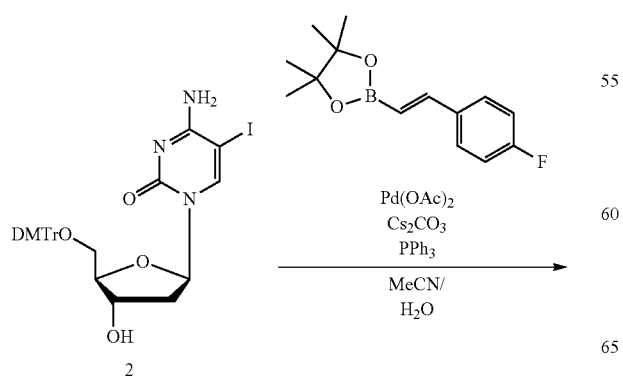

To a solution of 2 (6.00 g, 12.211.0 mmol, 1 equiv), Cs$_2$CO$_3$ (8.95 g, 27.5 mmol, 3 equiv), (E)-2-(4-fluorostyryl)-4,4,5,5-tetramethyl-1,3,2-dioxaborolane (2.72 g, 11.0 mmol, 1.2 equiv) and PPh$_3$ (1.20 g, 4.58 mmol, 0.5 equiv) in dioxane (60 mL) and water (30 mL) was added Pd(OAc)$_2$ (0.206 g, 0.915 mmol, 0.1 equiv) at 25° C. under N$_2$ current. The mixture was heated to 90° C. and stirred for 16 h. TLC (DCM/MeOH=20/1) showed 2 was consumed completely. The reaction mixture was diluted with water (50 mL) and extracted with ethyl acetate (100 mL×2). The combined organic layers were washed with sat. aqueous NaCl (50 mL), dried over MgSO$_4$, filtered and concentrated under reduced pressure to give a residue. The residue was purified by column chromatography (SiO$_2$, DCM/MeOH=50/1 to 20:1) to give 3d (3.10 g, 4.77 mmol, 52% yield) as a light-yellow solid. TLC DCM/MeOH=20/1 (R$_f$=0.20).

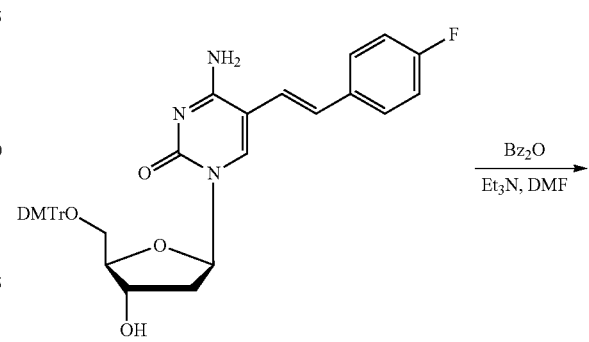

To a solution of 3d (2.7 g, 4.16 mmol, 1.00 equiv) in DMF (30.00 mL) was added Et$_3$N (0.631 g, 6.24 mmol, 1.50 equiv) and benzoic anhydride (1.13 g, 4.99 mmol, 1.20 equiv). The mixture was stirred at 0-25° C. for 16 h. TLC (petroleum ether/ethyl acetate=1/1) indicated 3d was consumed completely and the reaction was clean according to TLC. The reaction mixture was quenched by addition water 100 mL at 0-5° C., and then extracted with ethyl acetate (50 mL). The combined organic layers were washed with sat. aqueous NaCl (20 mL), dried over MgSO$_4$, filtered and concentrated under reduced pressure to give a residue. The residue was purified by column chromatography (basic SiO$_2$, petroleum ether/ethyl acetate=2/1 to 1:1) to give 4d (2.00 g, yield 64%) as a yellow solid. $^1$H NMR (400 MHz, CDCl$_3$) δ 13.59 (br. s., 1H), 8.32 (d, J=7.53 Hz, 2H), 8.22 (s, 1H), 7.52-7.59 (m, 1H), 7.42-7.51 (m, 4H), 7.33 (dd, J=8.78, 1.76 Hz, 4H), 7.22-7.29 (m, 3H), 7.14-7.21 (m, 1H), 7.05 (d, J=16.56 Hz, 1H), 6.71-6.89 (m, 9H), 6.43 (t, J=6.53 Hz, 1H), 4.58 (br. s., 1H), 4.15 (d, J=2.51 Hz, 1H), 3.59-3.75 (m, 7H), 3.29 (dd, J=11.04, 3.01 Hz, 1H), 2.59 (ddd, J=13.55, 6.02, 3.01 Hz, 1H), 2.41 (dt, J=13.55, 6.78 Hz, 1H), 2.14 (br. s., 1H); $^{19}$F NMR (376 MHz, CDCl$_3$) δ −114.32 (s, 1 F)

as a light-yellow foam. $^1$H NMR (400 MHz, CDCl$_3$) δ 13.59 (s, 1H), 8.33 (d, J=7.53 Hz, 2H), 8.25 (d, J=19.07 Hz, 1H), 7.52-7.59 (m, 1H), 7.41-7.51 (m, 4H), 7.22-7.38 (m, 7H), 7.18 (dd, J=7.03, 4.02 Hz, 1H), 7.03 (d, J=16.06 Hz, 1H), 6.66-6.85 (m, 9H), 6.45 (q, J=6.53 Hz, 1H), 4.65 (td, J=6.53, 3.01 Hz, 1H), 4.19-4.30 (m, 1H), 3.69 (s, 6H), 3.49-3.65 (m, 3H), 3.19-3.28 (m, 1H), 2.58-2.76 (m, 2H), 2.36-2.46 (m, 2H), 1.51 (d, J=6.53 Hz, 1H), 1.17 (d, J=7.03 Hz, 8H), 1.04 (d, J=6.53 Hz, 3H). $^{31}$P NMR (162 MHz, CDCl$_3$) δ 148.45-149.26 (m, 1 P). $^{19}$F NMR (376 MHz, CDCl$_3$) δ −114.45 (s, 1 F). TLC 2:1 pentane ether:ethyl acetate (R$_f$=0.43).

Synthesis of Phosphoramidite 11

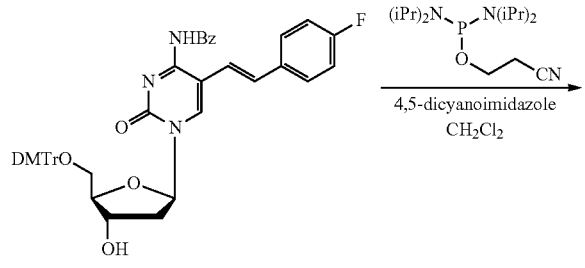

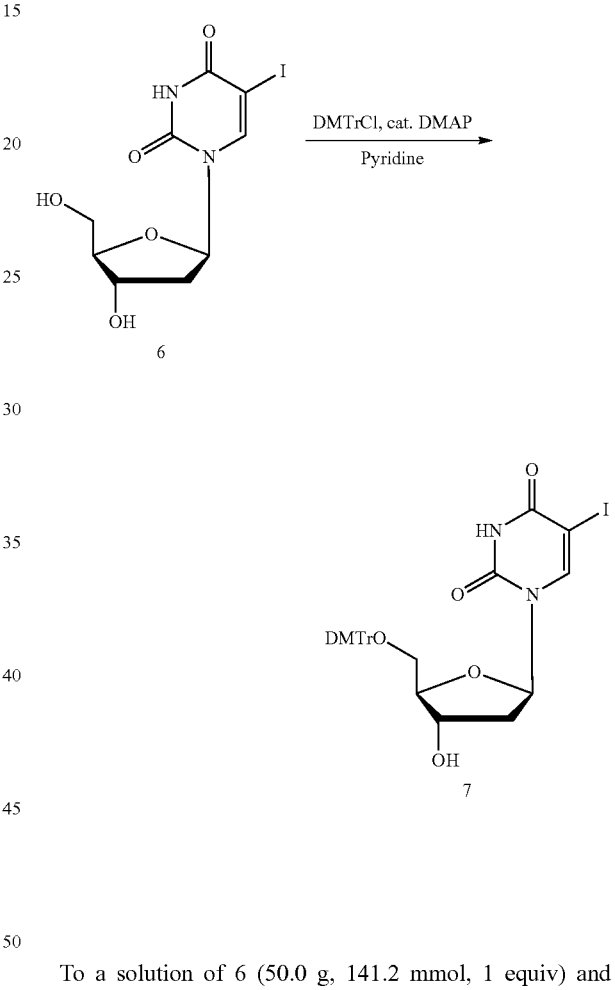

To a solution of 4d (2.30 g, 3.05 mmol, 1 equiv) and 4,5-dicyanoimidazole (0.570 g, 4.27 mmol, 1.5 equiv) in DCM (20 mL) was added drop wise of 3-bis(diisopropylamino) phosphanyloxypropanenitrile (1.10 g, 3.66 mmol, 1.2 equiv) at 0° C. under N$_2$ current. Then the mixture was stirred at 0-25° C. for 3 h under N$_2$ current. A clear yellow solution was obtained. TLC (petroleum ether/ethyl acetate=2/1) showed 4d was consumed completely. The reaction mixture was concentrated under reduced pressure to give a residue, which was purified by column chromatography (basic SiO$_2$, petroleum ether/ethyl acetate=6/1 to 5/1) to give phosphoramidite 5d (2.10 g, 2.20 mmol, 72% yield)

To a solution of 6 (50.0 g, 141.2 mmol, 1 equiv) and DMAP (0.172 g, 1.41 mmol, 0.01 equiv) in pyridine (500 mL) was added dropwise DMTrCl (50.2 g, 148.2 mmol, 1.05 equiv) and at 0° C. The mixture was stirred at 25° C. for 16 h. TLC (Petroleum ether/Ethyl acetate=1/1) indicated compound 6 was consumed completely. The reaction mixture was concentrated with MeOH (5 mL) under reduced pressure to remove pyridine. The residue was purified by column chromatography (SiO$_2$, petroleum ether/ethyl acetate=2/1 to 1/2) to give 7 (85.0 g, yield 92%) as a white foam. $^1$H NMR (400 MHz, CDCl$_3$) δ 8.16 (s, 1H), 7.44 (d, J=7.53 Hz, 2H), 7.22-7.38 (m, 7H), 6.87 (d, J=8.53 Hz, 4H), 6.35 (dd, J=7.78, 5.77 Hz, 1H), 4.53-4.62 (m, 1H), 4.11-4.18 (m, 2H), 3.81 (s, 6H), 3.35-3.48 (m, 2H), 2.53 (ddd, J=13.55, 5.52, 2.51 Hz, 1H), 2.26-2.37 (m, 1H). TLC petroleum ether/ethyl acetate=1/1 (R$_f$=0.15).

To a solution of 7 (68.7 g, 105 mmol, 1 equiv), methyl acrylate (54 g, 627 mmol, 2 equiv), PPh$_3$ (5.5 g, 20.9 mmol, 0.2 equiv), and trimethylamine (21.2 g, 209 mmol, 2 equiv) in dioxane (700 mL) was added Pd(OAc)$_2$ (2.35 g, 10.5 mmol, 0.1 equiv) at 25° C. under N$_2$ current. The mixture was heated to 90° C. and stirred for 16 h. TLC (petroleum ether/ethyl acetate=1/1) showed 7 was consumed completely. The reaction mixture was filtered under reduced pressure to give a residue. The residue was purified by column chromatography (SiO$_2$, petroleum ether/ethyl acetate=1/1 to 1.5:1) to give the compound 8 (42 g, 68.3 mmol, 65.3% yield) as a light-yellow solid.

To solution of 8 (42 g, 68.3 mmol, 1 equiv) in THF (500 mL) was added NaOH aqueous (1N, 102.5 mL, 1.5 equiv) at 25° C., and then the resulting mixture was stirred at 25° C. for 16 h. TLC (DCM/MeOH=10/1) indicated 8 was consumed completely. The reaction mixture was partitioned between ethyl acetate (200 mL) and water (100 mL), the water phase was separated, acidified with sat. aqueous citric acid to pH7, the white suspension was filtered and dried under reduced pressure to give the compound 9 (30.5 g, 50.8 mmol, 74% yield) as a white solid. $^1$H NMR (400 MHz, CDCl$_3$) δ 7.67 (s, 1H), 7.40 (d, J=7.53 Hz, 2H), 7.24-7.33 (m, 8H), 7.15-7.22 (m, 1H), 6.91 (d, J=15.56 Hz, 1H), 6.82 (d, J=9.04 Hz, 4H), 6.29 (t, J=6.27 Hz, 1H), 4.47 (d, J=6.02 Hz, 1H), 3.99 (d, J=5.02 Hz, 1H), 3.75 (s, 5H), 3.45 (dd, J=10.29, 5.27 Hz, 1H), 3.34 (dd, J=10.04, 4.52 Hz, 1H), 2.41-2.51 (m, 1H), 2.26 (dt, J=13.80, 6.65 Hz, 1H). TLC DCM/MeOH=10/1 (R$_f$=0.15).

A solution of 9 (5 g, 8.32 mmol, 1 equiv), Et$_3$N (4.21 g, 41.6 mmol, 5 equiv) and HATU (4.75 g, 12.5 mmol, 1.5 equiv) in DMF (60 mL) was stirred for 30 min at 25° C. Then to this mixture was added 2-aminoethyl acetate hydrochloride (1.39 g, 9.99 mmol, 1.2 equiv) at 25° C. The mixture was stirred at 25° C. for 16 h. TLC (DCM/MeOH=20/1) showed the acid was consumed completely.

The reaction mixture was quenched by addition of sat. aqueous NaHCO₃ (50 mL) at 25° C., and then extracted with ethyl acetate (100 mL×2). The combined organic layers were concentrated under reduced pressure to give a residue. The residue was purified by column chromatography (basic SiO₂, DCM/MeOH=50/1 to 30/1) to give compound 10 (2.7 g, yield 47%) as a white foam. TLC DCM/MeOH=20/1 (R$_f$=0.30).

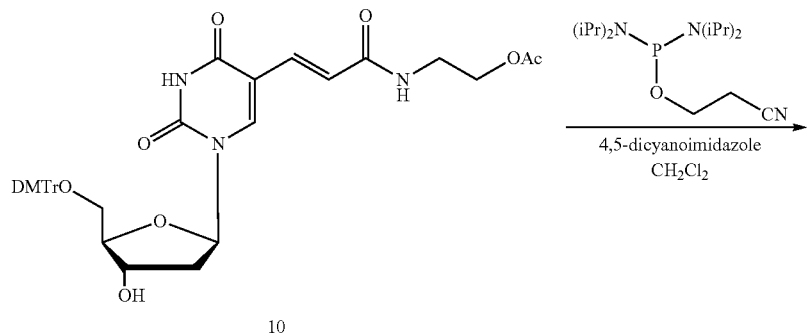

10

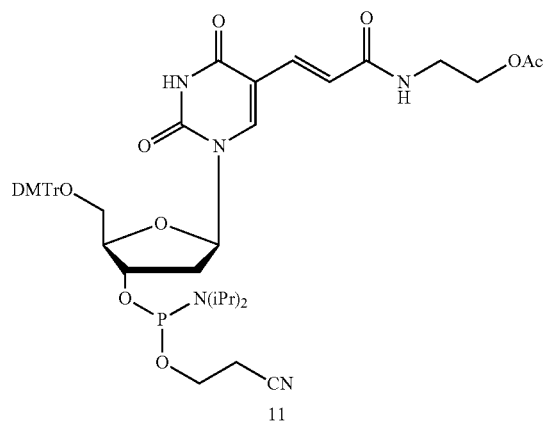

11

To a solution of 10 (2.10 g, 3.06 mmol, 1 equiv) and 4,5-dicyanoimidazole (0.543 g, 4.59 mmol, 1.5 equiv) in DCM (30 mL) was added drop wise of 3-bis(diisopropylamino)phosphanyloxypropanenitrile (1.11 g, 3.67 mmol, 1.2 equiv) at 0° C. under N₂ current. Then the mixture was stirred at 0-25° C. for 2 h under N₂ current. A clear yellow solution was obtained. TLC (DCM/MeOH=20/1) showed 10 was consumed completely. The reaction mixture was concentrated under reduced pressure to give a residue, which was purified by column chromatography (basic SiO₂, DCM/Acetone=15/1 to 8/1) to give phosphoramidite 11 (1.7 g, 1.44 mmol, 75% yield) as a white foam. ¹H NMR (400 MHz, CDCl₃) δ 7.79-7.90 (m, 1H) 7.43 (d, J=7.53 Hz, 2H), 7.20-7.36 (m, 7H), 7.04 (d, J=15.56 Hz, 1H), 6.82-6.92 (m, 4H), 6.71-6.80 (m, 1H), 6.28 (t, J=6.53 Hz, 1H), 5.41-5.55 (m, 1H), 4.57 (dt, J=6.53, 3.26 Hz, 1H), 4.18-4.29 (m, 1H), 4.07 (q, J=5.02 Hz, 2H), 3.79 (s, 6H), 3.54-3.70 (m, 3H), 3.39-3.51 (m, 3H), 3.28-3.37 (m, 1H), 2.55-2.80 (m, 2H), 2.45 (t, J=6.27 Hz, 1H), 2.28 (dt, J=13.68, 6.96 Hz, 1H), 2.06 (s, 3H), 1.25-1.31 (m, 1H), 1.18 (t, J=6.27 Hz, 9H), 1.09 (d, J=7.03 Hz, 2H).

Synthesis of Phosphoramidite 15

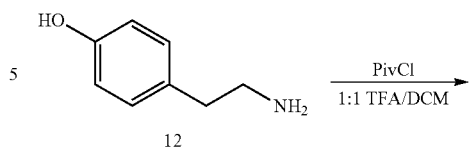

12

-continued

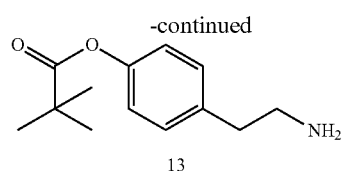

13

Pivaloyl chloride (7.25 g, 61.1 mmol, 1 equiv) was added drop wise to a solution of 4-(2-aminoethyl) phenol (7.5 g, 54.5 mmol, 1 equiv) in DCM (50 mL) and TFA (50 mL) at 25° C., then the resulting brown mixture was stirred for 12 h. LCMS showed reactant was consumed completely and one main peak with desired MS was detected. The reaction mixture was concentrated under reduced pressure to give a residue, which was purified by column chromatography (SiO₂, DCM:MeOH=20/1 to 1:1) to give compound 13 (9.5 g, 42.9 mmol, 79% yield) as a brown solid. ¹H NMR (400 MHz, CDCl₃) δ 7.21 (d, J=8.53 Hz, 2H), 6.95 (d, J=8.53 Hz, 2H), 3.18 (t, J=7.28 Hz, 2H), 2.90-2.99 (m, 2H), 1.34 (s, 9H). ¹⁹F NMR (376 MHz, CDCl₃) δ −75.82 (s, 1 F).

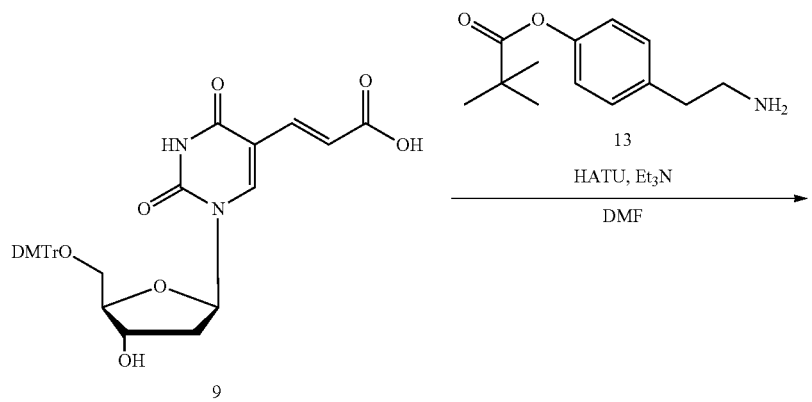

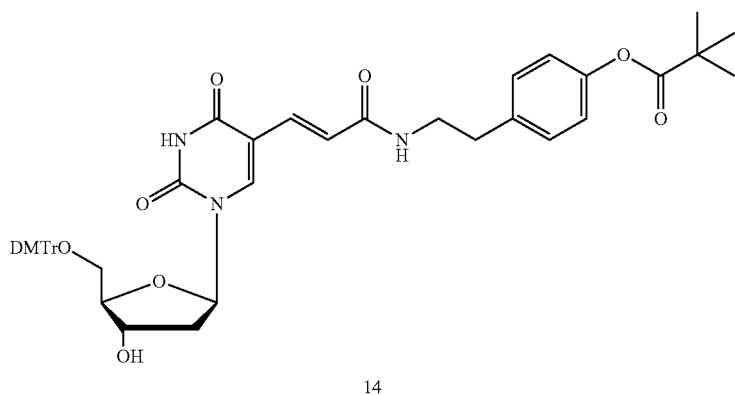

A solution of 9 (2.8 g, 4.66 mmol, 1 equiv), Et₃N (0.94 g, 9.32 mmol, 2 equiv) and HATU (3.54 g, 9.32 mmol) in DMF (50 mL) was stirred for 30 min at 25° C. Then to this mixture was added 13 (1.13 g, 5.13 mmol, 1.1 equiv) at 25° C. The mixture was stirred at 25° C. for 16 h. TLC (DCM/MeOH=20/1) showed the acid was consumed completely. The reaction mixture was concentrated under reduced pressure to remove solvents. The residue was purified by column chromatography (basic SiO₂, DCM/MeOH=20/1 to 10/1) to give compound 14 (2 g, yield 86%) as a white foam. TLC DCM/MeOH=20/1 ($R_f$=0.20).

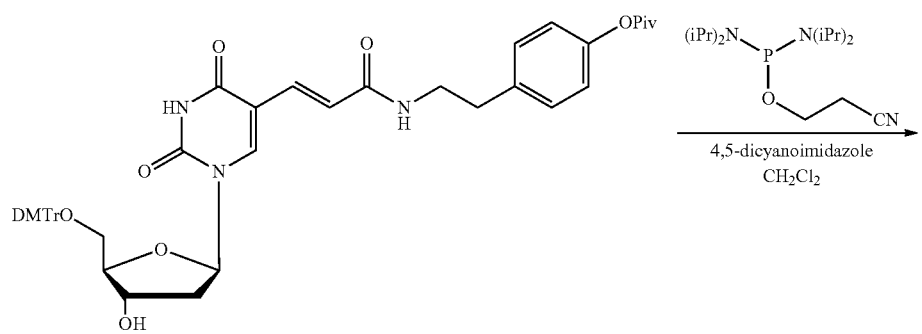

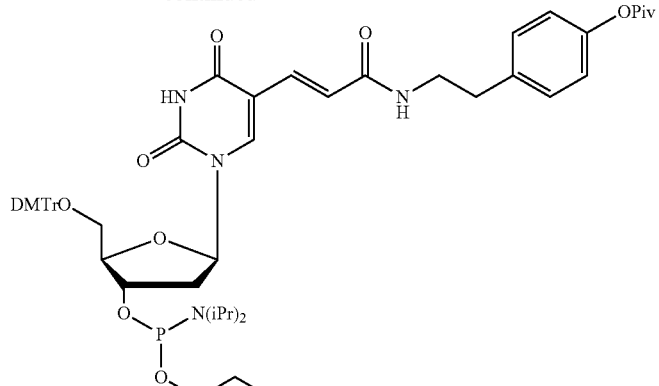

To a solution of 14 (2.90 g, 3.61 mmol, 1 equiv) and 4,5-dicyanoimidazole (0.639 g, 5.41 mmol, 1.5 equiv) in DCM (30 mL) was added drop wise of 3-bis(diisopropylamino)phosphanyloxypropanenitrile (1.30 g, 4.33 mmol, 1.2 equiv) at 0° C. under $N_2$ current. Then the mixture was stirred at 0-25° C. for 2 h under $N_2$ current. A clear yellow solution was obtained. TLC (DCM/MeOH=20/1) showed 14 was consumed completely. The reaction mixture was concentrated under reduced pressure to give a residue, which was purified by column chromatography (basic $SiO_2$, DCM/acetone=15/1 to 10/1) to give phosphoramidite 15 (1.95 g, 1.94 mmol, 54% yield) as a light-brown gum. $^1$H NMR (400 MHz, $CDCl_3$) δ 7.76-7.91 (m, 2H), 7.45 (d, J=6.02 Hz, 2H), 7.27-7.38 (m, 7H), 7.13-7.26 (m, 3H), 6.97-7.09 (m, 3H), 6.87 (dd, J=8.78, 3.76 Hz, 3H), 6.61 (dd, J=15.56, 11.04 Hz, 1H), 6.28-6.35 (m, 1H), 6.18 (s, 1H), 5.01-5.12 (m, 1H), 4.59 (br. s., 1H), 4.10-4.28 (m, 4H), 3.80 (s, 5H), 3.28-3.62 (m, 9H), 2.78 (td, J=6.15, 1.76 Hz, 3H), 2.60-2.72 (m, 10H), 2.45 (t, J=6.27 Hz, 1H), 2.28 (dt, J=12.92, 6.34 Hz, 1H), 1.37 (s, 7H), 1.30 (t, J=6.27 Hz, 15H), 1.16-1.22 (m, 7H), 1.09 (d, J=6.53 Hz, 3H). $^{31}$P NMR (162 MHz, $CDCl_3$) δ 148.76-149.28 (m, 1 P) 14.16 (s, 2 P).

Synthesis and Characterization of Functionalized Oligonucleotides.

Standard phosphoramidite reagents and 1000-A controlled-pore glass (CPG) supports for dA, Ac-dC, dmf-dG, and dT were purchased from Glen Research, as were chemical phosphorylation reagent II (10-1901) and the phosphoramidite for NHS-carboxy-dT (10-1535). The phosphoramidite reagent for the incorporation of the aminoallyl side-chain-functionalized nucleotide (BA 0311) was purchased from Berry and Associates, as was the perfluoroalkyl-DMT dT phosphoramidite (FL 1300). The phosphoramidite reagents for the incorporation of isopentyl (5a), cyclopropyl (5b), cyclopentyl (5c), fluorophenyl (5d), ethanolamine (11), and tyramine (15) side-chain-functionalized nucleotides were custom synthesized by WuXi AppTec as detailed in the previous section.

Solid-phase synthesis of side-chain-functionalized DNA was performed on a PerSeptive Biosystems Expedite 8909 DNA synthesizer. All side-chain-functionalized phosphoramidites were incubated with molecular sieves overnight before use. Syntheses were performed on 1-µmol columns using standard coupling cycles, except for 5'-phosphorylation, which required 7 minutes of coupling with chemical phosphorylation reagent II. When the histamine side-chain-functionalized nucleotide was called for, NHS-carboxy-dT was incorporated in its place, and after the full-length synthesis was completed, a solution of histamine (free base; 5 mg) and diisopropylethylamine (1 µl) in 200 µl of 10% DMSO in acetonitrile was manually injected into the column and allowed to react overnight, and then the column was washed with acetonitrile and dried. Similarly, when a methylamine-functionalized nucleotide was required (for probing side chain SAR; see FIG. 5), NHS-carboxy-dT was incorporated in its place, and methylamine (30 equiv. with respect to solid-phase synthesis scale, from a 2M stock in THF) and diisopropylethylamine (1 µl) in 200 µl of acetonitrile was added to the column and allowed to react overnight before washing and drying. The functionalized DNA was then deprotected and cleaved from solid support by incubation in 30% ammonium hydroxide overnight at room temperature. The phosphorylated trinucleotide building blocks were synthesized DMT-off and, after deprotection, cleavage, and evaporation of ammonium hydroxide, were purified by reverse-phase HPLC using a gradient of 0-20% acetonitrile in 0.1 M TEAA, pH 7, over 24 minutes, followed by 20-40% acetonitrile in 0.1 M TEAA, pH 7, over 10 minutes. The full length HFNAP Evo5-syn was synthesized DMT-on and the 5'-most nucleotide was incorporated with a perfluoroalkyl-DMT phosphoramidite (Berry and Associates, FL 1300). After deprotection/cleavage, the polymer was purified and deprotected on column with a fluorous phase purification cartridge (Fluoro-Pak II from Berry and Associates) according to manufacturer's instructions. (See FIG. 10 for synthetic scheme.) The Evo5-syn used for mass spectrometry characterization and for SPR experiments was further purified by denaturing PAGE on a 10% TBE-urea gel.

Mass Spectrometry Characterization of Chemically Synthesized Functionalized Oligonucleotides Oligonucleotide samples were analyzed in negative ion mode using a Bruker Impact II q-TOF mass spectrometer equipped with an Agilent 1290 uHPLC using flow injection analysis. The purified samples were introduced at a constant flow rate of 0.200 mL/minute using 50% acetonitrile and 0.1% formic acid. Each individual data file was calibrated for the m/z scale using a plug of sodium formate clusters introduced through a secondary isocratic pump and introduced using a 6-port valve. Using this internal calibration method, less than 2 ppm relative error was obtained on all samples. Bruker Data Analysis software was used to simulate the isotope pattern for each target ion.

| Name | Expected m/z ([M-2H]$^{2-}$) | Observed m/z | Expected m/z ([M-H]$^-$) | Observed m/z |
|---|---|---|---|---|
| phos-CAA-Isopentyl | 513.6257 | 513.6253 | 1028.2588 | 1028.2580 |
| phos-CAC-Isopentyl | 501.6201 | 501.6198 | 1004.2475 | 1004.2467 |
| phos-CTC-Isopentyl | 497.1143 | 497.1142 | 995.2360 | 995.2355 |
| phos-CGG-Isopentyl | 529.6207 | 529.6204 | 1060.2486 | 1060.2478 |
| phos-CAT-Fluorophenyl | 521.0918 | 251.0914 | 1043.1908 | 1043.1896 |
| phos-CAG-Fluorophenyl | 533.5950 | 533.5946 | 1068.1973 | 1086.1961 |
| phos-CGA-Fluorophenyl | 533.5950 | 533.5946 | 1068.1973 | 1068.1960 |
| phos-CGC-Fluorophenyl | 521.5894 | 521.5890 | 1044.1861 | 1044.1849 |
| phos-CTA-Cyclopropyl | 494.0965 | 494.0961 | 989.2003 | 989.1990 |
| phos-CCA-Cyclopropyl | 486.5967 | 486.5961 | 974.2006 | 974.1993 |
| phos-CCT-Cyclopropyl | 482.0909 | 482.0907 | 965.1890 | 965.1885 |
| phos-CCC-Cyclopropyl | 474.5910 | 474.5907 | 950.1894 | 950.1885 |
| phos-CTT-Cyclopentyl | 510.6142 | 510.6137 | 1022.2356 | 1022.2343 |
| phos-CTG-Cyclopentyl | 523.1174 | 523.1170 | 1074.2421 | 1047.2406 |
| phos-CGT-Cyclopentyl | 523.1174 | 523.1169 | 1047.2421 | 1047.2406 |
| phos-CCG-Cyclopentyl | 515.6176 | 515.6170 | 1032.2425 | 1032.2408 |
| phos-TTT-Phenol | 551.5987 | 551.5983 | — | — |
| phos-TTG-Phenol | 564.1020 | 564.1019 | 1129.2112 | 1129.2099 |
| phos-TGT-Phenol | 564.1020 | 564.1015 | 1129.2112 | 1129.2094 |
| phos-TCG-Phenol | 556.6021 | 556.6017 | 1114.2115 | 1114.2103 |
| phos-TAA-Imidazole | 547.6081 | 547.6079 | 1096.2234 | 1096.2227 |
| phos-TAC-Imidazole | 535.6025 | 535.6023 | 1072.2122 | 1072.2117 |
| phos-TCA-Imidazole | 535.6025 | 535.6021 | 1072.2122 | 1072.2113 |
| phos-TCC-Imidazole | 523.5969 | 523.5964 | 1048.2010 | 1048.1999 |
| phos-TAT-Primary alcohol | 518.0889 | 518.0883 | 1037.1850 | 1037.1837 |
| phos-TAG-Primary alcohol | 530.5921 | 530.5917 | 1062.1915 | 1062.1904 |
| phos-TGA-Primary alcohol | 530.5921 | 530.5917 | 1062.1915 | 1062.1903 |
| phos-TGC-Primary alcohol | 518.5865 | 518.5862 | 1038.1802 | 1039.1793 |
| phos-TTA-Allylamine | 489.0861 | 489.0857 | 979.1795 | 979.1786 |
| phos-TTC-Allylamine | — | — | 955.1683 | 955.1672 |
| phos-TCT-Allylamine | — | — | 955.1683 | 955.1673 |
| phos-TGG-Allylamine | 509.5868 | 509.5864 | 1020.1809 | 1020.1799 |

Mass spectrometry data for PCSK9-Evo5-syn are given in FIG. 11.

Additional Experimental Procedures

Isolation of Single-Stranded HFNAP by Templated Translation Via DNA Following Ligase-Mediated Polymerization To synthesize the double-stranded HFNAP-template hybrid, template (10 pmol), polymerization initiation and termination primers (15 pmol each), functionalized trinucleotide building blocks (100 pmol for each occurrence of the corresponding codon) and 10× T4 RNA ligase reaction buffer (New England Biolabs, B0216L; 1 µL) were mixed in a total volume of 8 L in a PCR tube. The mixture was subjected to the following temperature program on a thermocycler: 95° C. for 10 sec; 65° C. for 4 min; a ramp from 65° C. to 4° C. at 0.1° C. per 10 s. To the PCR tube were added 1 µL of 10 mM ATP and 1 µL of T3 DNA Ligase (New England Biolabs, M0317L; 3000000 units/ml) while the reaction mixture was kept at 4° C. The reaction was incubated at 4° C. for 12 h and then at 16° C. for 2 h. For the evaluation of translation yield on template libraries (FIG. 1C), the reaction mixture was run on nondenaturing 10% TBE polyacrylamide gel electrophoresis and stained with SYBR gold for characterization.

To synthesize an unbiotinylated HFNAP, unbiotinylated primers and a doubly biotinylated ssDNA template (200 pmol), polymerization initiation and termination primers (300 pmol each), functionalized trinucleotide building blocks (2 nmol for each occurrence of the corresponding codon) and 10× T4 RNA ligase reaction buffer (20 µL) were mixed in a total volume of 180 µL. The mixture was split in 10 equal volumes into PCR tubes and subjected to the following temperature program on a thermocycler: 95° C. for 10 sec; 65° C. for 4 min; a ramp from 65° C. to 4° C. at 0.1° C. per 10 s. To each PCR tube were added 1 µL of 10 mM ATP and 1 L of T3 DNA Ligase while the reaction mixture was kept at 4° C. The reaction was incubated at 4° C. for 12 h and then at 16° C. for 2 h. The portions were was used in a solution phase polymerization reaction. After the reaction incubation period, the reaction mixture was combined and 50 µL of a 1% suspension of with MyOne Streptavidin C1 magnetic beads (ThermoFisher Scientific, 65002; 1 µL of the stock 1% suspension per 4 pmol of biotinylated template), and then an equal volume of 2× bind-and-wash buffer (2M NaCl, 2 mM EDTA, 20 mM Tris-HCl, pH 7.5) was added. After 30 minutes of incubation on a rotor, the supernatant was removed by magnetic separation, and the beads were suspended 18 µL of 20 mM NaOH. The supernatant was combined with 12 µL of formamide denaturing mix (95% formamide, 1 mM EDTA) and run on a 10% TBE-urea PAGE gel. Desired product was visualized by UV shadowing at 265 nm against a TLC plate (with F254 indicator), excised from the gel, eluted in 200 µL of TE buffer (10 mM Tris-HCl, 1 mM EDTA, pH 8.0) overnight, filtered, mixed with 2 mL of ssDNA column loading mix (40:60:0.5 v/v/v of saturated aqueous guanidinium chloride/isopropanol/3M sodium acetate, pH 5.2) and cleaned up with a Qiagen QiaQuick column. Typical isolated yield of HFNAP from 200 pmol of template was between 5 and 15 pmol as determined by Nanodrop or quantitative PCR. For the validation of sequence specificity of translation and amplification (FIG. 1D), a small sample (~1 fmol) was amplified by PCR using Q5 DNA polymerase and the primers T7-out-PCR2 and pp2-library. The amplicon was purified by PAGE on a nondenaturing 10% TBE gel and subjected to Sanger sequencing.

Synthesis and isolation of a biotinylated HFNAP followed the same procedure as above, except that an unbiotinylated ssDNA template was used, and one of polymerization primers was doubly biotinylated. After polymerization reaction, streptavidin bead capture, and alkaline denaturation, the bead-bound biotinylated molecules were immobilized on beads as described above. The supernatant was removed, and the beads were washed three times with 20 µL of 20 mM NaOH. The beads were then suspended in 20 µL of formamide denaturing mix (95% formamide, 1 mM EDTA) and heated to 95° C. or 30 min. After cooling to room temperature and magnetic separation, desired product was isolated from the supernatant was directly loaded ontoby PAGE on a 10% denaturing TBE-urea PAGE gel and separated by electrophoresis. Desired product was excised from the gel and eluted. Typical isolated yield of HFNAP from 200 pmol of template was between 5 and 15 pmol as determined by Nanodrop or quantitative PCR.

Synthesis and isolation of a biotinylated, truncated HFNAP (such as PCSK9-Evo5) followed the same procedure, except that the primer contained a 2'-deoxy-U nucleotide, and the ligation reaction mixture was treated with USER enzyme (New England Biolabs) at 37° C. for 2 h before proceeding to streptavidin bead capture.

During the selections, polymerization reactions were performed with templates immobilized on streptavidin beads and processed as detailed in the main text Methods section.

Selection of HFNAPs that Bind Protein Targets

Selection of PCSK9-Binding HFNAPs from a Naïve Library

Recombinant human PCSK9 protein (ACROBiosystems, PC9-H5223) was immobilized onto AminoLink Plus aldehyde-functionalized agarose resin via reductive amination with a MicroLink Protein Coupling Kit (ThermoFisher Scientific, 20475) at a loading of 1 mg protein per mL resin according to the resin's manufacturer's instructions.

To initiate the selection, primer extension was performed with 10 pmol BtBt-ExtA on 5 pmol of sense strand randomized DNA library ("naïve library AZ15") with Klenow (exo-) polymerase (New England Biolabs, M0212S) at 37° C. overnight. The reaction mixture was combined with an equal volume of 2× bind-and-wash buffer (2 M NaCl, 2 mM EDTA, 20 mM Tris-HCl, pH7.5) and immobilized onto 10 µL of a 1% suspension of MyOne Streptavidin C1 magnetic beads. After removal of supernatant, the beads were washed three times with 20 µL of 20 mM NaOH (leaving a biotinylated ssDNA template library on the beads) and then twice with 20 µL of 1× T4 RNA ligase reaction buffer.

To the bead-immobilized template library were added pp1A and pp2Z (7.5 pmol each), a mixture of all 32 functionalized trinucleotide building blocks (100 pmol each), 10× T4 RNA ligase reaction buffer (1 µL), and water to a total of 8 µL. The suspension was transferred to a PCR tube and subjected to the following temperature program on a thermocycler: 95° C. for 10 sec; 65° C. for 4 min; a ramp from 65° C. to 4° C. at 0.1° C. per 10 s. To the PCR tube were added 1 µL of 10 mM ATP and 1 µL of T3 DNA Ligase. The reaction was incubated at 4° C. for 12 h and then at 16° C. for 2 h. An additional 10 µL of a 1% suspension of MyOne Streptavidin C1 magnetic beads and 20 µL of 2× bind-and-wash buffer was added, and the mixture was incubated at room temperature for 30 min before magnetic separation. The supernatant was discarded, and then the unbiotinylated HFNAP strand was eluted from the beads by treatment with 2×30 µL of 20 mM NaOH. To the combined HFNAP fractions was added 600 uL of ssDNA column loading mix (40:60:0.5 v/v/v of saturated aqueous guanidinium chloride/isopropanol/3M sodium acetate, pH 5.2) and the mixture was cleaned up with a Qiagen MinElute column, eluting into 15 µL of water.

The HFNAP was added to 35 µL of DPBS (with calcium and magnesium; Lonza 17-513Q) containing 0.1 mg/ml BSA and 0.01% Tween-20, and then incubated with PCSK9 resin in a micro-spin filtration column (Pierce 89879) at room temperature for 1 h on a rotor. (The amounts of resin-bound protein used in each round are indicated in FIG. 2B.) The flow-through was collected by centrifugation at 1000 g into an Eppendorf tube. The beads in the column were washed three times with 50 µL each of DPBS, each wash being collected by centrifugation as well. The column was cut open and the beads were collected by centrifugation into an Eppendorf tube. To the beads was added 50 µL of a lithium dodecyl sulfate (LDS)-containing buffer (Life Technologies B0007, diluted 4-fold), and the tube was incubated at 95° C. for 15 min. After cooling, 600 uL of ssDNA column loading mix was added, and the mixture was cleaned up with a QiaQuick column, eluting the HFNAP into 50 µL of water.

Samples of 1 µL each from the flow-through, the three washes, and the elution were quantified by qPCR (20 µL reaction volume) using the iTaq Supermix (Biorad, 172-5125) with pp2Z and ExtA (500 nM each) as primers under the following temperature program: 95° C. for 3 min; 35 cycles of 95° C. for 15 s, 59.5° C. for 30 s, 72° C. for 15 s. The number of cycles for the qPCR curve on the elution sample to reach the end of exponential growth was used as the number of cycles for the preparative PCR (400 µL reaction volume split into 8×50 µL) using Q5 Hot Start High-Fidelity 2× Master Mix (New England Biolabs, M0494), with the selection elution pool (20 µL) as template and pp2Z and BtBt-ExtA (500 nM each) as primers, under the same annealing and extension temperatures as in the qPCR. The finished reaction was mixed with 2 mL of ssDNA column loading mix and cleaned up with a Qiagen MinElute column, eluting into 15 µL of water. The amplified dsDNA was purified by PAGE on a non-denaturing 10% TBE gel. A portion (indicated in FIG. 2B) of the gel-purified product was immobilized on L of a 1% suspension of MyOne Streptavidin C1 magnetic beads, strand-separated with 20 mM NaOH, and the immobilized template strand was used for HFNAP translation to initiate the next round of selection.

Evolution of PCSK9-A5 for Higher Affinity

The evolution of PCSK9-A5 was performed in a similar fashion with the following differences. Rediv library AZ15 (custom synthesized by TriLink BioTechnologies) was used to initiate the selection. The primer pp1A-3ddC was used instead of pp1A for ligase-based polymerization in order to facilitate the removal of cheaters (FIG. 7). After two rounds of selection using the same PCSK9 bead loading as before, beads with reduced loading (150 µg protein per mL resin for rounds 3-5; 40 µg protein per mL resin for round 6) were used for affinity enrichment.

Selection of IL-6-Binding HFNAPs from a Naïve Library

The selection of IL-6-binding HFNAPs was performed in a similar fashion with the following differences. Recombinant human IL-6 protein (PeproTech, 200-06) immobilized on AminoLink Plus aldehyde at 0.25 mg protein per ml resin was used as the immobilized target. Throughout the selection, 240 pmol of immobilized IL-6 protein was used in each round. A primer extension on naïve library CW15 with BtBt-ExtC was used to initiate the selection. The primers pp1C and pp2W were used for ligase-based polymerization (translation) reactions. The primers ExtC and pp2W were used for qPCR reactions. The primers BtBt-ExtC and pp2W were used in PCR reactions that amplify affinity-enriched HFNAP into dsDNA for initiating the next round of selection.

High-Throughput DNA Sequencing and Data Analysis

Small samples from the elution pool of selection rounds were amplified by PCR using Q5 Hot Start High-Fidelity 2× Master Mix with MiSeqA and MiSeqZ as primers to sub-saturation number of cycles (determined during the selection by qPCR) with primers that install flanking sequences. The amplicons were PAGE-purified and amplified by PCR with Illumina adapter primers. The amplicons were again PAGE-purified and subjected to high-throughput sequencing on an Illumina MiSeq.

For the IL-6 selection, samples were similarly prepared by PCR amplification with MiSeqC and MiSeqW. The amplicons were PAGE-purified and PCR amplified with Illumina adapter primers. The amplicons were again PAGE-purified and subjected to high-throughput sequencing on an Illumina MiSeq.

Processing and Analysis of High-Throughput Sequencing Data

The FASTQ files from high-throughput sequencing were first processed with CutAdapt for the following operations: a quality-based trim (with a threshold Phred score of 30), removal of constant regions (with a one-base error tolerance in each region; sequences were discarded if either constant region was not found), and filtering for the correct length (45) in the remaining sequence. Sequences that could not be completely parsed into trimer codons (whose first nucleobase should always be C or T) were discarded.

For the initial PCSK9 selection and the IL-6 selection, the copy numbers of all unique sequences were tallied and the unique sequences above 5 reads per million were clustered using FASTAptamer. Sequence logos for PCSK9 selection-enriched sequences were then generated for individual clusters with WebLogo 3. For the PCSK9-A5 evolution, sequence logos were generated directly from sequencing data with WebLogo 3.

Affinity Characterization by Bead Retention Assay

Candidate PCSK9-binding HFNAPs (from 0.5 pmol template via a ligase-catalyzed polymerization reaction) or sequence-matched unfunctionalized DNA (0.5 pmol) in 50 µL of DPBS (with calcium and magnesium) containing 0.1 mg/ml BSA and 0.01% Tween-20 was incubated with 1 µL of either PCSK9 beads or thrombin beads (AminoLink Plus aldehyde-functionalized agarose resin with protein loaded at 1 mg protein per mL resin via reductive amination) in a micro-spin filtration column (Pierce 89879) at room temperature for 1 h on a rotor. Following the same procedure described for the selection, flow-through was collected, the beads were washed three times and the retained HFNAP or DNA was eluted by heating, and the amount of amplifiable HFNAP or DNA in the flow-through, wash, and elution samples were quantified by qPCR.

Candidate IL-6-binding HFNAPs and sequence-matched DNA were similarly assayed on PCSK9 beads (prepared as above, but serving as negative control) or on IL-6 beads (AminoLink Plus aldehyde-functionalized agarose resin with protein loaded at 0.25 mg protein per mL resin via reductive amination).

Detailed Procedures for Surface Plasmon Resonance (SPR) Assays

All SPR assays were performed at 25° C. on a Biacore X100 or Biacore T200 (GE Healthcare Life Sciences). Binding kinetics between enzymatically synthesized biotinylated HFNAPs and unlabeled PCSK9 (ACROBiosystems, PC9-H5224) were measured using single-cycle kinetics with the Biotin CAPture kit (GE Life Sciences, 28920233 or 28920234). HBS-EP buffer (GE Life Sciences, BR100188), diluted by MilliQ water to 0.9×, was used as the bulk running buffer. Each experiment consisted of three start-up cycles followed by multiple data collection and blank cycles. In each data collection cycle, the CAP reagent was injected onto both active and control flow cells of the CAP chip to generate streptavidin-coated surfaces, and then a doubly biotinylated HFNAP was injected onto the active flow cell as the immobilized ligand. Afterwards, four ascending concentrations of PCSK9 protein [10, 30, 100, 300 nM protein supplemented with 1 mg/ml salmon sperm DNA (Invitrogen, 15632-011) as nonspecific binding reducer for PCSK9-A5 and its variants; 2, 6, 20, 60 nM protein without salmon sperm DNA for PCSK9-Evo5 and its variants] in 0.9×HBS-EP were injected onto both flow cells in series at 30 µL/min for 150 seconds each, followed by 240 seconds of dissociation. Both flow cells were then regenerated with a 3:1 mixture of 8 M guanidinium chloride and 1 M NaOH following manufacturer's instructions. Blank cycles were run similarly except that 0.9×HBS-EP (containing 1 mg/ml salmon sperm DNA when PCSK9-A5 and its variants were assayed) without PCSK9 protein was injected. As signals from blank cycles were similar regardless of the immobilized HFNAP, one blank cycle was run for every two data collection cycles. Kinetic parameters were fitted to double-blank-subtracted sensograms using BIAEvaluation software under a 1:1 binding model, unless stated otherwise. Binding between biotinylated Evo5 and truncated PCSK9 protein missing the prodomain ("human mature PCSK9", ACROBiosystems, PC9-H5226) was also assayed using this protocol.

Binding kinetics between enzymatically synthesized biotinylated HFNAPs and unlabeled IL-6 protein, expressed in either E. coli (PeproTech, 200-06) or human HEK293 cells (ACROBiosystems, IL6-H4218), were assayed similarly with the following differences. Four ascending concentrations (10, 30, 100, 300 nM) of IL-6 without additional nonspecific binding reducer were injected in the single-cycle kinetic runs. As the binding kinetics did not fit a classical 1:1 binding model, a heterogeneous ligand model was used to fit the double-blank-subtracted sensograms.

Binding kinetics between chemically synthesized Evo5-syn and biotinylated Avi-tagged PCSK9 (ACROBiosystems, PC9-H82E7) were measured using single-cycle kinetics with on a Series S SA chip (GE Life Sciences, BR100531) using 0.9×HBS as the bulk running buffer. Both active and control flow cells were conditioned with three consecutive one-minute injections of 1 M NaCl in 50 mM NaOH. Biotinylated PCSK9 in 0.9×HBS buffer was immobilized onto the active flow cell to ~1000 RU. Either five portions of buffer or five ascending concentrations of Evo5-syn (1.8, 6, 18, 60, 180 nM) were injected onto both flow cells in series at 30 µL/min for 150 seconds each, followed by 600 seconds of dissociation. Kinetic parameters were fitted to double-blank-subtracted sensograms under a 1:1 binding model using BIAEvaluation software.

Binding of PCSK9 on surface-immobilized LDLR in the presence of various competing agents was measured on a Series S SA chip. The bulk running buffer was 10 mM HEPES, 150 mM NaCl, 0.1 mM $CaCl_2$), 0.005% Tween-20, pH 7.5. Both active and control flow cells were conditioned with three consecutive one-minute injections of 1 M NaCl in 50 mM NaOH, and then biotinylated Avi-tagged LDLR (BPS Bioscience, 71206) was immobilized onto the active flow cell to ~2000 RU. In each data collection cycle, a solution consisting of PCSK9 (20 nM final), a carboxymethyl dextran-based non-specific binding reducer (GE Healthcare, BR-1006-91, 1 mg/ml final), and varying concentrations (0, 2, 6, 20, 60, or 200 nM final) of PCSK9-Evo5-syn, Evo5DNA-InvdT, unlabeled LDLR (AcroBiosystems, LDR-H5224), or a known PCSK9-neutralizing antibody (BPS Bioscience, 71207) in bulk running buffer was injected at 10 L/min for 420 s, followed by 15 s of dissociation. The surface was regenerated using two consecutive one-minute injections of 50 mM HCl. Blank cycles were run similarly except that running buffer containing 1 mg/ml non-specific binding reducer without protein was injected. Response levels at the end of the injection periods from double-blank-subtracted sensograms were recorded.

Electrophoretic Mobility Shift Assay (EMSA)

A 7.5% Tris-Glycine polyacrylamide gel (Bio-rad, 5671024) was pre-run at 150 V for 1 hour at 4° C. in a cold room. Mixtures (12 µl each) of PCSK9-Evo5-Fluor or a sequence-matched DNA (1 nM final), PCSK9 protein (ACROBiosystems, PC9-H5223, between 0.3 and 300 nM final), and salmon sperm DNA (Invitrogen, 15632-011, 30 µg/ml final) in 0.5×HBS-EP buffer (diluted from HBS-EP buffer, GE Life Sciences, BR100188) containing 3% v/v glycerol was incubated at 25° C. for 30 minutes, and then at 4° C. for 5 minutes. The mixtures were loaded onto the pre-run gel and run at 150 V for 15 minutes at 4° C. The gel was imaged with a Typhoon imager using the Cy5 channel. DNA secondary structure prediction was performed on the mfold Web server.

Supplementary Text

The ligase-catalyzed polymerization can produce "cheater" byproducts by incorporating a polymerization primer into the reading frame, resulting in shorter products that more rapidly amplify during PCR (FIG. 7). While our first PCSK9-binding selection campaign was not substantially affected by cheaters, our initial attempt at evolving PCSK9-A5 for higher affinity was unsuccessful because the cheaters eventually took over the pool. To suppress cheaters, in our subsequent attempt at evolving PCSK9-A5 for higher affinity, we used a non-extendable 2',3'-dideoxyribose-terminated 3'-primer in polymerization reactions, so that cheater sequences would be shorter than desired full-length translation products and could be removed by the PAGE purification step at the end of each selection cycle (FIG. 2A and FIG. 7).
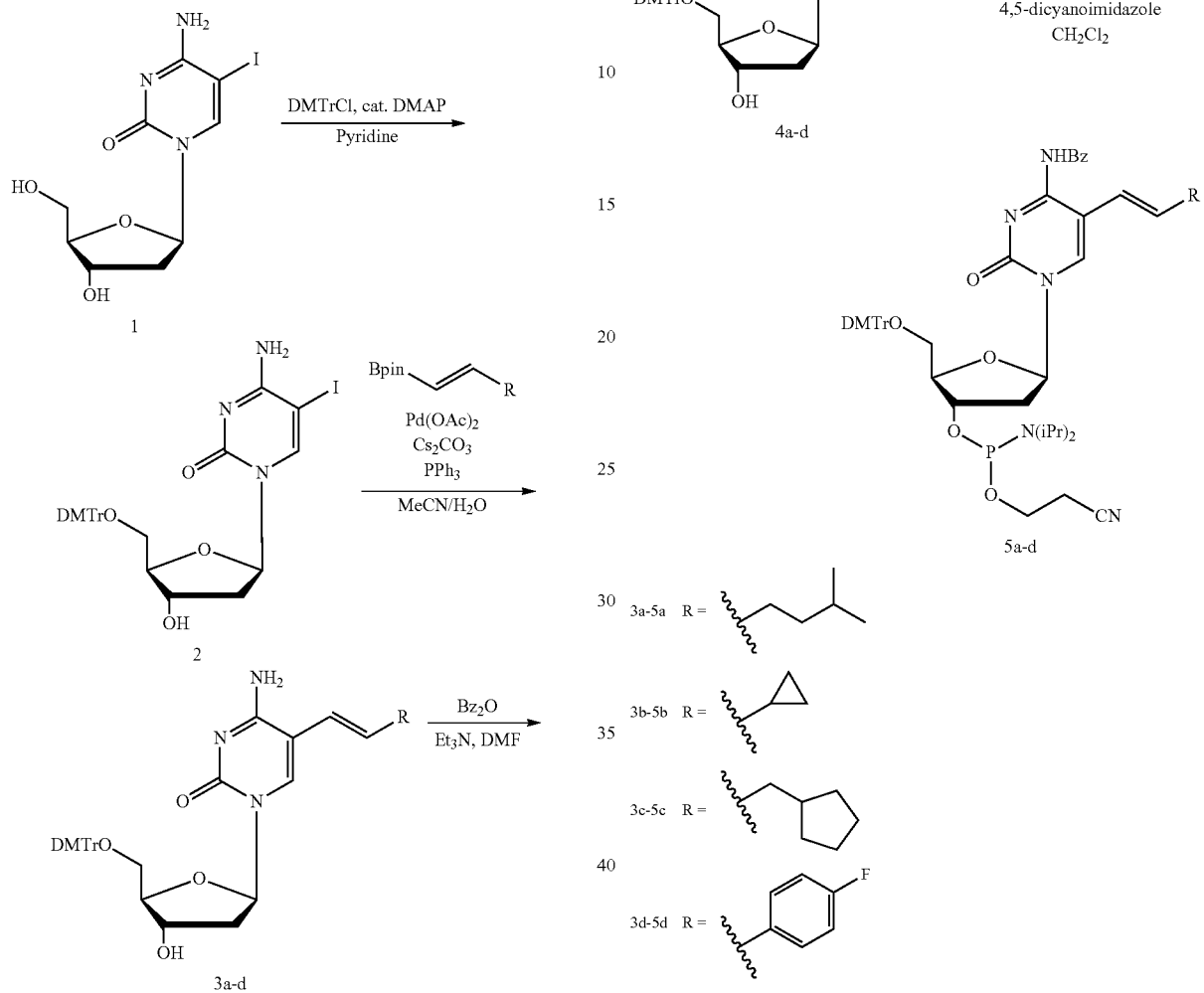
Scheme S1. Synthesis routes to phosphoramidites 5a-5d.
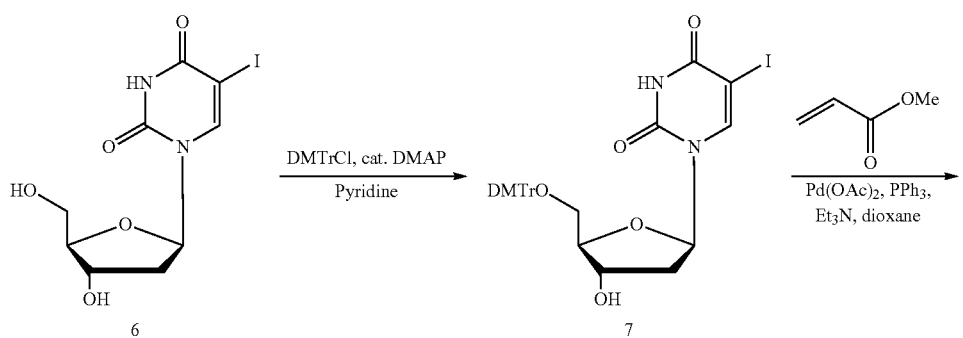
Scheme S2. Synthesis route to phosphoramidite 11.

-continued
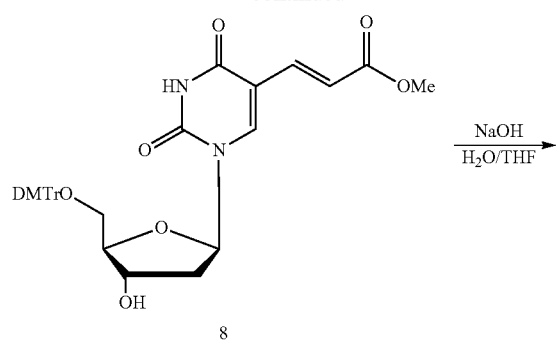
8
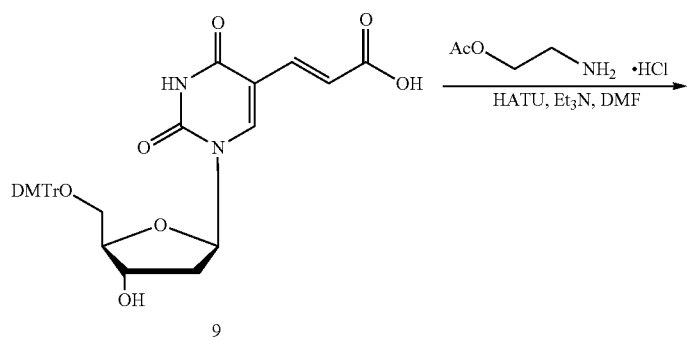
9
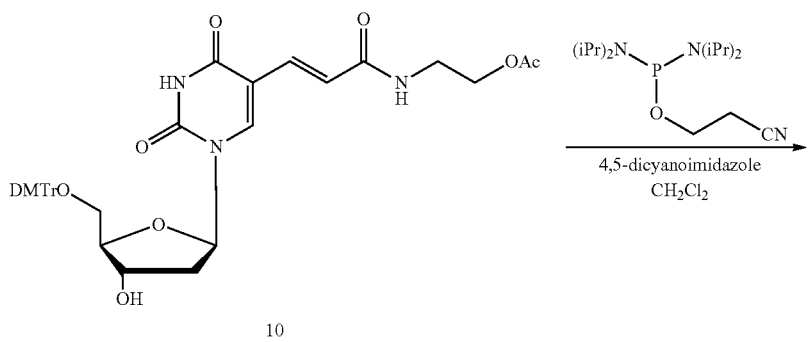
10
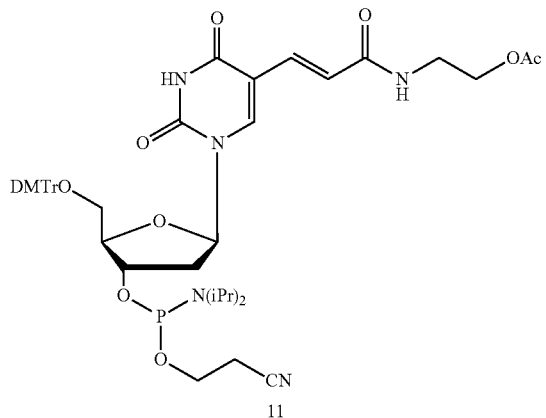
11

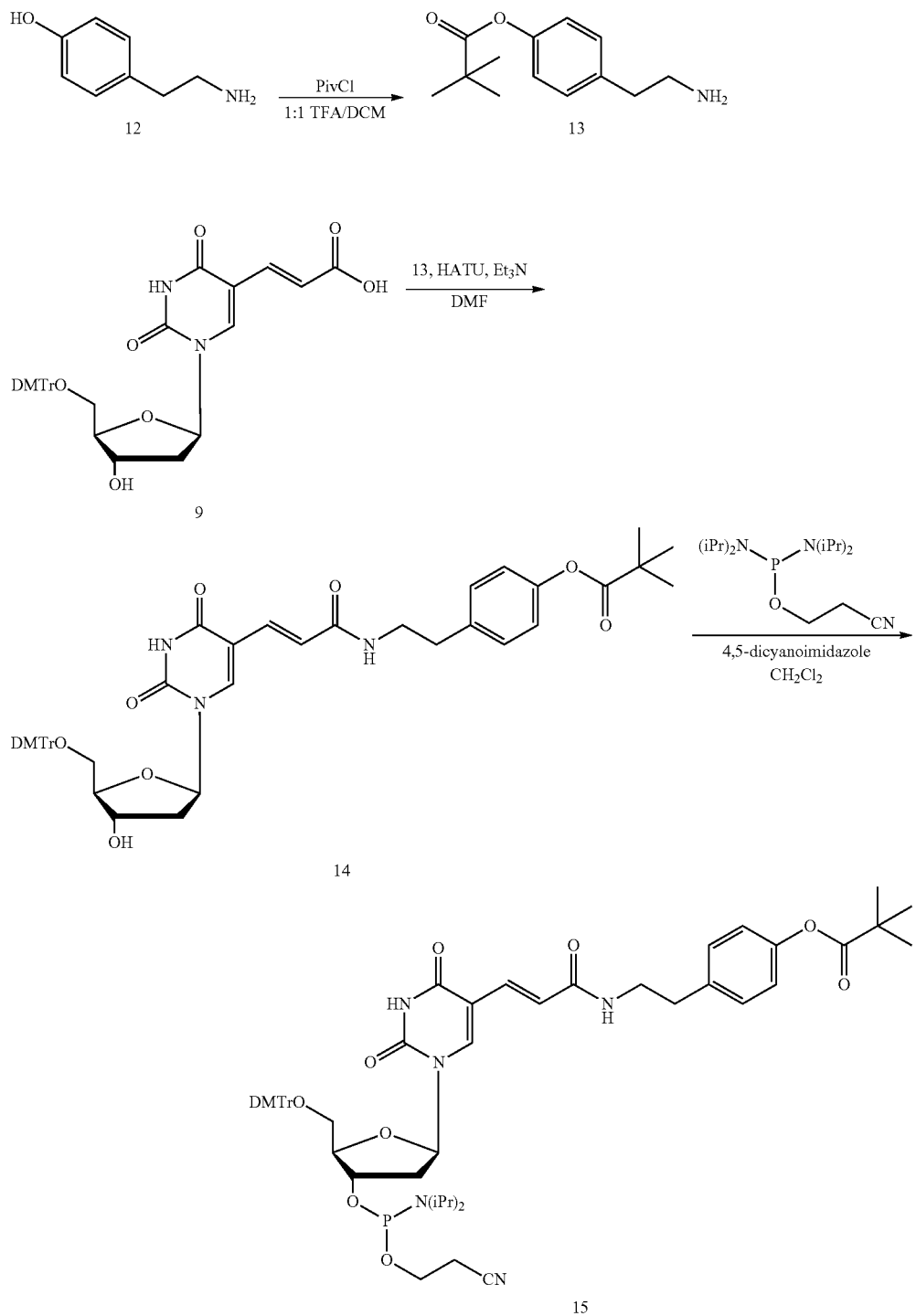

Scheme S3. Synthesis route to phosphoramidite 15.

SUPPLEMENTARY REFERENCES

1. Martin, M. Cutadapt removes adapter sequences from high-throughput sequencing reads. *EMBnet. journal* 17, 10-12 (2011).
2. Alam, K. K., Chang, J. L. & Burke, D. H. FASTAptamer: A Bioinformatic Toolkit for High-throughput Sequence Analysis of Combinatorial Selections. *Mol. Ther. —Nucleic Acids* 4, e230 (2015).
3. Crooks, G. E., Hon, G., Chandonia, J.-M. & Brenner, S. E. WebLogo: a sequence logo generator. *Genome Res.* 14, 1188-1190 (2004).
4. Zuker, M. Mfold web server for nucleic acid folding and hybridization prediction. *Nucleic Acids Res.* 31, 3406-3415 (2003).

What is claimed is:

1. A modified nucleic acid library comprising one or more tri-oligonucleotides, wherein each of the one or more tri-oligonucleotides comprises one or more modified cytosine (C) residues of (a) and/or one or more modified thymine (T) residues of (b), at the 5' end of the one or more tri-oligonucleotides:

(a) wherein the one or more modified C residues are of the formula:

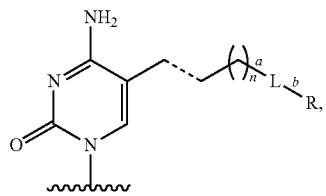

and (b) wherein the one or more modified T residues are of the formula:

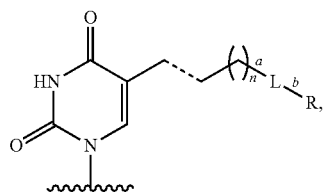

wherein:
each instance of - - - is independently a single, double, or triple bond;
each instance of n is independently 0, 1, 2, 3, 4, 5, or 6;
each instance of $\overset{a}{\text{—}}L\overset{b}{\text{—}}$ is independently a single bond, —O—, —S—, —N($R^A$)—, —C(=O)—, —C(=O)O—, —C(=O)N($R^A$)—, —C(=N$R^A$)—, —C(=N$R^A$)O—, —C(=N$R^A$)N($R^A$)—, —N$R^A$C(=O)—, —N$R^A$C(=O)O—, —N$R^A$C(=O)N($R^A$)—, —N$R^A$C(=N$R^A$)—, —N$R^A$C(=N$R^A$)O—, —N$R^A$C(=N$R^A$)N($R^A$)—, —OC(=O)—, —OC(=O)O—, —OC(=O)N($R^A$)—, —OC(=N$R^A$)—, —OC(=N$R^A$)O—, or —OC(=N$R^A$)N($R^A$)—, wherein each instance of $R^A$ is independently hydrogen, substituted or unsubstituted $C_{1-6}$ alkyl, or a nitrogen protecting group; and
each instance of R is independently unsubstituted $C_{1-5}$ alkyl; substituted or unsubstituted $C_{2-5}$ alkenyl; substituted or unsubstituted $C_{2-5}$ alkynyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl.

2. A modified nucleic acid library comprising one or more tri-oligonucleotides, wherein each of the one or more tri-oligonucleotides comprises one or more modified cytosine (C) residues of (a) and/or one or more modified thymine (T) residues of (b), at the 5' end of the one or more tri-oligonucleotides:

(a) wherein the one or more modified C residues are of the formula:

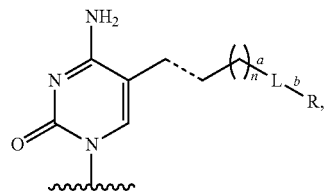

and (b) wherein the one or more modified T residues are of the formula:

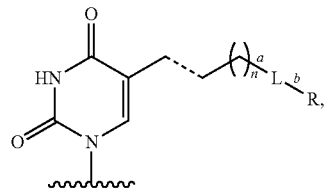

wherein:
each instance of - - - is independently a single, double, or triple bond;
each instance of n is independently 0, 1, 2, 3, 4, 5, or 6;
each instance of $\overset{a}{\text{—}}L\overset{b}{\text{—}}$ is independently a single bond, —O—, —S—, —N($R^A$)—, —C(=O)—, —C(=O)O—, —C(=O)N($R^A$)—, —C(=N$R^A$)—, —C(=N$R^A$)O—, —C(=N$R^A$)N($R^A$)—, —N$R^A$C(=O)—, —N$R^A$C(=O)O—, —N$R^A$C(=O)N($R^A$)—, —N$R^A$C(=N$R^A$)—, —N$R^A$C(=N$R^A$)O—, —N$R^A$C(=N$R^A$)N($R^A$)—, —OC(=O)—, —OC(=O)O—, —OC(=O)N($R^A$)—, —OC(=N$R^A$)—, —OC(=N$R^A$)O—, or —OC(=N$R^A$)N($R^A$)—, wherein each instance of $R^A$ is independently hydrogen, substituted or unsubstituted $C_{1-6}$ alkyl, or a nitrogen protecting group; and
each instance of R is independently

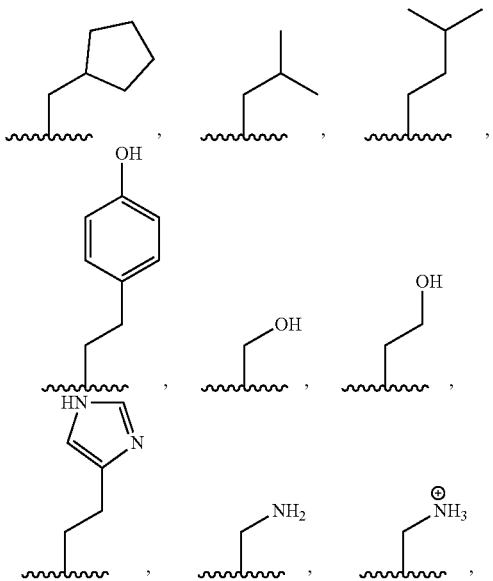

-continued

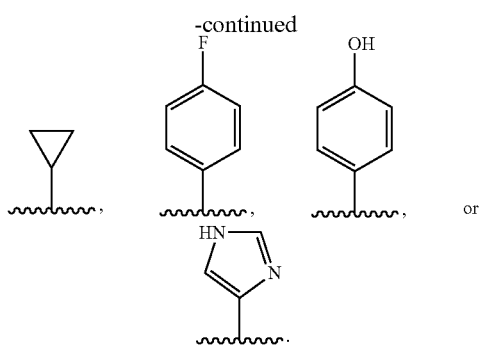

3. The modified nucleic acid library of claim 2, wherein the modified nucleic acid library comprises one or more of the following modified tri-oligonucleotides:

(a) $C_1TT$, $C_1TG$, $C_1GT$, and $C_1CG$, wherein $C_1$ is

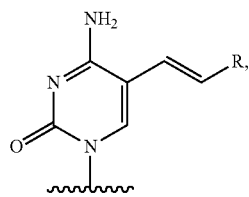

wherein R is

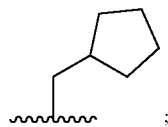

(b) $C_2AA$, $C_2AC$, $C_2TC$, and $C_2GG$, wherein $C_2$ is

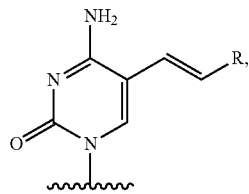

wherein R is

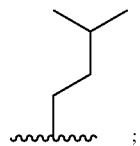

(c) $C_3AT$, $C_3AG$, $C_3GA$, and $C_3GC$, wherein $C_3$ is

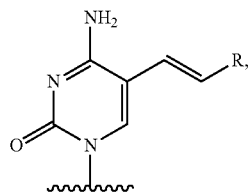

wherein R is

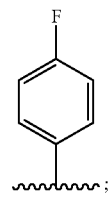

(d) $C_4TA$, $C_4CA$, $C_4CT$, and $C_4CC$, wherein $C_4$ is

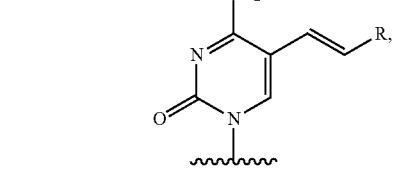

wherein R is

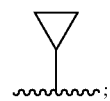 [SMILES: *C1CC1]

(e) $T_1TT$, $T_1TG$, $T_1GT$, and $T_1CG$, wherein $T_1$ is

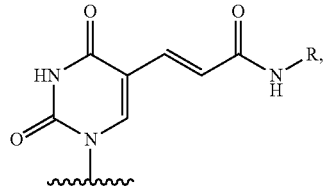

wherein R is

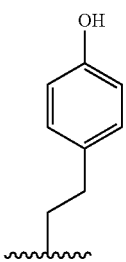

(f) $T_2AT$, $T_2AG$, $T_2GA$, and $T_2GC$, wherein $T_2$ is

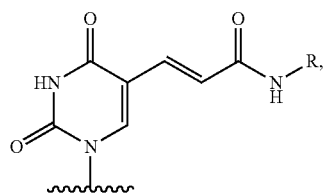

wherein R is

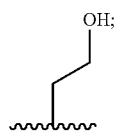 [SMILES: *CCO]

(g) T₃AA, T₃AC, T₃CA, and T₃CC, wherein T₃ is

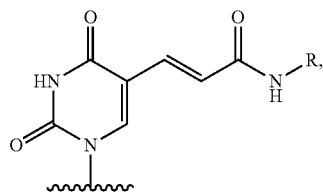

wherein R is

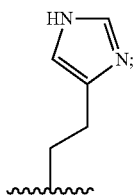 [SMILES: *CCc1c[nH]cn1]

and (h) T₄TA, T₄TC, T₄CT, and T₄GG, wherein T₄ is

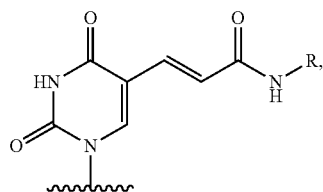

wherein R is

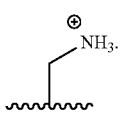

4. A method of making a modified nucleic acid polymer, the method comprising
(a) contacting two or more nucleic acid molecules from the library of claim 1 with a template nucleic acid, thereby forming a complex, wherein the two or more nucleic acid molecules from the library bind to the template nucleic acid, and
(b) contacting the complex of (a) with a ligase, thereby ligating the two or more nucleic acid molecules from the library to form the modified nucleic acid polymer.

5. A method of making a library of modified nucleic acid polymers, the method comprising
(a) contacting the modified nucleic acid library of claim 1 with a library of template nucleic acids, thereby forming complexes between modified nucleic acids of the modified nucleic acid library and template nucleic acids of the library of template nucleic acids, and
(b) contacting the complexes of (a) with a ligase, thereby forming a library of modified nucleic acid polymers.

6. A method of generating a modified nucleic acid polymer that binds to a target protein comprising
(a) contacting the library of modified nucleic acid polymers made by a method of claim 5 with the target protein, and
(b) isolating one or more nucleic acid polymers that bind to the target protein.

7. The modified nucleic acid library of claim 1, wherein each instance of - - - is a double bond.

8. The modified nucleic acid library of claim 1, wherein each instance of n is 0.

9. The modified nucleic acid library of claim 7, wherein each instance of $\underset{L}{\overset{a\quad b}{\phantom{x}}}$ is independently a single bond or —C(=O)N(R⁴)—.

10. The modified nucleic acid library of claim 1, wherein each instance of $\underset{L}{\overset{a\quad b}{\phantom{x}}}$ is independently a single bond or —C(=O)NH—.

11. The modified nucleic acid library of claim 1, wherein the modified nucleic acid library comprises more than one of the tri-oligonucleotides.

12. The modified nucleic acid library of claim 1, wherein each of the one or more tri-oligonucleotides comprises one modified C residue of (a) or one modified T residue of (b).

13. The modified nucleic acid library of claim 11, wherein each of the one or more tri-oligonucleotides comprises one modified C residue of (a) or one modified T residue of (b).

14. The modified nucleic acid library of claim 3, wherein the modified nucleic acid library comprises the modified tri-oligonucleotides of (a) to (h).

15. The modified nucleic acid library of claim 1, wherein each instance of n is independently 0, 1, 2, or 3.

16. The modified nucleic acid library of claim 1, wherein each instance of R is independently unsubstituted $C_{1-5}$ alkyl; substituted or unsubstituted, 3- to 13-membered, monocyclic or bicyclic carbocyclyl; substituted or unsubstituted, 3- to 13-membered, monocyclic or bicyclic heterocyclyl; substituted or unsubstituted, 6- to 11-membered, monocyclic or bicyclic aryl; or substituted or unsubstituted, 5- to 11-membered, monocyclic or bicyclic heteroaryl.

17. The modified nucleic acid library of claim 1, wherein each instance of R is independently unsubstituted $C_{1-5}$ alkyl; substituted or unsubstituted, 3- to 13-membered, monocyclic or bicyclic carbocyclyl; substituted or unsubstituted, 6- to 11-membered, monocyclic or bicyclic aryl; or substituted or unsubstituted, 5- to 11-membered, monocyclic or bicyclic heteroaryl.

* * * * *